US012422430B2

(12) United States Patent
Hanes, Jr. et al.

(10) Patent No.: US 12,422,430 B2
(45) Date of Patent: Sep. 23, 2025

(54) FLUID ANALYSES AND SENSOR CONSTRUCTS EMPLOYING HEXASUBSTITUTED BENZENES

(71) Applicant: Countertrace, LLC, Manvel, TX (US)

(72) Inventors: Robert E. Hanes, Jr., Missouri City, TX (US); Richard L. Pettys, Pearland, TX (US); David M. Headley, Pearland, TX (US); Paul T. Hoopingarner, Missouri City, TX (US)

(73) Assignee: Countertrace, LLC, Manvel, TX (US)

( * ) Notice: Subject to any disclaimer, the term of this patent is extended or adjusted under 35 U.S.C. 154(b) by 884 days.

(21) Appl. No.: 17/637,972

(22) PCT Filed: Sep. 10, 2020

(86) PCT No.: PCT/US2020/050108
§ 371 (c)(1),
(2) Date: Feb. 24, 2022

(87) PCT Pub. No.: WO2021/050669
PCT Pub. Date: Mar. 18, 2021

(65) Prior Publication Data
US 2022/0283152 A1    Sep. 8, 2022

Related U.S. Application Data

(60) Provisional application No. 62/898,227, filed on Sep. 10, 2019, provisional application No. 62/898,258, (Continued)

(51) Int. Cl.
*G01N 33/543* (2006.01)
*E21B 47/00* (2012.01)

(52) U.S. Cl.
CPC .......... *G01N 33/5438* (2013.01); *E21B 47/00* (2013.01)

(58) Field of Classification Search
CPC .............. G01N 33/5438; G01N 33/18; G01N 33/2835; G01N 33/48707; G01N 31/22; G01N 33/54353; E21B 47/00
See application file for complete search history.

(56) References Cited

U.S. PATENT DOCUMENTS

| 4,448,935 A | 5/1984 | Iovine et al. |
| 4,650,910 A | 3/1987 | Henneke et al. |

(Continued)

FOREIGN PATENT DOCUMENTS

| CN | 102295728 A | 12/2011 |
| CN | 102500290 | 6/2012 |

(Continued)

OTHER PUBLICATIONS

EP Search Report from corresponding EP Application No. 20863349 mailed Nov. 8, 2023.

(Continued)

*Primary Examiner* — Lyle Alexander
*Assistant Examiner* — Dwan A Gerido
(74) *Attorney, Agent, or Firm* — Foley & Lardner LLP

(57) ABSTRACT

Phenyl rings provide a robust scaffold for molecular design, given the limited number of ring carbon atoms and the fixed geometry in between. Alternating groups in hexasubstituted benzenes may be directed toward opposite faces of the phenyl ring, such that orthogonal reactive groups are directed toward the opposite faces for promoting both surface attachment and introduction of functionalities suitable for promoting analyte detection. Hexasubstituted benzenes capable of covalent bonding to a surface and having functionalities capable of promoting detection of one or more analytes in fluids may be realized. An analytical response of the hexasubstituted benzenes or a change thereof may be (Continued)

correlated to an amount of at least one analyte present in a fluid, including both single- and multi-phase complex fluids.

12 Claims, 6 Drawing Sheets

Related U.S. Application Data filed on Sep. 10, 2019, provisional application No. 62/898,209, filed on Sep. 10, 2019, provisional application No. 62/898,182, filed on Sep. 10, 2019, provisional application No. 62/898,201, filed on Sep. 10, 2019, provisional application No. 62/898,244, filed on Sep. 10, 2019.

(56) References Cited

U.S. PATENT DOCUMENTS

| | | | |
|---|---|---|---|
| 4,668,739 | A | 5/1987 | Berdahl et al. |
| 4,857,580 | A | 8/1989 | Patzschke et al. |
| 5,073,603 | A | 12/1991 | Eikenberry et al. |
| 5,841,001 | A | 11/1998 | Tanaka et al. |
| 5,895,796 | A | 4/1999 | Mouri et al. |
| 5,981,807 | A | 11/1999 | Kodama et al. |
| 6,048,732 | A | 4/2000 | Anslyn et al. |
| 6,794,448 | B2 | 9/2004 | Sakuma |
| 6,812,276 | B2 | 11/2004 | Yeager |
| 6,946,070 | B2 | 9/2005 | Hammen et al. |
| 8,791,188 | B2 | 7/2014 | Ghandi |
| 2004/0063870 | A1 | 4/2004 | Burns et al. |
| 2005/0124707 | A1 | 6/2005 | Eldridge et al. |
| 2006/0068317 | A1 | 3/2006 | Klei et al. |
| 2008/0099715 | A1 | 5/2008 | Adams et al. |
| 2009/0215646 | A1 | 8/2009 | Anslyn et al. |
| 2011/0122590 | A1 | 5/2011 | Wilson et al. |
| 2012/0271064 | A1 | 10/2012 | Henninger et al. |
| 2013/0157905 | A1 | 6/2013 | Saini et al. |
| 2016/0339412 | A1 | 11/2016 | Rasmussen et al. |
| 2018/0065904 | A1 | 3/2018 | Pappo et al. |
| 2018/0304684 | A1 | 10/2018 | Rannoux et al. |

FOREIGN PATENT DOCUMENTS

| | | |
|---|---|---|
| CN | 105693918 | 6/2016 |
| CN | 109206623 | 1/2019 |
| DE | 10355169 | 6/2005 |
| JP | S62-153754 A | 7/1987 |
| JP | 2005170823 | 6/2005 |
| KR | 1020060104662 | 10/2006 |
| WO | 2009119513 | 10/2009 |
| WO | WO-2011/002850 | 1/2011 |
| WO | WO-2013/118100 | 8/2013 |

OTHER PUBLICATIONS

Hopff, Heinrich and A. Wick. "Zur Kenntnis der Hexaalkylbenzole. 3. Mitteilung. Über einen neuen Kohlenwasserstoff C18H24 (Hexaäthylidencyclohexan)." Helvetica Chimica Acta 44 (1961): 380-386.
Hopff, H. and Wick, A.K. (1961), On the Knowledge of Hexaalkylbenzenes. II. Notice. Side chain halogenations of hexaethylbenzene. Helvetica Chimica Acta 44 (1961): 19-44.
Hennrich, G. and Anslyn, E.V. (2002), 1,3,5-2,4,6-Functionalized, Facially Segregated Benzenes—Exploitation of Sterically Predisposed Systems in Supramolecular Chemistry. Chem. Eur. J., 8: 2218-2224.
Meier, Herbert et al. "Synthesis of Hexastyrylbenzenes." Synthesis 1997 (1997): 276-278.
Sha, Chin-Kang et al. "A retro-malonate addition reaction: synthesis of 3,4-condensed heteroaromatic pyrroles." Journal of The Chemical Society, Chemical Communications (1988): 1081-1083.
International Search Report and Written Opinion of corresponding PCT/US2020/050108 dated Dec. 24, 2020.
Hennrich, G., et al., "1,3,5-2,4,6-Functionalized, Facially Segregated Benzenes-Exploitation of Sterically Predisposed Systems in Supramolecular Chemistry," Chem. Eur. J., 2002, pp. 2219-2224, 8.
Cabell, L.A., et al., "Metal triggered fluorescence sensing of citrate using a synthetic receptor," J. Chem. Soc., Perkin Trans. 2, 2001, pp. 315-323.
Sasaki, S., et al., "Design and synthesis of preorganized tripodal fluororeceptors based on hydrogen bonding of thiourea groups for optical phosphate ion sensing," J. Chem. Soc., Perkin Trans. 2, 2001, pp. 2309-2313.
Minodani, S., et al., "Reinforcement of guest selectivity through the self-assembly of host molecules: selective recognition of lithium ions by dimerizable tricarboxylic acids," Chem. Commun., 2015, pp. 12920-12923, 51.
Wallace, K.J., et al., "Preparation of 1,3,5-Tris(aminomethyl)-2,4,6-triethylbenzene from Two Versatile 1,3,5-Tri (halosubstituted) 2,4,6-Triethylbenzene Derivatives," Synthesis, 2005, pp. 2080-2083.
Kilway, K.V., et al., "Control of functional group proximity and direction by conformational networks: synthesis and stereodynamics of persubstituted arenes," Tetrahedron, 2001, pp. 3615-3627, 57.
Anslyn, E.V., "Supramolecular Analytical Chemistry," J. Org. Chem., 2007, pp. 687-699, 72.
PubChem ID 138452, "1,3,5-trichloro-2,4,6-trimethylbenzene," created Mar. 26, 2005.
Ross, S.D., et al., "Preparation of 1,3,5-trivinyl-2,4,6-trichlorobenzene and its copolymerization with styrene," J. Poly. Sci., 1952, pp. 219-228, 9, (Abstract).
Bayramoglu, G., et al., "Ethylenediamine grafted poly{glycidylmethacrylate-co-methylmethacrylate) adsorbent for removal of chromate anions," Separation and Purification Technology, 2005, pp. 192-199, 45.
Caykara, T., et al., "A New Type of Poly{glycidyl methacrylate) Microbeads with Surface Grafted Iminodiacetic Acid: Synthesis and Characterization," Polymer Bulletin, 2008, pp. 311-318, 61.
Collins, Byron E et al: "Pattern-Based Peptide Recognition", Chemistry—A European Journal, John Wiley & Sons, Inc, DE,vol. 13, No. 17, May 8, 2007 (May 8, 2007), pp. 4700-4708,XP071826202, ISSN: 0947-6539, DOI: 10.1002/CHEM.200700153.
European Search Report on EP20864230.6 dated Oct. 10, 2023 (9 pages).
Gavette J et al. "Hydrogen Bonding vs. Steric Gearing in a Hexasubstituted Benzene" (J. Org. Chem. 73: 3582-3584). (Year: 2008).
International Search Report and Written Opinion for PCT/US2020/041407, published Oct. 30, 2020.
International Search Report and Written Opinion for PCT/US2020/041417, published Oct. 26, 2020.
Lavigne J J et al: "Single Analyte to Multi-Analyte Fluorescence Sensors", Proceedings of SPIE, IEEE, US, vol. 3602, Jan. 1, 1999 (Jan. 1, 1999), pp. 220-231, XP000863546, DOI: 10.1117/12. 347545, ISBN: 978-1-62841-730-2.
Lee, S.G., et al., "Amine-functionalized macroporous microspheres for HF removal from aqueous solution," AIP Conference Proceedings, 2016, Article No. 140005, pp. 1-5, 1713.
Liu, C., et al., "Functionalization of adsorbent with different aliphatic polyamines for heavy metal ion removal: Characteristics and performance," J. Colloid and Interface Sci., 2010, pp. 454-460, 345.
Liu, C., et al., "Diethylenetriamine-grafted poly{glydicyl methacrylate) adsorbent for effective copper ion adsorption," J Colloid and Interface Sci., 2006, pp. 99-108, 303.
Nastasovic, A., et al., "Kinetics of hexavalent chromium sorption on amino-functionalized macroporous glycidyl methacrylate copolymer," J. Hazardous Mat., 2009, pp. 153-159, 171.
Radova, Z. et al., "Sorption of Pd(II) from aqueous solutions of chlorocomplexes by the copolymer of glycidylmethacrylate and ethylenedimethacrylate modified with ethylenediamine. The structure of complexes," Die Angewandte Makromolekulare Chemie, 2003, pp. 55-62, 81.
Wang, H., et al., "Polymer monoliths with chelating functionalities for solid phase extraction of metal ions from water," Journal of Chromatography A, 2014, pp. 128-134, 1343.

(56) References Cited

OTHER PUBLICATIONS

Wright, Aaron T. et al: "Differential receptor arrays and assays for solution-based molecular recognition", Chemical Society Reviews, vol. 35, No. 1, Jan. 1, 2006 (Jan. 1, 2006), pp. 14-28, XP055718322, UK, ISSN: 0306-0012, DOI: 10.1039/B505518K.

Yan, X., et al., "Highly Monodisperse Sub-Microspherical Poly{glycidyl methacrylate) Nanocomposites with Highly Stabilized Gold Nanoparticles," Macromol. Chem. Phys., 2014, pp. 1098-1106, 215.

FLUID ANALYSES AND SENSOR CONSTRUCTS EMPLOYING HEXASUBSTITUTED BENZENES

CROSS-REFERENCE TO RELATED APPLICATIONS

The present application claims the benefit of priority under 35 U.S.C. § 119 from U.S. Provisional Patent Applications 62/898,182, 62/898,201, 62/898,209, 62/898,227, 62/898,244, and 62/898,258, each filed on Sep. 10, 2019 and incorporated herein by reference in its entirety.

STATEMENT REGARDING FEDERALLY SPONSORED RESEARCH OR DEVELOPMENT

Not applicable.

BACKGROUND

Detection and quantification of various analytes may be conducted in conjunction with numerous processes, such as quality and process control, medical diagnostic testing, environmental monitoring, and the like. Analytes to be monitored under a given set of circumstances may exhibit wide structural and functional diversity and include substances such as, but not limited to, microorganisms, cells, trace metals, explosive molecules, drug molecules, poisons, solvents, other chemicals, metabolites, and the like. These analytes and many others may be detected through the physical measurement of properties resulting from chemical interactions of analytes with a chemical receptor (sensing functionality) through mechanisms including, but not limited to, charge pairing, charge transfer, hydrophobic effects, reversible covalent bond formation, pH effects, electrochemical behavior, and other processes associated with molecular recognition. Such chemical interactions may be referred herein to as "molecular association." These types of pairwise interactions are similar to the 'lock and key' paradigm commonly used to explain the interactions between biological molecules and natural receptors. The chemical receptor may constitute a portion of a larger molecule or a whole molecule itself. For example, the chemical receptor may recognize strands of amino acids, proteins, sugars, lipids and/or nucleotide sequences that may or may not be fragments of DNA, RNA and general pairings associated with such biological systems. Ligands having at least partial specificity for particular metal ions may also comprise at least a portion of a chemical receptor in some instances.

Suitable procedures may need to be developed and validated for effectively assaying a given analyte of interest, particularly when using general purpose laboratory equipment such as spectrophotometers and electrochemical detection techniques. In some instances, it can be desirable to employ specifically configured media or sensors for conducting analyses of certain analytes, particularly when performing repeated measurements at high throughput, such as during process control and/or monitoring. Sensors or similar media configured for analyzing for a particular analyte of interest may simplify technological challenges associated with such analyses, especially for users having limited laboratory skills and/or for testing in field environments with limited laboratory capabilities. Plate-based analyses featuring specifically functionalized well media may be particularly desirable sensor constructs for conducting multiple analyses in parallel in a high-throughput manner. Flow-through sensors may be desirable sensor constructs for continuous process monitoring and/or control. Flow-through sensors may comprise an active area containing functionality for assaying an analyte of interest, without immersion of the active area in a fluid comprising the analyte. Instead, in a flow-through sensor, fluid is received, passes across the active area as a dynamic stream, and is then discharged.

The sensing functionality in chemical sensors may comprise a particular molecular structure or group of molecular structures that is/are complementary to an analyte of interest, such that the analyte undergoes a specific molecular association with the sensing functionality. Detection of the molecular association and the magnitude thereof may allow an analyte's presence to be determined and the amount of analyte to be quantified based upon a measurable physical property. The sensing functionality may be specific to a single analyte of interest or to a range of analytes of a particular type. The molecular association between the analyte of interest and the sensing functionality may be covalent or non-covalent in nature.

When conducting analyses, it may be desirable to covalently bond a suitable sensing functionality to a surface, particularly for plate-based or flow-through analyses. Covalent bonding of a sensing functionality to a surface may limit loss of the sensing functionality to the surrounding environment, thereby affording a more robust sensing system. Covalent bonding may be particularly desirable for continuous and flow-through sensing systems to facilitate dynamic evaluation of mobile fluid streams. In addition, covalent bonding of a sensing functionality to a surface may provide operational advantages for shelf life and storage. Specifically, various precursors containing a sensing functionality may be stored in a non-covalently bound state and undergo subsequent bonding to a surface at a desired time to form the active portion of a sensor. Indeed, with strategically chosen functionality for promoting covalent bond formation, a chemical sensor may be robotically applied to a surface during manufacture and eliminate the intervention of a technician, who is otherwise required to load a plate with the correct reagents for testing and possibly perform other manipulations to promote robust covalent bond formation to a surface. When fabricating a sensor in this manner, complex chemical sensors ready for near-immediate analyses may be obtained in a high-throughput and/or combinatorial manner, thereby eliminating the usual practice of adding fresh testing reagent to a test plate or well immediately prior to conducting an analysis. That is, precursors to surface-bound sensing functionalities may be stockpiled and rapidly deployed to prepare sensors customized for performing particular analyses, rather than targeted sensors being stockpiled by a supplier or custom-prepared just prior to use, as in many plate-based analyses. Despite the desirability of covalently assembled, surface-bound chemical sensors, such features may oftentimes be difficult to achieve in practice. Moreover, for flow-through analyses, it may not be possible to further modify the analytical environment within the sensor construct through incorporating additional unbound reagents.

Although surface attachment of a sensing functionality or other type of surface-modifying functionality may be desirable and accomplished through a wide range of chemical reactions, there may be several complicating issues when performing analyses using a surface-bound sensing functionality. For example, a linker moiety appending a sensing functionality to a surface may exhibit a high degree of conformational flexibility, thereby affording a wide number of degrees of freedom and positioning the sensing functionality in various possible orientations. The variable orientations of the sensing functionality may alter the extent to which the sensing functionality interacts with an analyte of interest, thereby changing the magnitude of the measured response and leading to potential measurement inaccuracies when analyzing for certain analytes. Similar types of property variability arising from conformational flexibility may also occur when modifying a surface for other application-specific purposes. For example, variable coverage density of a functionalizing group upon a surface may be similarly problematic for producing a functionalized surface having uniform properties. At present, there are very few options for introducing functional modifications to a surface uniformly and in an orientationally controlled manner, particularly for sensing applications. Surface modifications introduced through covalent bond formation while still maintaining uniform surface coverage and orientational control are even rarer still.

It is generally accepted in supramolecular chemistry that 'preorganization' minimizes disfavorable entropy from binding free energies, for the 'entropy price' is paid in the synthesis. This concept is readily exemplified by the simple example of a crown ether or other macromolecular binding construct. When applied to a sensing functionality, analyte binding usually does not require a large entropy price, for the supramolecular assembly configured for interacting with an analyte of interest usually undergoes minimal conformational change when binding the analyte. Entropic contributions may also be decreased by limiting the number of degrees of freedom available by attaching a supramolecular assembly to a surface. Surface attachment may minimize internal rearrangements and create a more favorable analyte binding environment on the whole, in addition to affording the other advantages mentioned above. With a surface-bound sensing functionality, concentration therefore becomes a time-dependent quantity to monitor dynamic changes within a fluid of interest.

Simple fluids containing a single analyte in a routine matrix oftentimes may be analyzed straightforwardly with spectrophotometers and other conventional laboratory equipment. In many instances, however, fluids may contain multiple analytes or a mixture of an analyte of interest and one or more interferents, which may present significant analytical challenges. In addition, the matrix of some fluids may themselves present analytical difficulties. In the disclosure herein, any of the foregoing fluids presenting such analytical difficulties may be considered "complex." Analyses of complex fluids may be exceedingly complicated due to the difficulty of detecting a given analyte with a desired level of specificity or accuracy, particularly when using conventional sensors and non-specific spectrophotometers and laboratory techniques.

Complex fluids are inclusive of fluids containing both single analytes and multiple analytes within one or more phases, optionally in further combination with other substances, or the fluid matrix itself, that may provide analytical interference. The term "single-phase complex fluid" refers to a fluid containing one or more analytes of interest in a homogeneous phase, optionally in further combination with other substances that provide analytical interference. Similarly, the term "multi-phase complex fluid" refers to fluid containing one or more analytes of interest, optionally in further combination with other substances that provide analytical interference, and having stable coexistence between two or more distinct phases, which may be liquid-liquid, solid-liquid, gas-liquid, solid-gas, or gas-liquid-solid. Examples of multi-phase complex fluids may include water-in-oil emulsions, oil-in-water emulsions, solids-in-water emulsions, solids-in-oil emulsions, solids-in oil/water emulsions, solids-in-oil/water/gas emulsions, and the like. Multi-phase complex fluids may include a single analyte of interest, multiple analytes of the same type (similar chemistry and/or structures), multiple analytes of different types (different chemistry and/or structures), or any combination thereof.

When an analyte or multiple analytes are present in a sample of a single- or multi-phase complex fluid, chemical or spectroscopic interference may occur during analyses, such that detection and accurate measurement become problematic. In the case of biological fluids, for example, there may be multiple interfering substances, such as proteins, biological chromophores, and other matrix species that may preclude satisfactory detection and analysis of an analyte of interest. The multi-phasic nature and complex binding properties of many biological fluids may further complicate analyses. For example, binding of an analyte of interest to a biomolecule may make accurate analyses difficult to realize. Oilfield treatment fluids and produced oilfield fluids represent additional examples of single- and multi-phase complex fluids whose analyses likewise may be exceedingly complicated.

In many conventional analyses, a sample may be processed prior to undergoing an analysis to limit the possibility of interference from a related analyte or other substance in a complex fluid. Sample processing in this manner may significantly complicate analyses, increase their cost, and limit performance thereof to highly trained laboratory or clinical personnel. Moreover, when screening for multiple analytes in a complex fluid, different types of sample processing may need to be conducted in order to analyze for particular analytes, since some interferents may be problematic for some analytes but not for others. Such complex and laborious sample processing may significantly limit throughput for obtaining analytical results. Deconvolution of interfering signals from multiple analytes and other interferents may be exceedingly complicated as well.

In the case of biological fluid analyses, delayed analyses and limited analytical throughput can result in significant health impacts for an individual whose treatment decisions are being guided thereby. At best, an individual may remain ill for a longer period of time than otherwise would have occurred had more rapid analytical testing results been available to guide a treatment or therapy decision. At worst, a disease or other condition may progress rapidly while awaiting analyses, thereby requiring more aggressive treatment, hospitalization and/or prolonged recovery periods once a treatment or therapy decision has been made. Poor treatment outcomes and even death may result in some cases from a delayed response to rapidly progressing health conditions, such as sepsis. Incorrect treatment decisions made while awaiting analyses may also be detrimental in some cases.

Oilfield fluids are another type of complex fluid that may be especially difficult to analyze using conventional sensors and laboratory equipment. Oilfield fluids may include treatment fluids, produced water, produced hydrocarbon resources (e.g., oil, gas, or oil/gas mixtures), or any combination thereof. Water or other liquids used in formulating a treatment fluid may similarly be difficult to analyze with sufficient rapidity to determine suitability for use. As used herein, the term "treatment fluid" refers to a fluid that is placed in a subterranean formation in order to perform a desired function. Treatment fluids can be used in a variety of subterranean operations including, but not limited to, drilling operations, production operations, stimulation operations, remediation operations, fluid diversion operations, cleanup operations, and the like. As used herein, the terms "treat," "treatment," and "treating," as they refer to subterranean operations, refer to any subterranean operation that uses a fluid in conjunction with performing a desired function and/or achieving a desired purpose. The terms "treat," "treatment," and "treating," as used herein, do not imply any particular action by the fluid or any particular component thereof unless otherwise specified. Specific treatment fluids can include, for example, drilling fluids, fracturing fluids, acidizing fluids, conformance treatment fluids, diverting fluids, cleanup fluids, damage control fluids, remediation fluids, scale removal and inhibition fluids, chemical floods, sand control fluids, and the like.

Treatment fluids and other fluids encountered in the oilfield may be exceedingly complex and contain a multitude of components. A principal component or components of a treatment fluid may dictate the treatment fluid's ultimate properties and performance while downhole, although additional components or impurities may detrimentally impact performance of the principal component(s), such that the treatment fluid performs less effectively than anticipated or fails to perform its intended function at all. As non-limiting examples, an incorrectly formulated and/or contaminated treatment fluid may have an incorrect viscosity or weight to perform a desired treatment operation, or the treatment fluid may lack an adequate quantity of the principal component to function properly. As such, it can be highly desirable to monitor the quality and composition of a treatment fluid when working in the oilfield. The quality and composition of a produced hydrocarbon resource, such as oil and/or gas, may similarly be desirable to analyze for determining if a treatment operation has produced a desired effect or if it is economically viable to continue operating a well. When water is produced from a wellbore, either alone or in combination with a hydrocarbon resource, analysis of the impurity profile of the water may be desirable for determining if the water may be reintroduced into a disposal well, needs to be further treated, and/or has a sufficient compositional profile for formulating a treatment fluid therefrom. Since treatment fluids are often very sensitive to the presence of impurities, it is very difficult at present to formulate treatment fluids from produced water, particularly given the difficult of quickly analyzing produced water having a complicated impurity profile. Nevertheless, reuse of produced water remains an area of steady research in the oilfield services industry, given the immense quantities of produced water usually available and the sometimes difficult task of supplying water to a job site.

Although treatment fluids and other oilfield fluids may be sampled and analyzed offline in a laboratory, this approach can undesirably delay performance of a treatment operation or production of a hydrocarbon resource from a well. Production delays may result in significant economic consequences when operating a well, and in many cases it is not feasible to delay production while awaiting the outcome of a laboratory analysis. Moreover, there can be changes in the composition of a fluid once the fluid has been removed from its native downhole environment, even if exceptional care is taken to preserve the fluid quality. As such, it would be desirable to perform analyses at a job site in order to speed up analyses and preserve fluid quality for analytical accuracy. However, oilfield personnel may lack sufficient training to sample, process and accurately analyze an oilfield fluid at a job site. Furthermore, conventional laboratory equipment, such as spectrophotometers, may be poorly suited for deployment in process or field environments. In the very best case, fluid analyses conducted at a job site are difficult to perform, sometimes inaccurate, and are not sufficiently rapid to permit real-time analysis and management of a job. Thus, current analyses of oilfield fluids may result in reactive rather than proactive management of a job.

While plate-based and flow-through analyses may be desirable in a number of circumstances, such analyses may remain rather complicated for complex fluids and other fluids containing analytes within difficult analytical environments. At the very least, and as discussed above, identification of a suitable sensing functionality for a given analyte or a range of closely related analytes may remain rather problematic. Moreover, many conventional analyses may necessitate the presence of several components in solution including dyes, buffers, and/or additives to influence equilibrium conditions to promote effective molecular association, which may not be amenable to high-throughput flow-through or plate-based analyses because such components may not be effective bound to a surface and/or require on-site liquid mixing and physical processing to secure accurate analyses. Identifying suitable covalent bonding conditions for appending a multitude of possible sensing functionalities upon a surface, particularly in an orientationally controlled manner, may complicate this situation still further.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
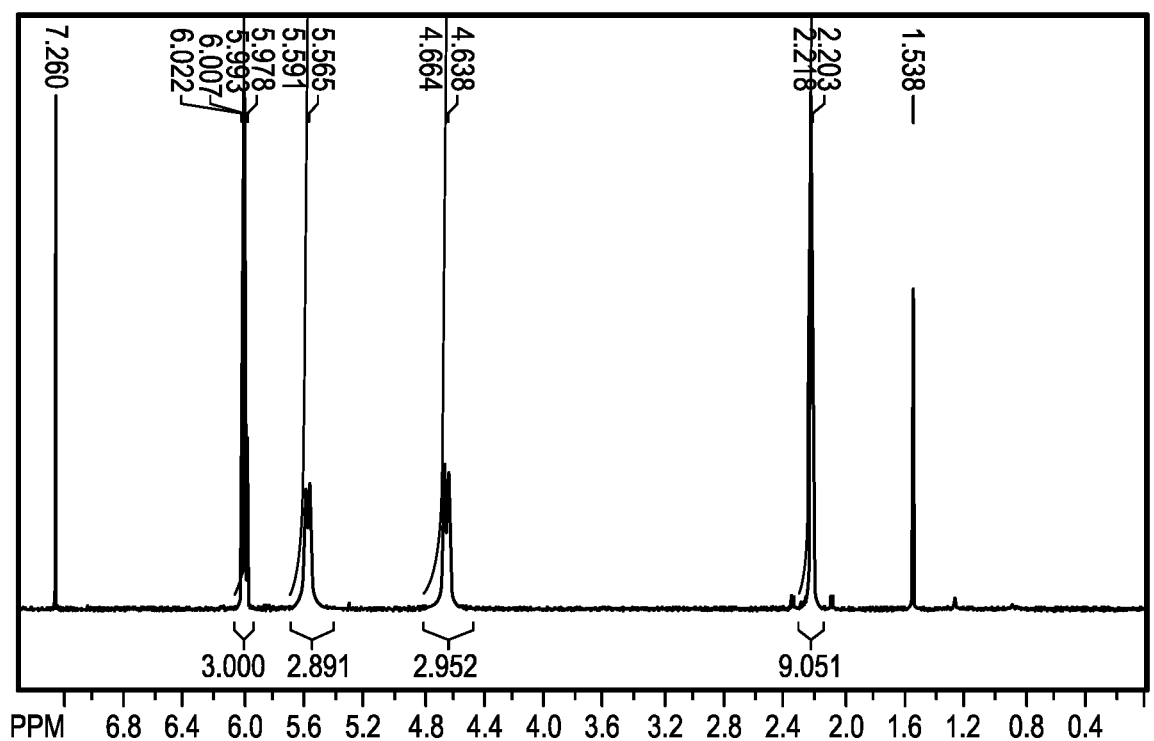
FIGS. 1 and 2 are $^1$H and $^{13}$C NMR spectra of 1,3,5-tris (halomethyl)-2,4,6-tris(α-bromoethyl)benzene in $CDCl_3$, respectively.

The present disclosure generally describes fluid analyses employing hexasubstituted benzenes to promote sensing, particularly surface-bound hexasubstituted benzenes containing at least one functionality capable of undergoing molecular association with an analyte of interest. Simple fluids, as well as single- and multi-phase complex fluids, containing one or more analytes of interest may be particularly desirable for analysis according to the disclosure herein. Among complex fluids that may be analyzed according to the disclosure herein include, but are not limited to, biological fluids, oilfield fluids (including oil, oil components, gas, treatment fluids, produced water, the like, and any combination thereof), and other multi-phase complex fluids encountered in various industries.

As discussed above, fluid analyses, particularly analyses of complex fluids, may present a number of challenges, including interfering chemistries and/or spectroscopic or similar analytical interference. Potential lack of expertise for field personnel tasked with sampling and conducting the analyses may also be complicating issues. Single- and multi-phase complex fluids containing one or more, possibly interfering, analytes and/or other substances, including the fluid matrix, may present particular challenges. Analyses of fluids may be accomplished using a sensor, test strip, plate or flow-through sensor construct configured for assaying one or more analytes of interest. However, such analyses, when conducted conventionally, may be complicated by difficulties in identifying suitable sensing functionalities and consistently bonding the sensing functionalities or related testing reagents to a surface to permit fabrication of a robust sensor construct. Moreover, even if suitable chemistry can be identified for detecting a particular analyte of interest, there can still be issues of the sensing functionality residing in a range of orientations once bound upon a surface. The inconsistent orientations may result in analytical variation from sensor to sensor and lead to difficulties when analyzing complex fluids, such as when deconvoluting a plurality of sensor signals for multiple analytes of interest. Excessive analytical variability when deconvoluting sensor signals may make it impossible to obtain reliable data for one or more of the analytes.

Functionalization of surfaces may be difficult to control, such as when attaching sensing functionalities to a surface during fabrication of a sensor, plate, flow-through testing apparatus, or similar sensor construct. Individual sensors, plate-based sensors, flow-through sensors, or any combination thereof represent illustrative sensor constructs that may be suitably employed in the disclosure herein. As a non-limiting example, sensing functionalities may reside in a range of available orientations once covalently bound to a surface. Variable surface coverage of sensing functionalities may also be an issue. Inconsistent surface coverage and/or conformational variability of sensing functionalities upon a surface may result in surface irregularities and differing surface properties in some instances, which may lead to inconsistent sensing performance. Thus, even if suitable sensing functionalities and chemistry to bond the sensing functionalities to a given type of surface can be identified, there may still be issues of sensing accuracy due to the range of orientations available once the sensing functionalities have become surface bound.

The present disclosure demonstrates that various hexasubstituted benzenes may serve as robust and versatile molecular scaffolds for promoting covalent attachment of a range of sensing functionalities to various types of surfaces. The sensing functionalities may be utilized to analyze for one or more analytes in fluids according to the present disclosure, including single- or multi-phase complex fluids, wherein suitable complex fluids and analytes therein are not believed to be particularly limited in scope. Specific complex fluids and analytes therein are provided below. Due to steric crowding around the phenyl ring, hexasubstituted benzenes may exhibit a locked conformation in which substituents at alternating ring carbon atoms are directed toward opposite faces of the phenyl ring. For purposes of the present disclosure, a locked conformation also includes the case wherein a rotational barrier is substantially high in energy that the population of molecules with a conformation outside the locked conformation is insignificant, such as in the hexasubstituted benzenes disclosed herein. Hexasubstituted benzene intermediates disclosed herein may exhibit such a locked conformation and preserve the locked conformation upon undergoing further reaction to incorporate various types of entities, such as those comprising a sensing functionality, other types of entities selected to promote sensing of an analyte of interest, and/or entities to promote bonding to a surface.

When the hexasubstituted benzenes are functionalized in the manner disclosed herein, the locked conformation may dispose orthogonal reactive functionality toward opposing faces of the phenyl ring, with one group of reactive functionalities being capable of promoting covalent bonding to a surface and another group of reactive functionalities being directed toward the opposite face of the phenyl ring, which may be further functionalized with entities suitable for promoting sensing of one or more analytes of interest and/or for otherwise modifying the properties of a surface. The term "orthogonal" refers to the condition of two groups of reactive functionalities having different modes of reactivity, such that the two groups of reactive functionalities may be functionalized differently. The reactive functionalities directed away from the surface may become functionalized with various sensing functionalities capable of undergoing molecular association with at least one analyte of interest to promote detection thereof. Particularly suitable examples of such sensing functionalities may be introduced through a reaction of one or more nucleophiles with a hexasubstituted benzene. As such, once the hexasubstituted benzenes have become attached to a surface, the sensing functionalities may be directed outwardly from the surface in a conformationally controlled manner facilitated by the regular atomic arrangement afforded by the phenyl ring, as discussed further herein. Sensing functionalities may be appended to the phenyl ring prior to the hexasubstituted benzene becoming surface bound, or the sensing functionalities may be introduced after surface bonding of the hexasubstituted benzene has taken place.

More specifically, each group of reactive functionalities is located upon alternating ring carbon atoms of the hexasubstituted benzenes of the present disclosure in order to accomplish the foregoing. Thus, three surface-reactive functionalities (or points of surface attachment formed therefrom) and three reactive functionalities (or sensing functionalities formed therefrom) may be present on alternating phenyl ring carbon atoms, with the sensing functionalities directed away from the surface once surface bonding has taken place. Advantageously, the hexasubstituted benzenes of the present disclosure are capable of tripodal covalent bonding to a surface, although fewer points of covalent bonding attachment may be possible in some instances. Similarly, up to three sensing functionalities capable of directly or indirectly promoting sensing of an analyte of interest may extend from the phenyl ring away from the surface.

Advantageously, various surface-reactive functionalities having high surface reactivity may be readily introduced in the hexasubstituted benzenes of the present disclosure in order to promote facile tripodal covalent bonding. When tripodal covalent bonding occurs to a surface, the phenyl ring may orient substantially parallel to the surface, thereby projecting the three sensing functionalities directed toward the opposite face of the phenyl ring outwardly from the surface in an orientationally controlled manner. The outwardly directed sensing functionalities may be the same or different depending on particular application needs. In any event, a dense and regular arrangement of sensing functionalities may be introduced according to the disclosure herein.

Particular variations of hexasubstituted benzenes suitable for sensing applications may include those having a binding group, a reporter group and a buffer group attached and directed toward one face of the hexasubstituted benzene, and having multiple surface-reactive groups preattached and directed toward the opposite face of the hexasubstituted benzene. The buffer group may be present to stabilize the sensor output if a measurable quantity or binding affinity associated with the sensing functionality displays variance with pH for a given analyte. If a buffer group is not present or needed, a second binding group or a second reporter group may be present upon the hexasubstituted benzene, or a functional group that neither aids nor hinders binding or reporting may be present. Another variation may include attachment of a hexasubstituted benzene to a surface with protected functional groups attached to the hexasubstituted benzene and directed toward the face of the hexasubstituted benzene opposite the surface, in which case the protecting groups may be removed and the hexasubstituted benzene further functionalized with sensing functionalities while bound to the surface. Additional variations may incorporate the sensing functionalities without utilizing protected functional groups attached to the hexasubstituted benzene. That is, sensing functionalities may be incorporated upon a surface-bound hexasubstituted benzene by a direct reaction of reactive functionalities opposite the surface with a suitable reagent to form the sensing functionalities.

Multiple hexasubstituted benzenes, each specifically configured to analyze for a particular analyte of interest, may be disposed upon a plate, array or similar arranged/ordered format to facilitate detection of multiple analytes within a complex fluid concurrently or near concurrently. Alternately, individual sensor constructs (i.e., non-arrayed sensors, such as flow-through or dip sensors of various types), each featuring a particular hexasubstituted benzene with a specified sensing functionality, may also be employed in the disclosure herein to analyze for multiple analytes. Non-arrayed sensor constructs may, in non-limiting embodiments, feature the hexasubstituted benzenes bound to a suitable surface, such as upon a support material located within a cartridge, to facilitate analyses. The support material with the hexasubstituted benzene appended thereto may be stockpiled for use when needed, either with the sensing functionalities already attached or with reactive functionalities in place and ready to form sensing functionalities. Non-limiting examples of support materials suitable for housing a hexasubstituted benzene in a cartridge include, for example, polymer macroparticulates, as described in International Patent Application PCT/US2020/041407, filed on Jul. 9, 2020 and incorporated herein by reference in its entirety.

Flow-through sensors incorporating a hexasubstituted benzene of the present disclosure may be particularly desirable to facilitate continuous processing of fluid streams, such as those encountered in the oilfield and other ongoing process applications.

The present disclosure provides facile access to several hexasubstituted benzene intermediates that may serve as in-common synthons for introducing additional functionality thereto and further for bonding the hexasubstituted benzenes to a surface with a controlled orientation of the additional functionality. A wide range of additional functionality may be nucleophilically introduced onto the hexasubstituted benzenes while accomplishing the foregoing, thereby allowing synthesis of a wide range of hexasubstituted benzenes capable of promoting analyte sensing. As discussed in further detail hereinbelow, orthogonal groups of reactive functionalities directed toward each face of the phenyl ring may be transformed in various alternative manners to expand the range of synthetic flexibility offered by the hexasubstituted benzenes described herein.

Various sensing functionalities may be covalently bonded to the hexasubstituted benzenes of the present disclosure before or after the surface-reactive functionalities become covalently bonded to a surface. Choice of whether to covalently bond the sensing functionalities to the hexasubstituted benzenes before or after surface functionalization takes place may depend upon whether the other functionalities interfere with the surface attachment chemistry or the coverage density, for example. When the sensing functionalities are introduced after bonding of the hexasubstituted benzene to a surface, the hexasubstituted benzene may contain suitably protected functionalities that may be subsequently deprotected, possibly sequentially, and reacted to introduce the other functionalities while the hexasubstituted benzene is covalently bound to the surface. Alternately, reactive functionalities in the hexasubstituted benzene may be reacted to introduce the sensing functionalities directly without proceeding through a protected form. In any event a wide range of sensing functionalities may be introduced to a surface in a controlled orientation facilitated by the phenyl ring. In particular examples, surface-reactive functionalities and sensing functionalities may be suitably introduced upon a hexasubstituted benzene nucleophilically in order to accomplish the foregoing, as described in further detail herein. Other techniques for surface attachment and sensing functionality introduction also may be possible using the various hexasubstituted benzenes disclosed herein.

Advantageously, the present disclosure may facilitate the manufacture and testing of custom plates suitable for chemical analyses through automation and/or robotic manipulation afforded by the hexasubstituted benzenes disclosed herein. High-throughput, combinatorial-type sensor fabrication may allow a multitude of sensor constructs to be synthesized and tested quickly for analytical suitability for various analytes in a particular fluid. For example, a plate containing a surface-bound hexasubstituted benzene in each well of the plate may be differentially functionalized with various sensing functionality to determine suitability for a particular analyte. Non-arrayed sensor constructs may similarly comprise a surface functionalized with a hexasubstituted benzene in a form for subsequently introducing sensing functionalities thereto. The hexasubstituted benzenes of the present disclosure may be functionalized in a manner such that ready covalent bonding to a sensor surface takes place with no or minimal effort on the part of an operator. A hexasubstituted benzene bound to a surface may be deposited as a finished sensor construct, as a protected intermediate, or as an unprotected intermediate with reactive functional groups ready to react with a sensing functionality. Suitable surfaces for covalent bonding of the hexasubstituted benzenes thereto are wide-ranging and may include, for example, acrylics, other plastics, glass, metals, ceramic, and the like. The surface may contain suitable functionality for undergoing a chemical reaction to form a covalent bond with a complementary functional group upon the hexasubstituted benzenes. In non-limiting examples, a surface may bear an alkene that may undergo a free radical reaction with an alkene group in the hexasubstituted benzenes or an alkyne group that may undergo a cycloaddition reaction with an azide in the hexasubstituted benzenes. In another example, a surface may bear an electrophile for reaction with a benzylic amine in the hexasubstituted benzenes. Other functional groups may also be suitable for promoting covalent bond formation to a surface, as described in further detail hereinafter. In non-limiting examples, a hexasubstituted benzene may comprise a methacrylate functionality directed toward one face of the hexasubstituted benzene and reactive functionalities or protected amines directed toward the other face, either of which may be transformed into sensing functionalities. Alternately, the active portion of a finished sensor construct may be attached directly to a surface with the sensing functionalities already attached (e.g., a binder group, an optional reporter group such as a dye or chromophore, and a buffer group) and directed toward one face of the hexasubstituted benzenes and a reaction product of the acrylic functionalities bound to a surface and directed toward the opposite face of the hexasubstituted benzene.

Heretofore, the art of preparing high efficiency chemical testing assays from premanufactured plates may take considerable time and skill, and the testing reagents may remain in solution during the analyses. Furthermore, the testing options available from premanufactured plates may be very expensive and limited. The present disclosure may alleviate these difficulties.

Some of the hexasubstituted benzenes described herein may react readily with an appropriately functionalized surface, with little to no user expertise or outside intervention being required to promote covalent bonding to the surface. Because of the synthetic design flexibility offered herein, particularly facilitated through use of in-common synthons with readily manipulated functionality, multiple analyses may be readily facilitated using plates or similar arrays of surface-bound hexasubstituted benzenes, each configured for detecting an analyte of interest within a fluid, possibly containing multiple analytes and/or interfering matrix substances. Reaction and covalent bonding of the hexasubstituted benzenes with a surface may facilitate production of robust flow-through sensors as a non-limiting example, wherein the hexasubstituted benzene may carry functionality both for promoting covalent bonding and facilitating molecular association with an analyte of interest in a desired manner.

Once a sensor construct has been covalently attached to a surface at designated coordinates, such as in an array or similar ordered arrangement upon a surface, electronics may probe the surface with electromagnetic radiation at an appropriate location. The sensor constructs may absorb (absorption spectroscopy) or emit (fluorescence spectroscopy) electromagnetic radiation or chemiluminesce as a result of molecular association with an analyte, where the product of the molecular association is light or other output electromagnetic radiation. As such, the present disclosure may alleviate the limitations associated with solution-based testing wherein the reagents are part of the solution instead of attached to a surface, as may be facilitated with the hexasubstituted benzenes of the present disclosure. Loading of the testing reagents in a solution may be laborious, including manipulations during testing, and significantly complicate conventional plate-based analyses. Alternately, electronics may be used to detect changes in electrical current or electrical potential for some types of sensors. In addition, the present disclosure may also allow for very precise use of small electronics to probe a surface at a designated location for sensing functionalities built on the hexasubstituted benzene platform. As such, very dense arrays of sensor constructs may be fabricated for high-throughput testing.

Before describing sensing methods of the present disclosure in greater detail, hexasubstituted benzenes suitable for use therein will be further described. Access to hexasubstituted benzene in-common synthons suitable for conducting further synthetic transformations thereon to introduce one or more sensing functionalities thereon may be realized through a series of chemical reactions outlined in Scheme 1 below. The alternating facial disposition of the substituents upon the phenyl ring is denoted by bolded and dashed bonds in the structures below. It is to be understood that when any hexasubstituted benzene structure herein lacks bolded or dashed bonds, all possible diastereomers of the structure are implicitly described.

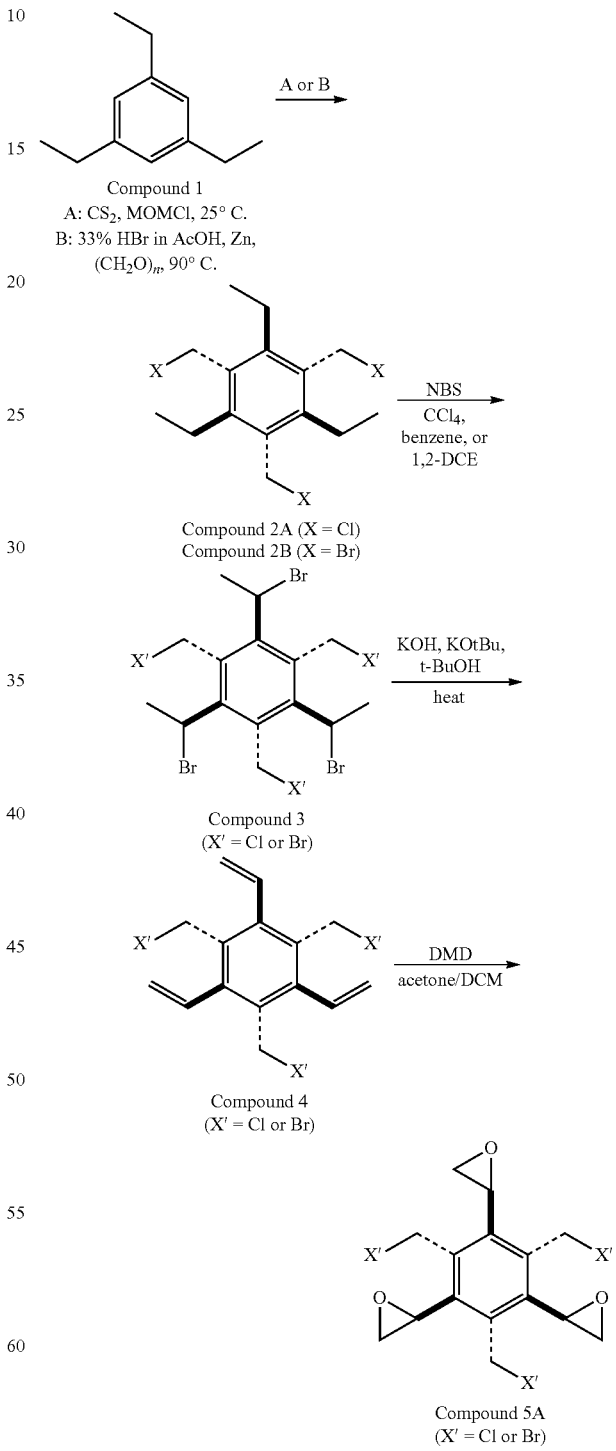

Scheme 1

Referring to Scheme 1, 1,3,5-triethylbenzene (Compound 1) may be purchased commercially or synthesized by forming a thermodynamic Friedel-Crafts alkylation product. The remaining ring carbon atoms in Compound 1 may then be halomethylated using either chloromethyl methyl ether (MOMCl)/CS$_2$ (Conditions A) or HBr/Zn/paraformaldehyde (Conditions B) to afford either Compound 2A or 2B, as described in Wallace, et al., "Preparation of 1,3,5-Tris(aminomethyl)-2,4,6-triethylbenzene from Two Versatile 1,3,5-Tri(halosubstituted) 2,4,6-Triethylbenzene Derivatives," Synthesis, 2005, pp. 2080-2083. Compound 2A or Compound 2B may then be brominated at the α-position of the ethyl group using N-bromosuccinimide (NBS) to form Compound 3. If Compound 2A is brominated with NBS, some or all of the chlorides may exchange for bromides, particularly if a sufficient excess NBS is used. A mixture of benzylic halides in Compound 3 and in subsequent products, if formed, may be used satisfactorily to conduct the further synthetic transformations shown in Scheme 1 and in additional schemes discussed below. Alternately, elemental bromine may be used as the bromide source for conducting the bromination reaction. Other radical initiators, such as benzoyl peroxide, or electromagnetic radiation in the visible or ultraviolet region of the electromagnetic spectrum may also be used for initiating the bromination reaction, with the choice of electromagnetic radiation wavelength being chosen based upon the bromide source and the substrate undergoing bromination. Still other suitable bromination conditions may include those utilizing carbon tetrabromide, an electromagnetic radiation source, an absorption species, and/or a radical promoter. Morpholine and many tertiary amines may serve as a suitable radical promoter in this reaction.

Referring still to Scheme 1, the α-bromoethyl groups in Compound 3 may undergo dehydrobromination in the presence of a hindered tertiary amine, potassium t-butoxide or a similar base to form the corresponding vinyl groups in Compound 4. In some instances, a phase transfer catalyst, such as a crown ether or a tetraalkylammonium salt may be used to promote this reaction in an organic solvent such as dichloromethane, tetrahydrofuran or t-butanol. Finally, the vinyl groups of Compound 4 may be epoxidized using potassium peroxymonosulfate (OXONE), dimethyldioxirane (DMD), a peracid (e.g., MCPBA) or similar oxidants capable of selectively epoxidizing alkenes to afford Compound 5A. Compound 5A may serve as a versatile in-common synthon for accessing additional hexasubstituted benzenes disclosed herein. Other hexasubstituted benzene compounds shown in Scheme 1 may also constitute versatile synthons for promoting a reaction with a surface, as discussed further herein.

In some instances, incomplete dehydrobromination may occur in forming Compound 4, in which case a mixture comprising Compounds 4, 4A and 4B may be obtained, along with unreacted Compound 3, as shown in Scheme 1A.

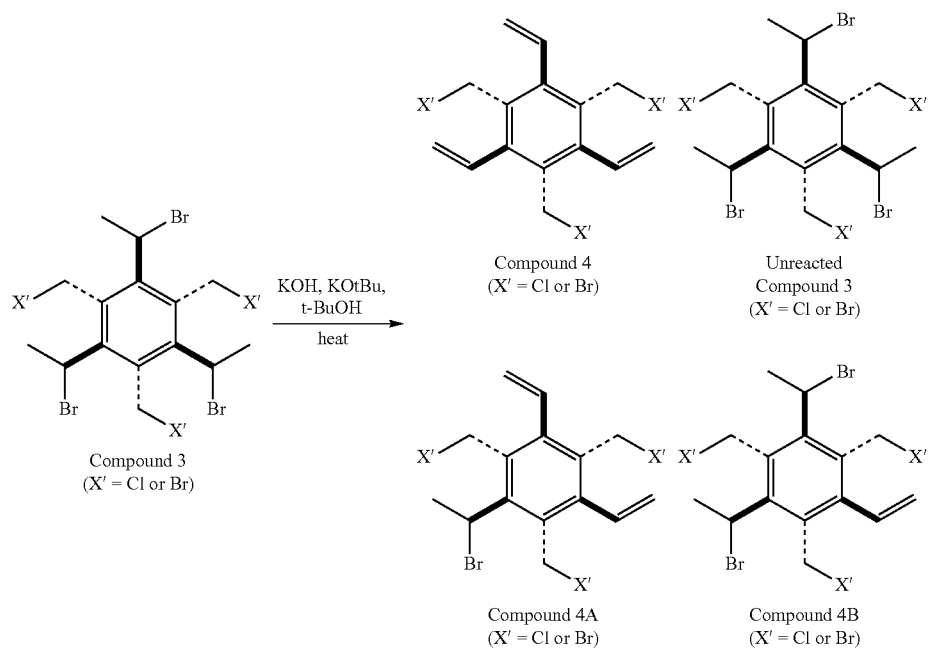

This mixture of compounds may still undergo epoxidation (for compounds containing vinyl groups), which may then afford further functionalized compounds containing one, two or three additional substituents prepared through epoxide ring opening, as discussed further below. When starting with a mixture of this type, the functionalized products bearing different numbers and/or types of further substituents may be easily separable from one another. If less than three substituents are bonded to the hexasubstituted benzene following epoxide ring opening, the substituents that are present may at least bind or interact with an analyte of interest and provide a suitable spectroscopic signature for determining the quantity of analyte present. When only one epoxide group is formed and subsequently opened, the incorporated functionality may both bond or interact with the analyte and afford a suitable spectroscopic signature for assaying the analyte. When two epoxide groups are present, these functions may be present in different incorporated functionalities.

Although benzylic halides are generally considered to be very good leaving groups, the benzylic halides in the hexasubstituted benzenes of the present disclosure are surprisingly low in reactivity with all but select nucleophiles. Without being bound by any theory or mechanism, it is believed that the particular orientation of the halomethyl groups with respect to the phenyl ring may limit their ability to undergo backside attack by many types of nucleophiles. Since the benzylic carbon is displaced from the plane of the phenyl ring, conjugation of a benzylic carbocation with the pi (π) bonds of the aromatic ring is also not possible. Similarly, the steric interactions around the ring are believed to force the vinyl groups to break conjugation with the pi (π) bonds of the aromatic ring. This permits an unexpected vinyl group stabilization to be realized compared with typical vinylbenzenes, such as styrene, which often polymerize readily under mild conditions. Although the benzylic halides are surprisingly low in reactivity, the low reactivity advantageously facilitates the synthetic transformations of the ethyl groups to form epoxides, as shown in Scheme 1 above.

Certain nucleophiles may undergo a facile reaction with the benzylic halides in the hexasubstituted benzenes disclosed herein. In particular, azide nucleophiles may undergo a high-yield reaction with the benzylic halides to form the corresponding benzylic azides. The benzylic azides may be further transformed to a benzylic amine, if desired, or undergo a direct dipolar cycloaddition reaction to form a 1,2,3-triazole that may facilitate use of the hexasubstituted benzenes in various applications. Functionalization of the benzylic amine or benzylic azide may promote attachment of the hexasubstituted benzenes to a surface, as discussed further hereinbelow. Alternately, surface attachment may be promoted through the vinyl groups, and the benzylic amines or benzylic halides may be further functionalized into groups tailored to suit a particular application, such as for promoting analyte sensing.

Surprisingly, an azide nucleophile may react with the benzylic halides without promoting nucleophilic opening of the epoxides in particular hexasubstituted benzene compounds of the present disclosure. Specifically, as shown in Scheme 2 below, Compound 5A may be reacted with sodium azide to form Compound 5B, which bears intact epoxides in combination with the benzylic azides. Like Compound 5A, Compound 5B may also serve as a versatile in-common synthon for forming additional hexasubstituted benzenes disclosed herein, including hexasubstituted benzenes functionalized to promote detection of an analyte and/or suitable for attachment to an appropriate surface. Further details concerning introduction of the azide groups at a later synthetic stage and additional transformations of the azide groups are discussed in more detail below. Epoxidized variants of Compounds 4A and 4B may be reacted similarly to introduce three azide groups thereto.

Scheme 2

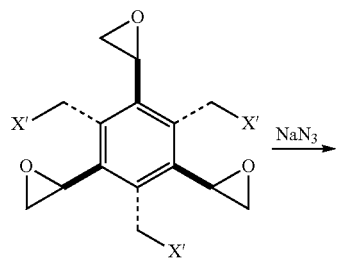

Compound 5A
(X' = Cl or Br)

-continued

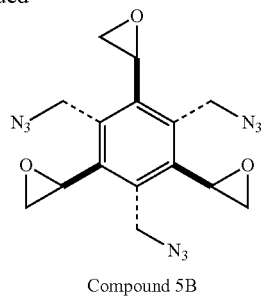

Compound 5B

In another example, Compound 3 may be transformed into Compound 3A, as shown in Scheme 2A, by reacting the secondary benzylic bromides with sodium azide.

Scheme 2A

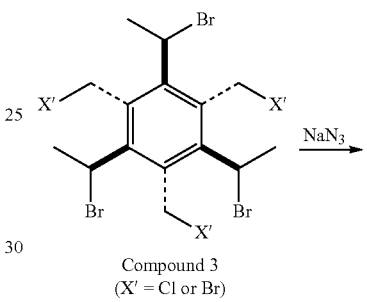

Compound 3
(X' = Cl or Br)

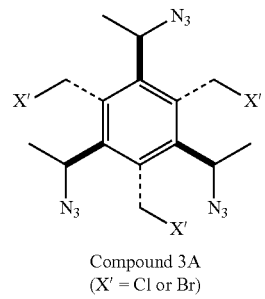

Compound 3A
(X' = Cl or Br)

Without being bound by theory or mechanism, it is believed that the secondary benzylic halide may react faster with sodium azide than does the primary benzylic halide. Thus, chemoselectivity may be achieved, particularly when X' is Cl and the secondary benzylic halide is Br. Compound 3A is also a useful synthetic intermediate, which may undergo a similar sequence of reactions to those discussed below. As a non-limiting example, the secondary azide groups may undergo a reaction to promote surface attachment (e.g., through undergoing a cycloaddition reaction or reduction to form an amine group), and the primary benzylic halides may thereafter undergo nucleophilic displacement with azide to form primary benzylic azides that themselves may be further modified synthetically to introduce one or more sensing functionalities or related moieties. For example, the primary benzylic azides may be reduced to primary amines, which may then be alkylated or acylated in non-limiting examples to modify the properties of a surface or to introduce one or more sensing functionalities for an analyte of interest.

In still another example, Compound 4 may undergo hydrosilylation to introduce a trialkylsilyl group and form Compound 4C, as shown in Scheme 2B.

Scheme 2B

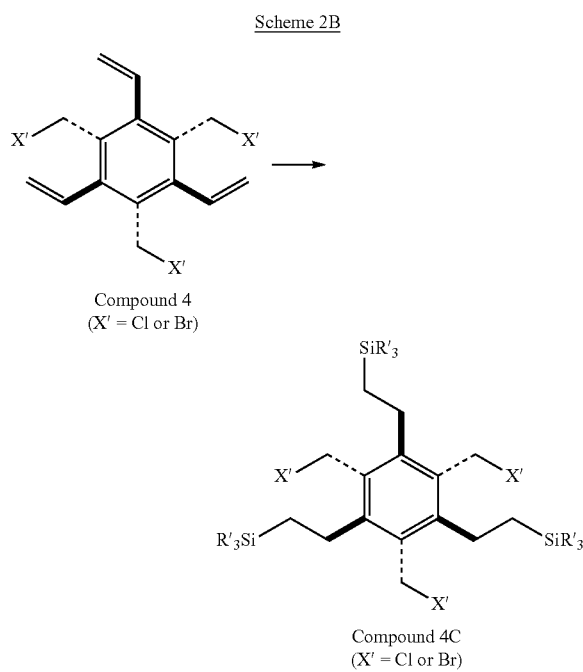

Compound 4
(X' = Cl or Br)

Compound 4C is also a useful synthetic intermediate, which may undergo a similar sequence of reactions to those discussed below. As a non-limiting example, the primary benzylic halides in Compound 4C may undergo nucleophilic displacement with azide to form primary benzylic azide groups, which may then undergo a further reaction to promote surface attachment in various ways.

In still another example, Compound 4 may undergo a reaction with azide to form the corresponding primary benzylic azides in Compound 4D, as shown in Scheme 2C.

Scheme 2C

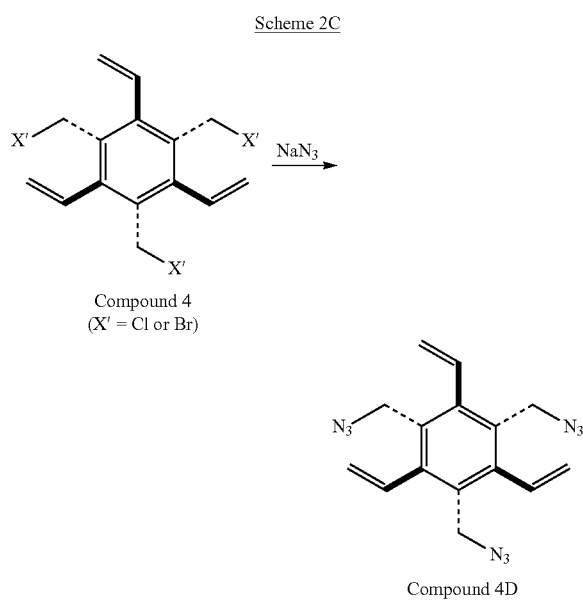

Compound 4
(X' = Cl or Br)

NaN₃

Compound 4D

The benzylic azides may then undergo a cycloaddition reaction to form a covalent bond to a surface, or the benzylic azides may undergo reduction to form benzylic amines, which may then be reacted to form a covalent bond to the surface. The vinyl group may project away from the surface and provide a handle for introducing one or more sensing functionalities or other groups capable of modifying a surface in a desired way. In one example, the vinyl groups may be epoxidized in order to introduce a sensing functionality or similar group through nucleophilic opening of the epoxides. In non-limiting examples, the vinyl groups may be oxidized to form a diol or primary alcohol or undergo oxidative cleavage to form a 1,3,5-substituted benzenetricarboxylic acid, any of which may be further functionalized to introduce a sensing functionality through covalent bond formation. In another synthetic approach, the vinyl groups may be reacted with an alkene to produce olefin dimers or higher oligomers.

In still another synthetic approach, the vinyl groups of Compound 4 may be reduced to the corresponding ethyl group, and azides may be introduced as in Scheme 2C. After subsequent reduction, the resulting amine groups may be utilized to introduce functionality suitable for promoting binding and/or analysis of an analyte of interest, particularly if binding of the hexasubstituted benzene to a surface need not take place.

Accordingly, various embodiments of the present disclosure provide hexasubstituted benzenes having a structure corresponding to Compound 6 below,

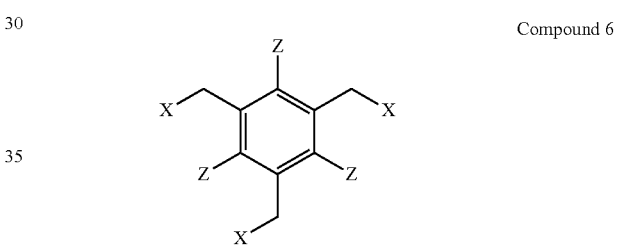

Compound 6 wherein each X is independently Cl, Br or N₃, and each Z is independently —CH(Br)CH₃, —CH(N₃)CH₃, —CH=CH₂, —CH₂CH₃, —CH₂CH₂SiR₃, or epoxide, wherein R' is a hydrocarbyl group, such as a $C_1$-$C_{10}$ alkyl group. In more specific embodiments, each X is independently Cl, Br or N₃, and each Z is independently —CH(Br)CH₃, —CH=CH₂, or epoxide. Compound 6 may be a particular diastereomer, in which groups extending from alternating aromatic ring positions are directed toward opposing faces of the benzene ring. Variants of Compound 6 may be further functionalized to introduce sensing functionalities and/or points of surface attachment, as discussed hereinbelow.

In more particular embodiments, the hexasubstituted benzenes described herein may correspond to Compound 3, in which each Z is —CH(Br)CH₃ and each X is Br or each X is Cl. In other more particular embodiments, the hexasubstituted benzenes described herein may correspond to Compound 4, in which each Z is —CH=CH₂ and X is Br or each X is Cl. In still other more particular embodiments, the hexasubstituted benzenes described herein may correspond to Compound 5A, in which each Z is epoxide and each X is Br or each X is Cl. In yet still other more particular embodiments, the hexasubstituted benzenes described herein may correspond to Compound 5B, in which each Z is epoxide and each X is N₃. As referenced above, Compounds 5A and 5B may be particularly versatile in-common synthons for producing additional hexasubstituted benzenes disclosed herein, as described in further detail below.

Other particular examples of Compound 6 include those wherein each X and Z are selected as above, but each Z is not necessarily the same. Mixtures of such variants of Compound 6 are also encompassed by the disclosure herein.

duce further functionality to the hexasubstituted benzenes, as discussed further in reference to Scheme 3. As shown in Scheme 3 below, the epoxides in Compound 5A may be further reacted with one or more nucleophiles (Nu:) to promote epoxide ring opening without disturbing the benzylic halides, thereby forming Compound 7. Suitable nucleophiles may include nitrogen nucleophiles such

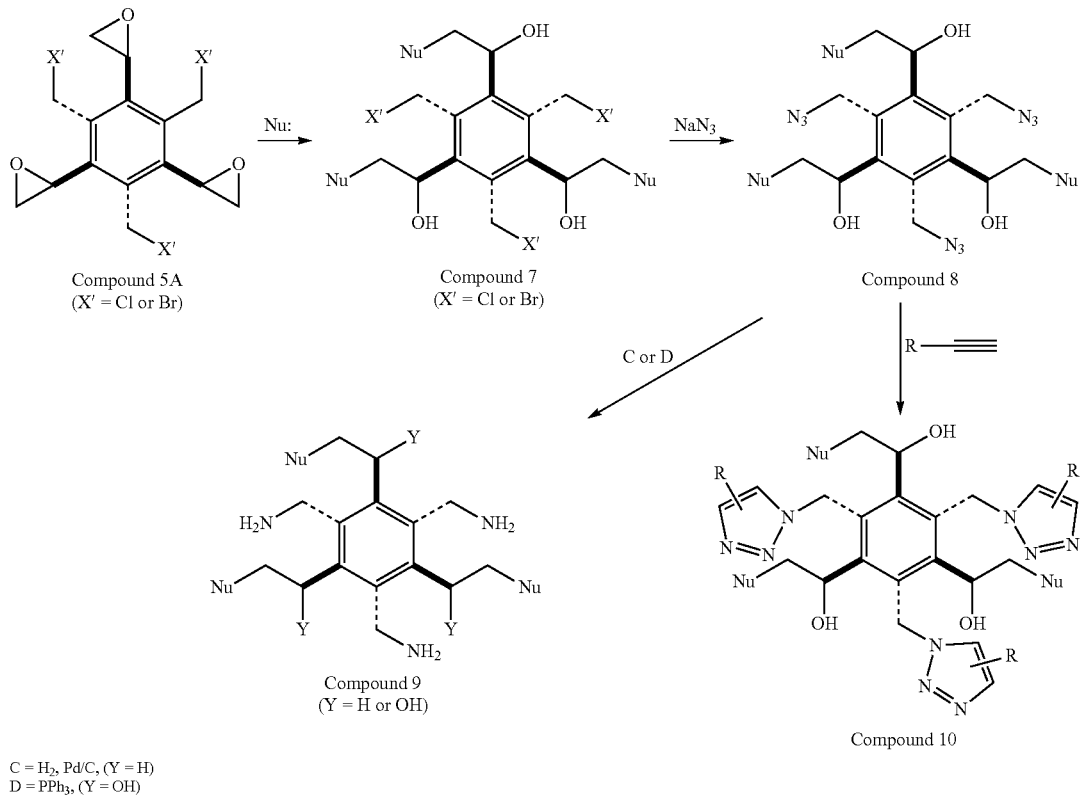

Scheme 3

Illustrative mixtures may include those in which Z is a mixture of —CH(Br)CH$_3$ and —CH=CH$_2$, or —CH=CH$_2$ and epoxide.

As discussed above, Compounds 3-5A/B and similar hexasubstituted benzenes may bear two groups of orthogonal reactive functionality directed toward opposite faces of the phenyl ring at alternating ring carbon atoms. Therefore, Compounds 3-5A/B and similar hexasubstituted benzenes may exist as stereoisomers. Thus, in Compound 3, for example, the benzylic halides are directed toward one face of the phenyl ring and the α-bromoethyl groups are directed toward the opposite face of the phenyl ring. Similarly, in Compounds 5A and 5B, the benzylic halides or benzylic azides, respectively, are directed toward one face of the phenyl ring and the epoxide groups are directed toward the opposite face of the phenyl ring. The groups of orthogonal reactive functionality directed toward opposing faces of the phenyl ring may be exploited to introduce further functionality in an orientationally controlled manner, particularly to promote analyte sensing, as discussed hereinafter.

Compound 5A has three epoxides directed toward one face of the phenyl ring and three benzylic halides directed toward the opposite face of the phenyl ring. Each group of reactive functionalities may be reacted separately to introas primary or secondary amines. According to various embodiments of the present disclosure, the one or more nucleophiles may bear functionality configured to promote sensing of an analyte of interest or for other modifying a surface in a desired way. Particular examples may include the one or more nucleophiles featuring a spectroscopically active entity, one or more nucleophiles featuring an entity capable of undergoing molecular association with an analyte of interest, and/or one or more nucleophiles capable of promoting a desired chemical environment to promote sensing, such as through providing a buffering moiety. After epoxide ring opening has taken place, the benzylic halides may then undergo a reaction with sodium azide to form the corresponding benzylic azides (Compound 8). The benzylic azides may then undergo reduction to an amine to form Compound 9 or undergo dipolar cycloaddition with an alkyne (R—C≡CH, R is a hydrocarbyl group, such as a $C_1$-$C_{10}$ alkyl group or any aryl group) to form Compound 10 to introduce further functionality onto the phenyl rings. The resulting 1,2,3-triazole in Compound 10 may promote bonding to a surface, as discussed in further detail below. Mono- or bis-epoxides, prepared by epoxidizing Compounds 4B or 4A, respectively, may undergo a similar series of reactions.

Referring still to Scheme 3, the nucleophile that promotes epoxide ring opening may become appended at the β-position with respect to the phenyl ring, thereby placing a hydroxyl group at the α-position, as shown in Compound 7. Without being bound by any theory or mechanism, the presence of the α-hydroxyl groups may enhance microenvironment solubility in proximity to the phenyl ring to promote enhanced binding once surface bound. The other regioisomer may form to a limited extent in some cases to introduce the hydroxyl group at the β-position and the nucleophile at the α-position. Although Scheme 3 has shown a single nucleophile opening each epoxide, it is to be recognized that multiple nucleophiles may be used, in which case statistical opening of the epoxides with the various nucleophiles may occur to form a range of products, provided that the multiple nucleophiles exhibit a comparable rate of reaction during epoxide ring opening. Thus, in some embodiments of the present disclosure, a first epoxide may be opened with a first nucleophile, a second epoxide may be opened with a second nucleophile, and a third epoxide may be opened with a third nucleophile, in which the first, second and third nucleophiles are all different. If formed and if needed, product mixtures may be separated by a suitable laboratory separation technique such as column chromatography, crystallization, or the like. Optionally, the α-hydroxyl group may be removed by reduction prior to displacing the benzylic halides (not shown in Scheme 3). Still other strategies may react the epoxides with orthogonally protected nucleophiles which may be deprotected at a later time for sequential attachment of functionalities suitable to promote sensing of a desired analyte. As a non-limiting example, two or more protected amines may comprise Nu: in Scheme 3 above (e.g., any combination of BOC, imide, FMOC or sulfonamide groups, as non-limiting examples), which may be individually deprotected and further functionalized to introduce sensing functionalities.

Referring still further to Scheme 3, the benzylic azides in Compound 8 may be further manipulated to introduce additional functionality upon the hexasubstituted benzene (i.e., directed toward the face of the phenyl ring opposite the ring-opened epoxides). In some embodiments, the benzylic azides may be reduced to a benzylic amine to form Compound 9, such as through Staudinger reduction with triphenylphosphine or catalytically using hydrogen and a Pd/C catalyst. Catalytic reduction of the azides using hydrogen and Pd/C may concurrently reduce the α-hydroxyl group to form the corresponding methylene compound. Staudinger reduction, in contrast, may leave the α-hydroxyl group intact. In other embodiments, the azides may undergo a 1,3-dipolar cycloaddition reaction with a terminal alkyne to form the corresponding 1,2,3-triazole, as shown for Compound 10. The benzylic amine or the 1,2,3-triazole may be further exploited to promote surface attachment, as discussed further hereinbelow. Alternately, the benzylic amines may undergo a reaction to introduce a functionality capable of sensing or binding an analyte of interest. In addition or alternately, the α-hydroxyl groups may be further manipulated, such as under Mitsunobu conditions (triphenylphosphine, diethylazodicarboxylate (DEAD)) to introduce a nucleophile at the α-position, such as a carboxylic acid ester, an azide, an imide, an aryl ether, or a sulfonamide. Should removal of the α-hydroxyl groups be desired, the carboxylic acid ester may be reduced with a hydride reagent to affect removal.

Similar to the discussion for Compound 5A, Compound 5B has three epoxides directed toward one face of the phenyl ring and three benzylic azides directed toward the opposite face of the phenyl ring. Each group of reactive functionalities may be reacted separately to introduce further functionality to the hexasubstituted benzenes, as discussed in reference to Scheme 4 below.

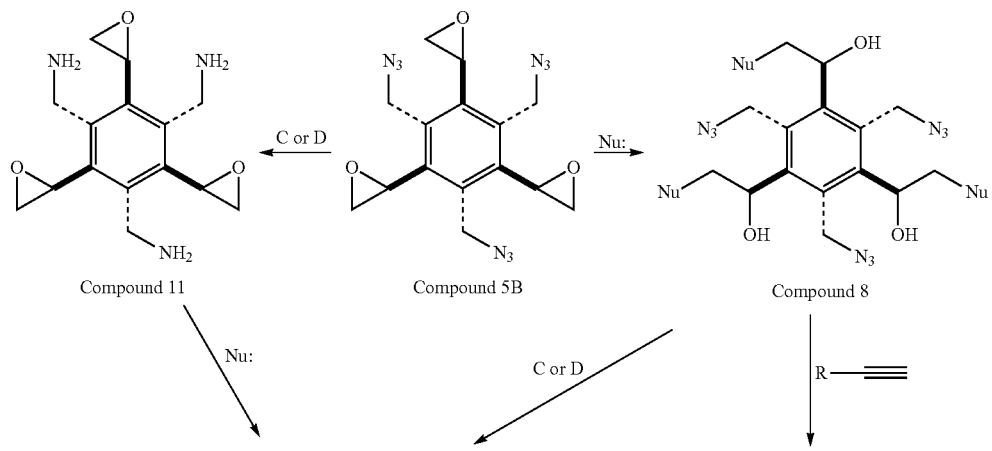

Scheme 4

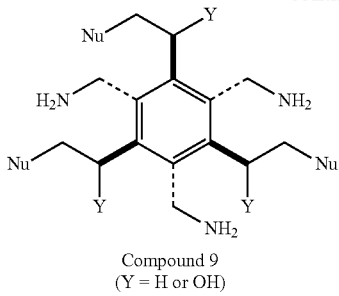

Compound 9
(Y = H or OH)

C = H₂, Pd/C
D = PPh₃

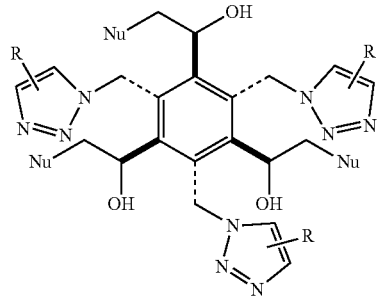

Compound 10

As shown in Scheme 4, the epoxide rings in Compound 5B may be opened with a nucleophile without disturbing the benzylic azides to form Compound 8, the same intermediate formed in Scheme 3 above. The benzylic azides of Compound 8, in turn, may be transformed in a similar manner to that described above in reference to Scheme 3 to form Compound 9 or Compound 10. Alternately, the benzylic azides may be reduced to the corresponding benzylic amines without disturbing the epoxides, thereby forming Compound 11. The epoxides in Compound 11, in turn, may then undergo nucleophilic opening to afford Compound 9, wherein the amine groups may be optionally further transformed into a functional group capable of promoting binding or analysis of an analyte of interest. Thus, depending on particular synthetic needs, the order of epoxide ring opening and benzylic halide displacement may be reversed. As with Scheme 3 above, a first epoxide in Scheme 4 may be opened with a first nucleophile, a second epoxide may be opened with a second nucleophile, and a third epoxide may be opened with a third nucleophile, in which the first, second and third nucleophiles are the same or all different. Product mixtures may be resolved by a suitable laboratory separation technique. Mono- or bis-epoxides, prepared by epoxidizing Compounds 4B or 4A, respectively, may undergo a similar series of reactions.

Accordingly, various embodiments of the present disclosure provide hexasubstituted benzenes having a structure of Compound 12 below, Compound 12

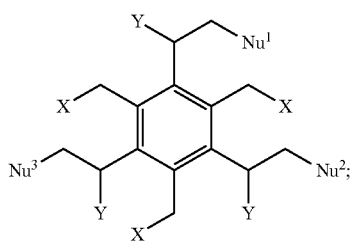

wherein $Nu^1$, $Nu^2$ and $Nu^3$ are each nucleophiles, each X is independently Cl, Br, $N_3$, $NH_2$, or NHQ, and each Y is independently H or OH. Q is an alkyl, aryl or polyether, optionally bound to the nitrogen atom via a carbonyl group. Q may bear further functionality for binding or interacting with an analyte of interest.

In more particular embodiments, $Nu^1$, $Nu^2$ and $Nu^3$ are each different. As used herein with respect to the nucleophiles, the term "different" refers to $Nu^1$, $Nu^2$ and $Nu^3$ differing structurally from one another, either compositionally or isomerically. $Nu^1$, $Nu^2$ and $Nu^3$ may each be of the same class of nucleophile or different. Illustrative classes of nucleophiles that may be suitable for use in epoxide ring opening according to the disclosure herein include, for example, nitrogen nucleophiles, such as primary or secondary amines. Phosphines, thiols, selenols, selenides, diselenides, alkoxides, carboxylates, and/or carbanions may also be suitable nucleophiles. In an illustrative embodiment, $Nu^1$, $Nu^2$ and $Nu^3$ may comprise orthogonally protected amines, such as amines protected with any combination of BOC, imide, FMOC or sulfonamide groups. For example, when $Nu^1$, $Nu^2$ and $Nu^3$ are amines orthogonally protected with BOC, phthalimide and a sulfonamide, respectively, the amine corresponding to $Nu^1$ may be exposed with dilute acid, the amine corresponding to $Nu^2$ may be exposed with dilute base, and amine corresponding to $Nu^3$ may carry a suitable sensing functionality upon the sulfonamide hydrocarbyl group. Other combinations of orthogonal protecting groups for amines may also be suitable, as can be appreciated by one having ordinary skill in the art. For instance, in another non-limiting example, $Nu^1$, $Nu^2$ and $Nu^3$ may be amines that are orthogonally protected with BOC, FMOC or phthalimide, or CBZ to allow the amines to be exposed through staged exposure to acid, base, and reducing conditions (e.g., catalytic hydrogenolysis), respectively. Such strategies may allow the amines to be sequentially exposed and reacted with a sensing functionality, including any combination of a binder group, a report group (e.g., a spectroscopically active functionality) and/or a buffering group to promote sensing under various conditions. Sequential introduction of other types of functionalities may be realized similarly.

According to more particular embodiments, each X in Compound 12 may be Br or each X may be Cl. Alternately, each Br or Cl may be displaced with azide, such that each X in Compound 12 is $N_3$. In still other embodiments, each azide in Compound 12 may be reduced to form a benzylic amine, such that each X in Compound 12 is $NH_2$ and Y is either H or OH depending on how the reduction is performed, as discussed above. For example, catalytic reduction of the benzylic azide may reduce the benzylic alcohol to a methylene group, whereas triphenylphosphine reduction (Staudinger reduction) of the benzylic azide may leave the benzylic alcohol intact.

As referenced in brief above, the present disclosure also provides surface-bound reaction products of the hexasubstituted benzenes disclosed herein. Specifically, the group of reactive functionalities directed toward one face of the phenyl ring may undergo reaction with suitable functional groups upon a surface to result in up to tripodal covalent bonding of the hexasubstituted benzene to the surface. Less than tripodal covalent bonding of the hexasubstituted benzenes to a surface is also possible if not all of the reactive functionalities undergo a reaction. The remaining group of reactive functionalities directed toward the opposite face of the phenyl ring face, away from the surface, may be reacted to form other types of functional groups to promote sensing, as discussed above. For example, according to some embodiments, the reactive functionalities facing away from the surface may be reacted with one or more nucleophiles (e.g., nitrogen nucleophiles) to affix one or more desired sensing functionalities upon the surface in a fixed orientation. Up to three sensing functionalities may be directed toward one face of the phenyl ring located opposite the location of surface attachment. Advantageously, either of the groups of reactive functionalities in Compounds 5A or 5B may be suitably reacted with a surface to afford various sensor constructs comprising the surface-bound hexasubstituted benzenes disclosed herein. The choice of which group of reactive functionalities to react with the surface may be dictated by the type of surface and the type of surface functionalities that are present. Illustrative approaches for forming such surface-bound hexasubstituted benzenes are discussed hereinafter.

Some embodiments of the present disclosure may include a reaction product of a hexasubstituted benzene that may be covalently bonded to a surface. The hexasubstituted benzene, before being covalently bonded to the surface, may have a structure corresponding to Compound 13

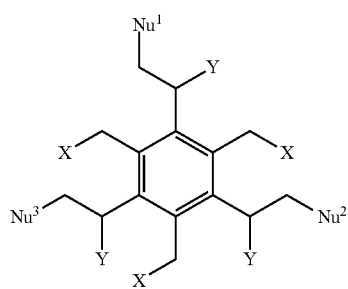

Compound 13 wherein $Nu^1$, $Nu^2$ and $Nu^3$ are each nucleophiles that may be the same or different, each X is Cl, Br, $N_3$ or $NH_2$, particularly each X is $N_3$ or $NH_2$, and each Y is independently H or OH. In forming a surface-bound hexasubstituted benzene, each $N_3$ or $NH_2$ may be reacted to form a linking group as a reaction product that is covalently bonded to a surface, as shown in Compound 14 below.

In some or other embodiments, surface-bound hexasubstituted benzenes disclosed herein may comprise a surface, and a reaction product of the surface and a hexasubstituted benzene covalently bonded to the surface, specifically a hexasubstituted benzene bearing an amine or an azide, in which the reaction product has a structure represented by Compound 14

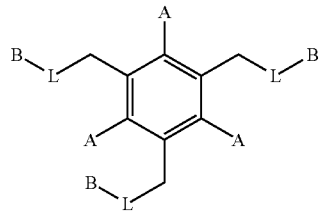

Compound 14 wherein B is a surface, each A is a vinyl group, a reaction product of a vinyl group, an epoxide or a reaction product formed from opening of an epoxide with a nucleophile, and each L is a linking group connecting a benzylic carbon of the hexasubstituted benzene to the surface. Each linking group L is formed from an azide or an amine bonded to the benzylic carbon, specifically a reaction product formed between a functionality upon the surface and the azide or amine located upon the benzylic carbon. As such, each linking group L may comprise a reaction product of the azide or the amine, according to various embodiments of the present disclosure.

Surfaces that may undergo covalent functionalization with the hexasubstituted benzenes disclosed herein are not considered to be particularly limited. In illustrative embodiments, suitable surfaces may be selected from a polymer surface, a metal surface, a ceramic surface, a glass surface, and any combination thereof. The type of surface undergoing functionalization and the surface functional groups thereon may dictate the type of linking group that is chosen for covalently bonding the hexasubstituted benzene to the surface. Particular examples are discussed hereinafter. Particular examples of surface functionalization may include the use of materials suitable for being exposed to lateral flow when conducting analyses. This type of surface functionalization, regardless of the underlying surface material (substrate), may depend upon antibody chemistry or other selective binding group for an analyte of interest. Hexasubstituted benzenes of the present disclosure are particularly suited for the preparation of lateral flow assays with high selectivity and geometric placement of chemistries upon a surface to selectively detect and signal the presence of various analytes.

Suitable linking groups L formed from a benzylic azide may comprise a 1,2,3-triazole or similar cycloaddition reaction product of the benzylic azide. Such linking groups may be formed by reacting the benzylic azide with a surface-bound terminal alkyne in a dipolar cycloaddition reaction. Thus, according to some embodiments, sensor constructs of the present disclosure may comprise modified surfaces may have structures corresponding to Compounds 15 and 16 shown in Scheme 5 below. Although Scheme 5 has shown Compounds 15 and 16 being accessed via Compound 5B, it is to be appreciated that Compound 16 may be similarly accessed via Compound 5A (see Scheme 3). Surface-bound terminal alkynes may be directly appended to the surface undergoing functionalization or be spaced apart therefrom by a grouping of one or more atoms connected to the surface. Thus, 1,2,3-triazole linking groups need not necessarily exhibit direct bonding to the surface in the manner depicted in Scheme 5. In illustrative embodiments, suitable surface-bound terminal alkynes may be present as a polymer side chain, or as appended surface functionalization upon a glass, metal, ceramic or similar type of surface. Compound 15 represents a versatile precursor for synthesizing various sensor constructs having a range of sensing functionalities. Compound 16, in contrast, may represent a fully functionalized sensor construct (Nu is selected to promote sensing of an analyte) or a protected intermediate that may be converted into a functional sensor construct (Nu introduces a protected functional group that may be deprotected and further functionalized to provide a sensing functionality).

Scheme 5

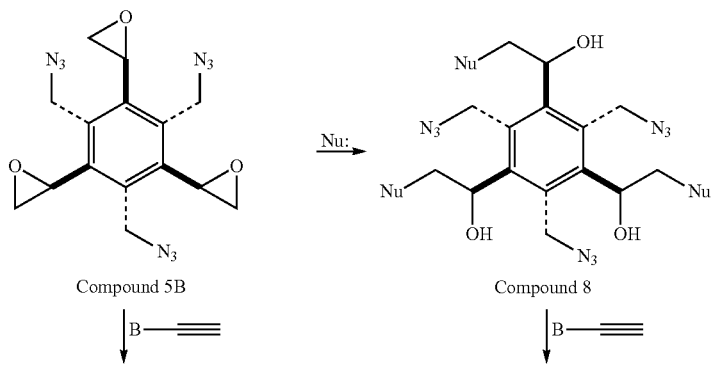

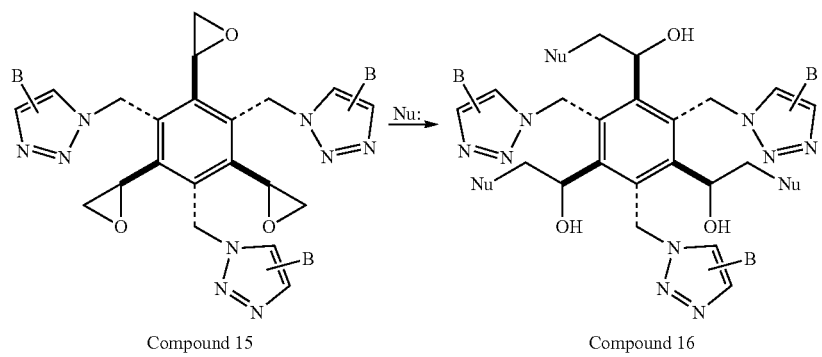

Suitable linking groups L formed from a benzylic amine may incorporate the benzylic amine in a grouping of atoms extending between the benzylic carbon and a surface undergoing covalent functionalization with the hexasubstituted benzenes. Such linking groups may be formed by reacting the benzylic amine with an amine-reactive functionality already covalently bonded to the surface, or by first reacting the benzylic amine with a grouping of atoms containing further functionality that is reactive with one or more functional groups present upon the surface and then reacting the functionalized benzylic amine with the surface in a separate synthetic step. In either case, reaction of the benzylic amines to form linking groups may take place before or after epoxide opening, as shown in Schemes 6 and 7 below. Linking groups L formed from a primary benzylic amine may comprise a secondary or tertiary benzylic amine reaction product or a secondary or tertiary amide reaction product in non-limiting examples. Like Compound 15 above, Compound 20 in Scheme 7 is a versatile synthetic intermediate for introducing a range of sensing functionality thereto.

Scheme 6
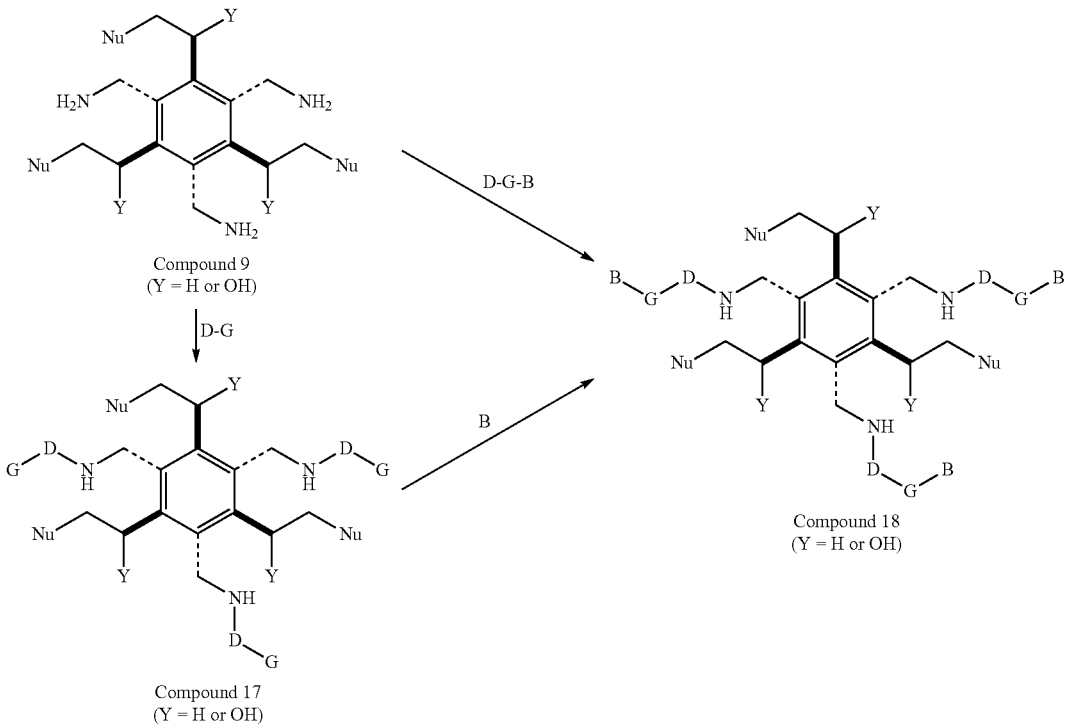
Scheme 7
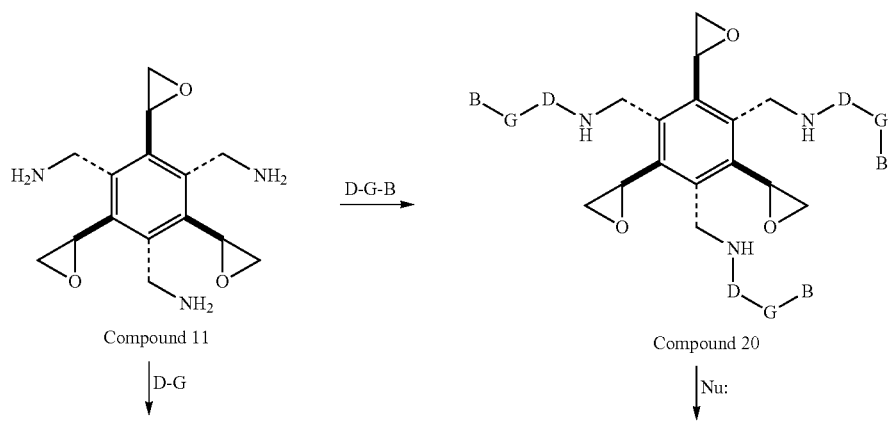

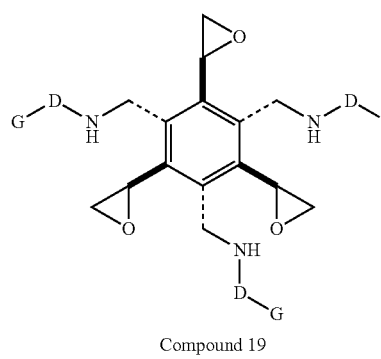

Compound 19

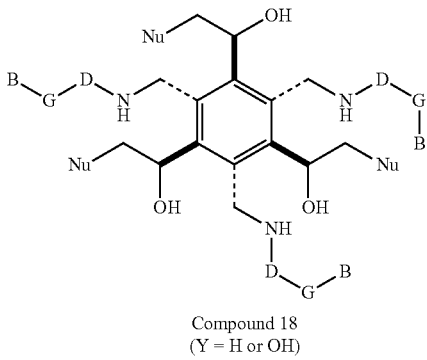

Compound 18
(Y = H or OH)

As shown in Scheme 6, the benzylic amines in Compound 9 may be reacted with an entity D-G, wherein D comprises a grouping of atoms reactive with the benzylic amine and G comprises a grouping of atoms that is reactive with surface B, to form Compound 17. Compound 17, in turn, may then be reacted with surface B to form Compound 18, in which the hexasubstituted benzene is covalently bonded to the surface. Compound 18 may be formed alternately by reacting a surface pre-functionalized with entity D-G, such that entity D reacts with the benzylic amine to promote covalent bonding of the hexasubstituted benzene to the surface. Entity G may already be incorporated within surface B, such that no separate synthetic step is necessary. Although Scheme 6 has shown a single nucleophile affecting epoxide ring opening, it is to be appreciated that a first nucleophile $Nu^1$ may open a first epoxide ring, a second nucleophile $Nu^2$ may open a second epoxide ring, and a third nucleophile $Nu^3$ may open a third epoxide ring, wherein at least one of $Nu^1$, $Nu^2$ and $Nu^3$ is different.

As an illustrative example, the grouping of atoms D in entity D-G may comprise an electrophile that is reactive with the benzylic amine. Suitable electrophiles that may react with the benzylic amine include, but are not limited to, leaving groups such as halides or sulfonates, acyl halides, Michael acceptors, epoxides, or the like. The electrophile may or may not remain intact within linking group L after reacting with the benzylic amine. Particularly suitable examples of linking group L may comprise secondary or tertiary benzylic amines or secondary or tertiary amides. The grouping of atoms G in entity D-G may be selected to react with one or more functional groups located upon surface B. For example, in the case of a polymer surface, the grouping of atoms G may comprise a functional group that is reactive with a polymer side chain or is itself polymerizable when combined with other monomers under suitable conditions. In the case of a glass surface, grouping of atoms G may comprise a silane to form Si—O bonds with surface hydroxyl groups upon the glass surface.

As shown in Scheme 7, benzylic amines may also undergo single- or multi-step functionalization to promote surface attachment without disturbing the epoxides until a desired time. In particular, the benzylic amines in Compound 11 may be directly reacted with a suitably functionalized surface to form Compound 20, in which entities D and G link surface B to the benzylic carbon. Alternately, the benzylic amines may be functionalized with entity D-G to introduce functionality that is reactive with the surface (Compound 19), before forming Compound 20 in a subsequent synthetic step, wherein entity D-G is defined similarly to the corresponding entity D-G for Scheme 6. After covalently attaching the hexasubstituted benzene to the surface, the surface-bound epoxides may then undergo opening with a suitable nucleophile to form Compound 18 to introduce a sensing functionality or other desired modification to the surface, as discussed in further detail above. After opening of the epoxides with a suitable nucleophile, the resulting benzylic alcohols may either remain in the surface-bound reaction product (Y=OH) or undergo further reduction to affect their removal (R=H). Suitable techniques for removal of the benzylic alcohols are addressed in more detail above. Although Scheme 7 has shown a single nucleophile affecting epoxide ring opening, it is again to be appreciated that a first nucleophile Nu' may open a first epoxide ring, a second nucleophile Nu' may open a second epoxide ring, and a third nucleophile $Nu^3$ may open a third epoxide ring.

In a particular example, surface attachment may be realized by attachment of acrylic acid or a derivative thereof (e.g., acrylic acid, methacrylic acid, acrylamide, methacrylamide, and the like) to a hexasubstituted benzene following epoxide ring opening. In other particular instances, surface attachment may be realized by attachment of acrylic acid or a derivative thereof to the benzylic amines. In both instances, the vinyl group of the acrylic acid or acrylic acid derivative may be reacted thermally or optically through a free radical mechanism with a corresponding vinyl group on the surface, particularly a polymer surface bearing a free vinyl group or a vinyl-functionalized metal, glass, or ceramic surface. Scheme 8 below shows an illustrative process whereby an acrylate-functionalized hexasubstituted benzene may undergo attachment to a vinyl-functionalized surface.

Scheme 8

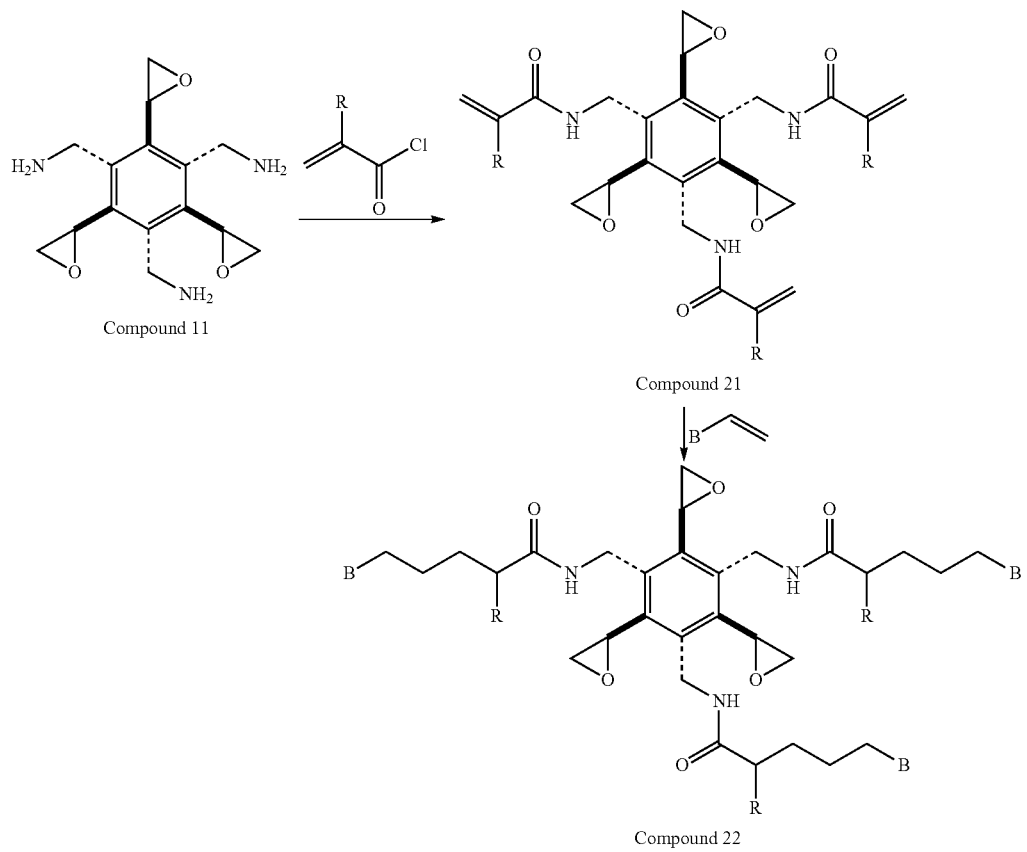

In Scheme 8, B represents a polymer surface or similar type of surface and R represents a hydrocarbyl group, particularly a methyl group. Once surface deposition and covalent bonding have taken place (Compound 22), the epoxide groups may be reacted to introduce sensing functionalities suitable to promote sensing of a desired analyte.

In another synthetic alternative, a carboxylate form of acrylic or methacrylic acid may open the epoxides in Compound 11, and the amines may then undergo a reaction to introduce a functionality capable of binding or sensing an analyte of interest, as shown more generically in Scheme 9 below. Alternately, epoxide opening may take place at the azide stage prior to conversion of the azides into amines. The bound acrylic or methacrylic acid may then undergo polymerization with a reactive vinyl group to append the hexasubstituted benzene to a surface.

Another synthetic variant may be obtained by epoxidizing the product mixture in Scheme 1A and then reacting the various epoxides with methacrylic acid or a derivative thereof under basic conditions, such as in the presence of cesium carbonate, to promote nucleophilic epoxide opening. The resulting α-hydroxymethacrylate esters may then be reacted with an olefinic monomer or a surface olefin to promote surface attachment.

In view of the foregoing, particular examples sensor constructs suitable for analyte sensing may comprise a modified surface bearing a hexasubstituted benzene having a structure represented by Compound 14A,

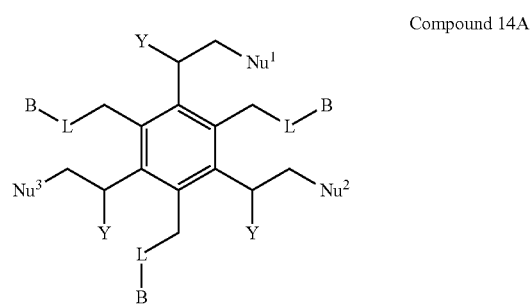

Compound 14A wherein $Nu^1$, $Nu^2$ and $Nu^3$ are each nucleophiles that may be the same or different, each Y is H or OH, and the other variables are defined as specified above.

The manner in which the hexasubstituted benzene becomes deposited upon a surface in the course of becoming covalently bound thereto is not considered to be particularly limited. In some embodiments, the hexasubstituted benzene may be deposited by a technique such as inkjet printing, stencil printing or the like to result in thin-layer surface-bound patterns of the hexasubstituted benzenes having a defined shape. In other embodiments, spray coating or roller coating the hexasubstituted benzenes onto a surface bearing functionality suitable for promoting covalent bonding may be used to provide relatively uniform surface coverage. Other surface deposition techniques may also be suitable for use in the disclosure herein. For example, hexasubstituted benzenes may be manually or robotically pipetted into individual wells of a plate. In still other embodiments, the hexasubstituted benzenes may be combined under bulk reaction conditions with a compound bearing reactive functionality to promote covalent bonding between the two, in which the entire reaction product may define a sensor construct rather than a hexasubstituted benzene bound to a discrete surface.

In the description above, covalent bonding of the hexasubstituted benzenes takes place through the benzylic carbon atoms and introduction of additional functionality takes place through nucleophilic opening of the epoxides. In alternative embodiments of the present disclosure, covalent bonding to a surface may take place through the epoxides, and the benzylic carbon atoms may be employed for introducing further functionality. Such an approach is outlined in more detail in Scheme 9 below.

zylic amines, thereby forming Compound 25. Specifically, as shown in Scheme 9, grouping of atoms E-F may undergo a reaction with the benzylic amines, in which E is an electrophile and F is a functional group bonded to the electrophile. Suitable electrophiles may include, for example, leaving groups, acyl halides, Michael acceptors, epoxides and the like. The electrophile may remain bonded to the benzylic amine after undergoing a reaction therewith, or it may be displaced in the course of forming a linking group between the benzylic amine and functional group F. Functional group F may aid in promoting analysis of an analyte of interest or modifying a surface in a desired manner.

As an alternative to the surface attachment procedure shown in Scheme 9, a benzylic halide such as Compound 5A may undergo surface attachment in a similar manner by reacting the epoxides with a surface nucleophile. Thereafter,

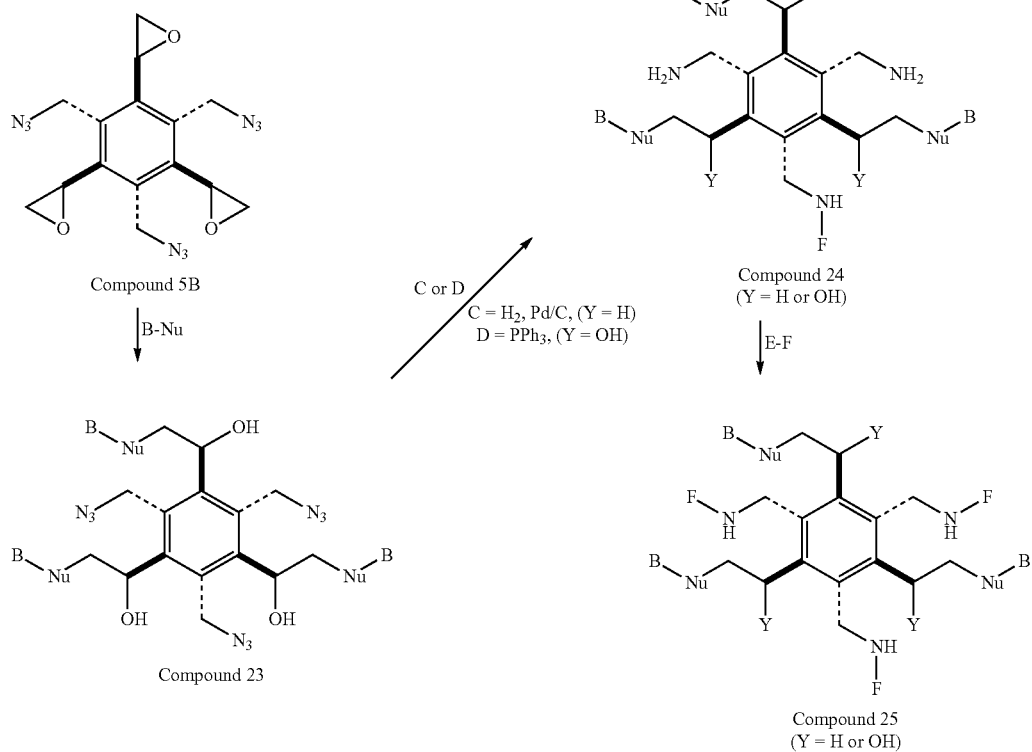

Referring to Scheme 9, the epoxides in Compound 5B may be reacted with a surface nucleophile to promote covalent attachment of the hexasubstituted benzene to a surface, thereby forming Compound 23. Suitable surface nucleophiles may include, for example, primary or secondary amines or similar groups that are reactive with epoxides. Thereafter, the benzylic azides may be reduced, either catalytically with hydrogen and Pd/C or using triphenylphosphine (Staudinger reduction), thereby forming Compound 24. Depending on how the azide reduction is conducted, the benzylic hydroxyl group may either remain intact or undergo removal, as discussed above. After forming the benzylic amines in Compound 24, the benzylic amines may then undergo reaction with a grouping of atoms suitable to introduce additional functionality onto the benthe benzylic halides may be displaced with sodium azide, with the resulting benzylic azides being further functionalized in a manner similar to that discussed above in reference to Scheme 9.

As still another alternative to the surface attachment procedure shown in Scheme 9, the epoxides in Compound 5B may be nucleophilically opened with a reactive group, such as the carboxylate of acrylic or methacrylic acid. The azides may then be reduced to amines and undergo subsequent functionalization, as shown in Schemes 10 and 11 below. The bound acrylic or methacrylic acid may then undergo a reaction with a reactive alkene group to promote surface attachment. Compounds 25A and 25B show structures that may be capable of binding iron and lithium, respectively.

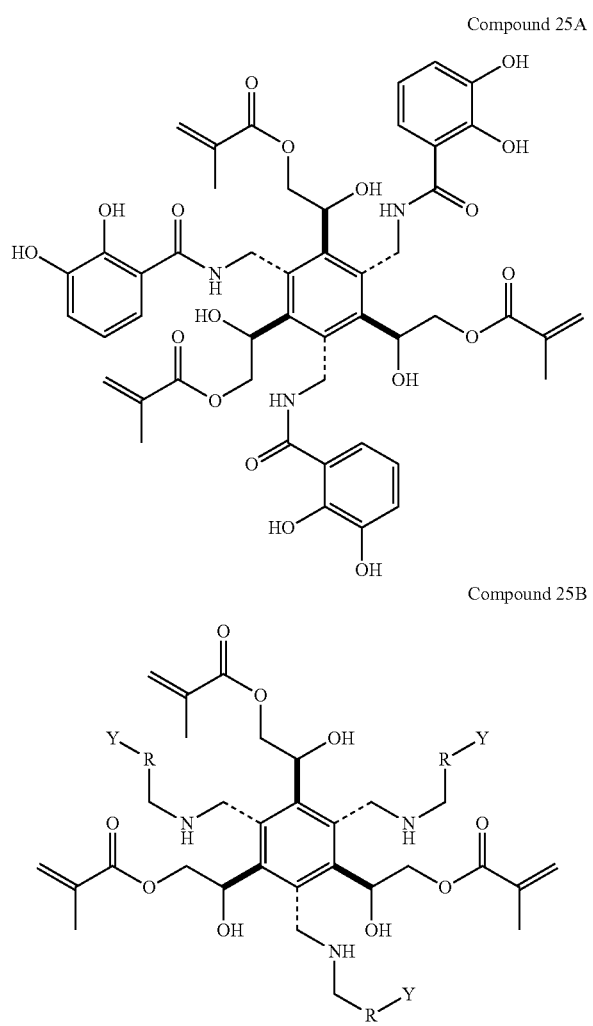

Compound 25A

Compound 25B

In Compound 25B, R is an alkyl, aryl or polyether, and Y is $CO_2H$, $P(=O)OH_2$, $SO_3H$, or $NHSO_2Z$, wherein Z is $CH_3$, $CF_3$, $C_6H_5$ or $C_6H_4NO_2$. In a particular example, R is $(CH_2)_n$ and Y is $CO_2H$, wherein n is an integer ranging from 2 to 4.

As illustrated above, the hexasubstituted benzenes disclosed herein are designed such that they may be reacted with one or more nucleophiles or other reactive compounds to introduce a range of further functionality directed toward a particular face of the hexasubstituted benzenes. In particular embodiments, the hexasubstituted benzenes may be reacted with a first nucleophile, a second nucleophile, and a third nucleophile that differ from one another to introduce three different sensing functionalities onto the hexasubstituted benzene. In other embodiments, the hexasubstituted benzenes may be reacted with a first nucleophile and a second nucleophile that differ from one another, such that the hexasubstituted benzenes incorporate two of one of the nucleophiles and one of the other nucleophile. The nucleophiles may all be the same in still other embodiments. Particularly suitable nucleophiles for use in the disclosure herein are nitrogen nucleophiles, wherein the nitrogen nucleophiles bear further functionality of interest for incorporation upon the hexasubstituted benzenes. In particular embodiments, one or more of the nucleophiles may bear functionality that undergoes a molecular association with an analyte of interest or modifies a surface in a desired manner.

The nucleophiles may bear hydrocarbyl groups of sufficient lengths to hydrophobically modify a surface and/or incorporate one or more heteroatom groups to hydrophilically modify the surface. In non-limiting examples, an amine-containing polyether may be reacted with the hexasubstituted benzenes in order to hydrophilically modify the surface. Other suitable groups that may be incorporated within the nucleophiles that react with the hexasubstituted benzenes may be envisioned by one having ordinary skill in the art and having the benefit of the disclosure herein. Other of the nucleophiles may be spectroscopically active to promote detection of molecular association with a binding group, and optionally one of the nucleophiles may comprise a buffering functionality to promote a desired pH range at which the molecular association of interest occurs.

The hexasubstituted benzenes of the present disclosure may be utilized in various sensing applications when functionalized with sensing functionalities capable of undergoing a molecular association with a particular analyte of interest. Surface-bound hexasubstituted benzenes capable of undergoing a molecular association with an analyte of interest may comprise at least a portion of a sensor construct. Additional electronics may produce a quantifiable signal in the presence of an analyte of interest, or the hexasubstituted benzenes may be spectroscopically interrogated in the presence of an analyte of interest to afford a response that may be correlated with the amount of analyte present. The moieties capable of undergoing molecular association with an analyte of interest may be introduced to the hexasubstituted benzenes by one or more nucleophiles that react with the epoxides, or if the epoxides are used for promoting surface attachment (Scheme 9), via other reactive functionalities such as electrophiles that are reactive with benzylic amines.

In a specific example, hexasubstituted benzenes of the present disclosure may be covalently bonded to a polymer surface comprising a macroparticulate formed from glycidyl (meth)acrylate or a similar monomer bearing an epoxide side chain, followed by nucleophilic opening thereof. Such macroparticulates and use thereof are described in further detail in International Patent Applications PCT/US2020/041407 and PCT/US2020/041417, each filed on Jul. 9, 2020 and Incorporated herein by reference in its entirety.

Suitable macroparticulates may comprise a reaction product of an epoxide-containing (meth)acrylic polymer or copolymer and a compound bearing a nitrogen nucleophile, which may open at least a portion of the epoxide groups in the polymer and form covalent bonds. The nitrogen nucleophile may be present upon the hexasubstituted benzene, or the hexasubstituted benzene may be introduced after nucleophilic epoxide opening has taken place. In addition, the functionalized (meth)acrylic polymers and copolymers may be further crosslinked to convey additional mechanical stability to the macroparticulates disclosed herein. Crosslinking may take place before or after reaction with the nitrogen nucleophile occurs.

Glycidyl methacrylate and similar monomers bearing a side-chain epoxide group may be polymerized and rendered into a form suitable for undergoing further functionalization. In particular, glycidyl methacrylate and similar monomers may be polymerized to a first polymerization state (e.g., through a living polymerization reaction or a free radical polymerization reaction) comprising a solid polymer product that may be isolated and rendered into a predetermined shape suitable for undergoing further functionalization, such as in the form of a sphere or extrudate. Other polymerization techniques (e.g., free radical polymerization, solution polymerization, suspension polymerization, or emulsion polymerization) may also be suitable to achieve the first polymerization state. The structure obtained after rendering the polymer into a desired shape in the first polymerization state is solid, although some minor voids may be present depending on manufacturing or processing inconsistencies. The density obtained after rendering the polymer into the predetermined shape may represent that of the as-obtained polymer from the polymerization reaction. A profile of the predetermined shape rendered at the pre-functionalization stage may be largely maintained following functionalization, except for undergoing volume expansion and a corresponding decrease in the density. That is, functionalization may promote an increase in size and/or other morphological changes of the pre-functionalization shape to afford the increased size and decreased density, while still maintaining the overall appearance of the predetermined shape following functionalization. An internal cavity may form during functionalization and particularly decrease the density. The internal cavity tends to be spherical or substantially spherical and differs from minor voids present in the pre-functionalization shape.

Suitable living polymerization conditions for (meth) acrylic monomers may include Cu(I) mediation in the presence of a suitable radical initiator, such as AIBN. It is also to be appreciated that suitable Cu(I) active species may be produced in situ by oxidation or reduction of Cu(0) or Cu(II), respectively. If left unquenched, the dangling reactive intermediate may undergo further polymerization when exposed to more olefinic monomer or another entity suitable for reacting with the reactive intermediate. In living-polymerized poly(glycidyl methacrylate) and similar (meth)acrylic polymers or copolymers, the dangling reactive intermediate may undergo further polymerization when functionalizing the polymer initially obtained in a first polymerization state (pre-functionalization), thereby affording a second polymerization state after functionalization with a nitrogen nucleophile has taken place. In the first polymerization state, the polymer may still be easily manipulated into a desired, predetermined shape, and then undergo further curing in conjunction with functionalization with a nitrogen nucleophile according to the disclosure herein. The second polymerization state may represent a higher molecular weight than does that of the first polymerization state.

When poly(glycidyl methacrylate) or a similar polymer is reacted with a nitrogen nucleophile in the presence of a suitable base, the polymer and its rendered shape may undergo a morphological change during functionalization. In particular, the shape rendered to the polymer or copolymer in the first polymerization state may undergo expansion, such that the shape is less dense and has a larger volume following functionalization with the nitrogen nucleophile. Spherical pre-functionalization shapes, for example, may form a hollow sphere upon functionalization with a nitrogen nucleophile. Other pre-functionalization shapes may similarly form an internal cavity upon functionalization, albeit with a more randomized exterior shape. Functionalization may occur (via epoxide opening with the nitrogen nucleophile) without the base being present, but volume expansion and internal cavity formation may not occur. Suitable bases for forming expanded macroparticulates may include a tertiary amine base, such as trimethylamine, triethylamine, N,N-diisopropylethylamine (Hunig's base), 2,2,6,6-tetramethylpiperidine, 1,8-diazabicyclo[5.4.0]undec-7-ene (DBU), 1,5-diazabicyclo[4.3.0]non-5-ene (DBN), 4-dimethylaminopyridine (DMAP) and the like. Other mild Lewis bases may also be suitable.

A suitably substituted hexasubstituted benzene may promote epoxide opening in accordance with the disclosure above. Alternately, a different nitrogen nucleophile may promote epoxide opening, and the hexasubstituted benzene may thereafter react with a reaction product formed during epoxide ring opening. Examples of nucleophiles that may be utilized in this manner include, for instance, ethylenediamine and iminodiacetic acid. Other aminopolycarboxylic acids, such as glutamic acid diacetic acid, methylglycine diacetic acid, or the like may also be suitable ligands for use in functionalizing the macroparticulates according to the disclosure herein. Similarly, other $C_2$-$C_8$ alkylenediamines, such as 1,3-propanediamine, 1,4-butanediamine, 1,5-pentanediamine, and 1,6-hexanediamine, may also be suitable for functionalizing the (meth)acrylic polymers and copolymers according to the disclosure herein, wherein further functionalization of the alkylenediamine may take place after the reaction with the macroparticulates takes place. Polyamines, including branched polyamines, may also be reacted with the macroparticulates and then further functionalized after a reaction with the macroparticulates takes place.

Macroparticulates produced according to the disclosure herein may be formed from a pre-functionalization, extruded shape having a diameter of about 1.5 mm to about 2.5 mm, typically about 2.25 mm. Spherical post-functionalization shapes formed from such extrudates (after rolling in a pre-functionalization spherical shape) may have an effective diameter ranging from about 5.5 mm to about 11 mm, or about 6.2 mm to about 8.6 mm, or about 6.2 mm to about 10.5 mm, or about 6 mm to about 6.5 mm, or about 6.5 mm to about 7.0 mm, or about 7.0 mm to about 7.5 mm, or about 7.5 mm to about 8.0 mm, or about 8.0 mm to about 8.5 mm, or about 8.5 mm to about 9.0 mm, or about 9.0 mm to about 9.5 mm, or about 9.5 mm to about 10.0 mm, or about 10.0 mm to about 10.5 mm, or about 10.5 mm to about 11.0 mm. Depending on shape, non-spherical shapes may have effective diameters (cross-sectional dimensions) ranging from about 5.0 mm to about 11.5 mm, or about 5.0 mm to about 6.0 mm, or about 6.0 mm to about 7.0 mm, or about 7.0 mm to about 8.0 mm, or about 8.0 mm to about 9.0 mm, or about 9.0 mm to about 10.0 mm, or about 10.0 mm to about 11.0 mm.

When used in sensing applications, the surface-bound hexasubstituted benzenes may be present in any suitable location for interacting with an analyte of interest. Illustrative locations may include, for example, an electrode, test strip, a lateral flow test strip, a flow cell (flow sensor), a static cell, or single-well surface configured to interact with a fluid containing an analyte of interest. Lateral flow test strips featuring the hexasubstituted benzenes disclosed herein may offer a simpler sensing architecture than when enzymes and antibodies are used as in conventional lateral flow test strips. In other instances, the surface-bound hexasubstituted benzenes may be incorporated upon a surface in individual wells of a multi-well plate, thereby facilitating parallel, high-throughput analyte analyses. When incorporated in a multi-well plate, each well may incorporate the same surface-bound hexasubstituted benzene (if multiple samples of the same analyte are to be analyzed in each well) or different surface-bound hexasubstituted benzenes in at least some of the wells (if different analytes are to be analyzed in certain well). Multi-well plates lacking sensing functionalities may also be stockpiled and subsequently modified in situ with one or more nucleophiles to introduce sensing functionalities thereto.

Accordingly, sensor constructs of the present disclosure may comprise a modified surface comprising a surface-bound hexasubstituted benzene, such as the hexasubstituted benzene defined by Compound 18. In particular embodiments, more than one type of nucleophile may be incorporated in the hexasubstituted benzenes, such that at least one of the nucleophiles includes functionality that may associate with an analyte of interest, and an extent of the association between the analyte of interest and the surface-bound hexasubstituted benzene is analytically detectable (e.g., spectroscopically or electrochemically) and correlatable to an amount of the analyte of interest that is present. More specifically, the hexasubstituted benzene may be reacted with $Nu^1$, $Nu^2$ and $Nu^3$, wherein at least one of $Nu^1$, $Nu^2$ and $Nu^3$ includes functionality that associates with an analyte of interest, the association is analytically detectable, and an extent of the association is correlatable to an amount of the analyte of interest that is present in a sample. For example, the spectroscopic or analytical response may be referenced against a calibration curve or lookup table associated with the analyte being assayed with a particular hexasubstituted benzene. Multiple sensors may be employed having such characteristics may be used to assay a plurality of analytes in a complex fluid.

Functionalities capable of undergoing a molecular association with a particular analyte of interest are not considered to be especially limited. Suitable functionalities may include entities such as, for example, chelating ligands, crown ethers, cryptands, porphyrins, calixarenes, analyte-sensitive dyes, pH sensitive compounds, antibodies, enzymes, proteins, biological receptors, or similar entities capable of undergoing a specific molecular interaction with an analyte of interest or a class of related analytes. Choice of a specific entity may be based upon the analyte of interest to be detected and the type of fluid undergoing analysis. Coordinative association of an analyte with a ligand may be desirable in some instances and facilitated by at least one of $Nu^1$, $Nu^2$ and $Nu^3$.

Analysis of the molecular association between the analyte of interest and the hexasubstituted benzene may be determined by any suitable analytical technique. In illustrative embodiments, suitable analytical techniques may include spectrophotometry or electrochemical detection techniques, as well as any combination thereof. The magnitude of the analytical response (e.g., signal intensity) or a change thereof may be correlated to a known amount of analyte using a lookup table, calibration curve or function, or the like.

In addition to a functionality capable of undergoing a specific molecular association with an analyte of interest (binder group), the surface-bound hexasubstituted benzenes may further include a functionality that allows the molecular interaction to be detected more readily. Specifically, a second nucleophile may introduce a functionality configured to promote spectroscopic or electrochemical detection of the hexasubstituted benzene (reporter group). The spectroscopic or electrochemical signature of such a functionality may change when an analyte of interest is associated with the hexasubstituted benzene compared to when the analyte is not associated.

The surface-bound hexasubstituted benzenes may also include an additional functionality that may increase or decrease the strength of the molecular association with the analyte of interest. For example, such functionalities may carry a pH buffer that may increase or decrease the strength of molecular association of pH-sensitive analytes. In other embodiments, such functionalities may carry moieties that may scavenge reactive species that may otherwise preclude formation of a molecular association with an analyte of interest. Other choices for the additional functionality may increase or decrease the electron density upon the phenyl ring to increase or decrease the strength of the molecular association with an analyte of interest as needed.

Accordingly, in some embodiments, the hexasubstituted benzenes may comprise three different functionalities introduced by nucleophiles to promote sensing of one or more analytes under appropriate conditions. In particular embodiments, at least one of the first nucleophile, the second nucleophile and the third nucleophile may carry functionality that is capable of associating with an analyte of interest in order to promote sensing thereof. In some or other embodiments, at least one of the first nucleophile, the second nucleophile and the third nucleophile may carry functionality that aids in promoting detection of the analyte of interest, specifically molecular association of the analyte of interest with the hexasubstituted benzene. In still additional embodiments, at least one of the first nucleophile, the second nucleophile, and the third nucleophile may carry functionality that changes the strength of the molecular association of the analyte of interest with the hexasubstituted benzene. In more specific embodiments, at least one of the first nucleophile, the second nucleophile, and the third nucleophile may serve as a buffer to prevent sensing from being triggered by an environmental change in pH or a similar event. Alternately, a buffer may facilitate a desired molecular association with an analyte of interest within a specific pH range.

Thus, in some embodiments, sensor constructs of the present disclosure may comprise a surface-bound hexasubstituted benzene having three different functionalities introduced by nucleophiles to aid in promoting detection of an analyte of interest. A first functionality may undergo molecular association with the analyte of interest, a second functionality may promote detection of the molecular association, and a third functionality may include a one or more moieties that alter the strength of the molecular association. Alternative hexasubstituted benzene configurations include those in which: 1) the first functionality is present in combination with two third functionalities or two first functionalities are present in combination with a third functionality, 2) the first functionality is present in combination with two second functionalities or two first functionalities are present in combination with a second functionality, or 3) three occurrences of the first functionality are present upon the hexasubstituted benzene. The alternative hexasubstituted benzene configurations may be used if the molecular association of the analyte of interest may be satisfactorily detected without introducing further functionality to the hexasubstituted benzenes.

For example, in particular embodiments of the present disclosure, the hexasubstituted benzenes may feature a first nucleophile carrying functionality capable of undergoing molecular association with an analyte of interest, and a second nucleophile carrying functionality that demonstrates a different spectroscopic, electrochemical, or electromechanical response when an analyte is bonded to or associated with the functionality carried by the first nucleophile. Moreover, the hexasubstituted benzenes may feature a third nucleophile carrying functionality that may further tailor the bonding or association of the analyte with the first nucleophile or alter the detection signature provided by the second nucleophile.

Illustrative analytes or classes of analytes that may undergo detection and analysis according to the disclosure herein are not considered to be particularly limited and include substances such as, for example, trace metals, salts, organics, poisons, biomarkers, metabolites, hormones, cells, toxins, drugs, nerve agents and other chemical warfare agents, explosives, microorganisms (including bacteria, viruses, protozoa, fungi, and the like), and the like. These and similar analytes may be analyzed in a diverse range of fields including, for example, process and system monitoring, water and other environmental analyses, health and safety, medical and diagnostic testing, oilfield testing and servicing, agricultural testing, industrial testing, and the like. Fluids that may be analyzed using the hexasubstituted benzenes disclosed herein include, for example, industrial waste water, process water, ground water, produced or flowback water from a wellbore, etching or digestion water from electronics processing, waste water streams, water from precious metal refining, water from catalyst waste refining, mining runoff water, geothermal brines, organic liquids, oil, blood, urine, other bodily fluids, and similar complex fluids. The fluids may be simple or complex fluids, including either single-phase or multi-phase complex fluids. Other suitable analytes and fluids containing the analytes may be envisioned by one having ordinary skill in the art.

Multi-phase complex fluids that may undergo analysis according to the disclosure herein include liquid-liquid, solid-liquid, gas-liquid, solid-gas or gas-liquid-solid complex fluids. The designation of a fluid as being "complex" refers to an analyte of interest being present in a specific phase, wherein the phase containing the analyte of interest is in contact with another phase which may or may not contain the analyte. As such, in addition to bulk fluids, analytes also may be detected upon a surface according to the disclosure herein, wherein the analyte upon the surface may be present as a solid or in a liquid phase (e.g., aerosol, droplet or the like) and the other component of the multi-phase complex fluid is the atmosphere (gas or gas-liquid phase). Submerged surfaces may also have a complex fluid at the interface thereof with a bulk liquid, wherein liquid in close proximity to the surface and liquid remote from the surface may afford a liquid-liquid complex fluid.

In a specific example of a surface-based complex fluid analysis, a surface may contain an analyte resting upon the surface in the form of an aerosol, droplet, or like structure and exposed to the atmosphere. In this case, the multi-phase complex fluid may be considered to be liquid-gas in nature (i.e., a surface liquid and atmospheric gas). Microbes, DNA, RNA and like molecules disposed upon a surface are particular examples of analytes that may be suitable for testing in such complex fluid analyses. Foodstuffs, medical equipment, and the like are among the surfaces that may be analyzed.

Solid-gas complex fluids may undergo analysis according to the disclosure herein by contacting a particulate-containing gas with a sensor construct of the present disclosure, wherein the analyte of interest is present upon the particulates or constitutes the particulates themselves. Examples of complex fluids that may be analyzed in this manner include, for example, engine exhaust gas, power plant exhaust gas, flue gas, coking gas, smelting gas, incinerator gas, vent hood outflow gas, and the like. Particular analytes of interest that may be present as solid particulates and undergo analysis according to the disclosure herein include, for example, carbon or carbon oxides, nitrogen compounds, sulfur compounds, metals, toxins, chemical agents, and the like.

As such, sensing methods of the present disclosure may comprise exposing a fluid containing at least one analyte to a sensor construct comprising a hexasubstituted benzene having at least one functionality capable of undergoing molecular association with the at least one analyte, determining an analytical response of the hexasubstituted benzene in the presence of the at least one analyte, and correlating the analytical response or a change thereof to an amount of the at least one analyte present in the fluid. The analytical response or the change thereof may be correlated to the amount of the at least one analyte present using a lookup table, a calibration curve or function, or any combination thereof.

The fluid undergoing analysis may be a simple fluid or a complex fluid, including both single-phase and multi-phase complex fluids. Particularly suitable fluids that may undergo analysis in accordance with the disclosure herein include, for example, biological fluids, oilfield fluids, and complex fluids encountered in other industries, examples of which are provided in further detail below. The amount of analyte present in such fluids may be utilized to determine a further course of action for processes of various types, as discussed hereinafter.

Sensor constructs capable of analyzing fluids, especially complex fluids, may include hexasubstituted benzenes having one or more sensing functionalities capable of providing an analytical response in the presence of an analyte of interest. Suitable sensor constructs are described in greater detail above and may include hexasubstituted benzenes bound to a surface. Multiple hexasubstituted benzenes each functionalized to undergo molecular association with a particular analyte of interest may be used when analyzing multiple analytes. The multiple functionalities upon a given hexasubstituted benzene may include those configured for binding an analyte of interest (binder group) and producing a detectable output, such as spectroscopically, when an analyte of interest is bound to or associated with the hexasubstituted benzene (reporter group). An optional buffering functionality may be present in some cases as well. In some instances, the combination of a binder group may be sufficient to promote detection of an analyte of interest. In other instances, both a binder group and a reporter group may be present. In still other instances, the combination of a binder group, a reporter group, and a buffer group may be present to promote detection of an analyte of interest.

Functionalities capable of undergoing molecular association with a specific analyte of interest in a fluid are not considered to be particularly limited. Suitable functionalities may include entities such as chelating ligands, crown ethers, analyte-sensitive dyes, pH sensitive compounds, antibodies, enzymes, proteins, biological receptors, or similar entities capable of undergoing a specific molecular interaction with an analyte of interest or a class of related analytes. Choice of a specific entity may be based upon the analyte of interest to be detected. The specific entity chosen may be appended to a suitable nucleophile or other reactive moiety to promote functionalization of a hexasubstituted benzene in the manner described hereinabove.

Analysis of the molecular association between the analyte of interest and the sensing functionality upon the hexasubstituted benzene may be determined by any suitable analytical technique. In illustrative embodiments, suitable analytical techniques may include spectrophotometry or electrochemical detection techniques. The magnitude of the analytical response (e.g., signal intensity or change thereof) may be correlated to a known amount of analyte using a lookup table, calibration curve, or the like.

In addition to a functionality capable of undergoing a specific molecular association with an analyte of interest, the surface-bound hexasubstituted benzenes may further include a functionality that allows the molecular interaction to be detected more readily. Specifically, a second nucleophile or other reactive compound may introduce a functionality configured to promote spectroscopic or electrochemical detection of the hexasubstituted benzene when an analyte is molecularly associated therewith. The spectroscopic or electrochemical signature of such a functionality may change when an analyte of interest is associated with the hexasubstituted benzene compared to when the analyte is not associated.

The surface-bound hexasubstituted benzenes may also include an additional functionality that may increase or decrease the strength of the molecular association with the analyte of interest. For example, such functionalities may carry a pH buffer that may increase or decrease the strength of molecular association of pH-sensitive analytes. In other embodiments, such functionalities may carry a moiety that may scavenge reactive species that may otherwise preclude formation of a molecular association with an analyte of interest. Other choices for the additional functionality may increase or decrease the electron density upon the phenyl ring to increase or decrease the strength of the molecular association with an analyte of interest as needed.

Accordingly, in some embodiments, the hexasubstituted benzenes may comprise three different functionalities introduced by nucleophiles to promote sensing of one or more analytes under appropriate conditions. In particular embodiments, at least one of the first nucleophile, the second nucleophile and the third nucleophile may carry functionality that is capable of associating with an analyte of interest in order to promote sensing thereof. In some or other embodiments, at least one of the first nucleophile, the second nucleophile and the third nucleophile may carry functionality that aids in promoting detection of the analyte of interest, specifically molecular association of the analyte of interest with the hexasubstituted benzene. In still additional embodiments, at least one of the first nucleophile, the second nucleophile, and the third nucleophile may carry functionality that changes the strength of the molecular association of the analyte of interest with the hexasubstituted benzene. In more specific embodiments, at least one of the first nucleophile, the second nucleophile, and the third nucleophile may serve as a buffer to prevent sensing from being triggered by an environmental change in pH or a similar event. Alternately, a buffer may facilitate a desired molecular association with an analyte of interest within a specific pH range. In addition, pH buffering or scavenging may sequester or inactivate interfering analytes or substances that may otherwise preclude successful analysis of an analyte of interest.

In particular embodiments of the present disclosure, the hexasubstituted benzenes may feature a first nucleophile carrying functionality capable of undergoing molecular association with an analyte of interest, and a second nucleophile carrying functionality that demonstrates a different spectroscopic, electrochemical, or electromechanical response when an analyte is bonded to or associated with the functionality carried by the first nucleophile. Moreover, the hexasubstituted benzenes may feature a third nucleophile carrying functionality that may further tailor the bonding or association of the analyte with the first nucleophile or alter the detection signature provided by the second nucleophile.

Hexasubstituted benzenes used in analyzing fluids according to the disclosure herein may be configured in any arrangement. When utilizing multiple hexasubstituted benzenes for assaying multiple analytes, the multiple hexasubstituted benzenes may be arranged in a manner suitable for receiving a signal separately from each hexasubstituted benzene, wherein the intensity of the signal received is indicative of the amount of analyte present and a response or response change (based on signal intensity) may be indicative of the amount of analyte present. In non-limiting examples, multiple hexasubstituted benzenes may be arranged in a row-and-column plate arrangement or a similar gridded array, such that each hexasubstituted benzene may be interrogated separately (e.g., spectroscopically) in the presence of a fluid containing one or more analytes. Each hexasubstituted benzene may be spectroscopically interrogated separately over a period of time (e.g., in a time-multiplexed fashion), or the signals may be received simultaneously using an array detector in a non-limiting example, after the hexasubstituted benzene has been contacted with the fluid. One or more analytes may be analyzed according to the disclosure herein. The manner in which the hexasubstituted benzenes are contacted with the fluid (e.g., a complex fluid or a simple fluid) is not considered to be particularly limited. Contact between the hexasubstituted benzenes and the fluid may be static (stationary) or dynamic (flowing).

In non-limiting examples, each hexasubstituted benzene may be capable of producing a signal that is unique for each analyte of interest within a fluid. Should a particular hexasubstituted benzene provide a signal containing a contribution from two or more analytes (e.g., as a result of chemical or spectroscopic interference) from the fluid, the signal contribution from each analyte may be resolved/deconvoluted if another hexasubstituted benzene is capable of detecting one of the analytes specifically. For example, if a first hexasubstituted benzene provides a specific output proportional to the amount of a first analyte present and a second hexasubstituted benzene produces an output proportional to the combined amount of the first analyte and a second analyte, the amount of the second analyte may be determined by subtracting the output obtained from the first hexasubstituted benzene from that obtained from the second hexasubstituted benzene.

Illustrative analytes or classes of analytes that may undergo detection and measurement according to the disclosure herein are not considered to be particularly limited and include substances such as, for example, trace metals, salts, organics, poisons, biomarkers, metabolites, hormones, cells, toxins, drugs, nerve agents and other chemical warfare agents, explosives, microorganisms (including bacteria, viruses, protozoa, fungi, and the like), and the like. These and similar analytes may be analyzed in a diverse range of fields including, for example, process and system monitoring, water and other environmental analyses, health and safety, medical and diagnostic testing, oilfield testing, agricultural testing, industrial testing, food products and the like. Complex fluids containing these analytes may be commonly encountered, any of which may be satisfactorily analyzed by applying the principles of the disclosure herein. Simple fluids containing these and other analytes may also be assayed through use of the disclosure herein.

Particular examples of analytes that may undergo analysis according to the disclosure herein include various metal salts. Suitable metal salts may include ionic forms such as, for example, an alkali metal ion, an alkaline earth metal ion, a halide ion, a phosphate, a nitrate, a borate, an arsenate, a silicate, a selenite, a titanium ion, a chromium ion, a manganese ion, an iron ion, a ruthenium ion, an osmium ion, a cobalt ion, a rhodium ion, an iridium ion, a nickel ion, a palladium ion, a platinum ion, a copper ion, a silver ion, a gold ion, a zinc ion, a cadmium ion, a mercury ion, an aluminum ion, a boron ion, and any combination thereof. More particular examples may include, for instance, divalent metal cation, a barium cation, an iron (II) cation, an iron (III) cation, a sulfate anion, and any combination thereof.

More specific examples of fluids that may be analyzed using the disclosure herein include, for example, biological fluids (e.g., blood, saliva, urine, and the like), food products (e.g., milk, salad dressing, juices and the like), drinking water, surface water (e.g., streams, ponds, reservoirs, agricultural runoff, and the like), industrial water (e.g., water purification facilities, mining wastewater, chemical process water, and the like), oilfield fluids (e.g., drilling fluids, stimulation fluids, fracturing fluids, and the like), oilfield-produced water (e.g., formation water, ground water, frac water, slickwater, and the like), industrial product mixtures, bacterial fermentation broths, and the like. Identification and quantification of multiple analytes within these and similar complex fluids may be accomplished using the disclosure herein. Suitable analytes that may be present in these and other fluids are wide-ranging in scope, and one having ordinary skill in the art will recognize various types of analytes that may be present in a given sample. Salts, organics, biological molecules, polymers, and the like may be present in a given complex fluid and may satisfactorily be analyzed by applying the disclosure herein. Complex fluids having multiple phases may be particularly complicated to analyze using conventional sensor and laboratory analysis techniques. These issues may be resolved through direct contact of the complex fluid with the hexasubstituted benzenes disclosed herein.

Oilfield fluids and analytes therein that may be monitored using the hexasubstituted benzenes of the present disclosure are not considered to be particularly limited. In non-limiting embodiments, oilfield fluids that may be monitored according to the disclosure herein include treatment fluids, produced fluids (e.g., oil or produced hydrocarbon resources, produced water, spent or partially spent treatment fluids, and the like), treatment fluids formulated with produced water, chemicals being used to form treatment fluids, and the like. Treatment fluids that may be analyzed according to the disclosure herein include, but are not limited to, drilling fluids, fracturing fluids, acidizing fluids, conformance fluids, diverting fluids, damage control fluids, remediation fluids, scale removal and inhibition fluids, chemical floods, sand control fluids, and the like. Other treatment fluids suitable for use in oilfield applications may be envisioned by one having ordinary skill in the art. Treatment fluids analyzed according to the disclosure herein may be aqueous or non-aqueous, emulsified or non-emulsified, or any combination thereof. As such, suitable treatment fluids for analysis may be single- or multi-phase complex fluids. Depending on particular application needs, a single analyte within such oilfield fluids may be monitored by applying the disclosure herein, or multiple analytes may be monitored simultaneously or in sequence with one another.

Analytes that may be present in the oilfield fluids suitable for analyses as specified herein include, for example, oil and oil components, salts, polymers, metal cations, asphaltenes, tar, acids, bases, scale control agents, viscosifying agents, chelating agents, and the like. These and other analytes may be analyzed in an oilfield fluid before introduction to a wellbore, after production from a wellbore, or within the wellbore itself (i.e., while the analyte and the oilfield fluid is still downhole). As discussed above, once suitably functionalized hexasubstituted benzenes have been identified to analyze specifically for a particular analyte or class of analyte, high-throughput analyses may be conducted using the identified sensing chemistry.

As a non-limiting example, functionality specific for analyzing a metal or ion of interest (e.g., a crown ether or ligand) may be appended to the hexasubstituted benzenes to allow specific analyses to be made. Non-limiting examples of metals or ions of interest that may be present in treatment fluids or desirable to exclude from treatment fluids due to deleterious effects therein (e.g., inhibited crosslinking, scaling or the like) include, for example, iron ($Fe^{2+}$ and particularly $Fe^{3+}$), lithium, cesium, strontium, calcium, potassium, sodium, sulfate, borate, and chloride. Suitably functionalized hexasubstituted benzenes of the present disclosure may facilitate detection of these metals or ions to determine if a treatment operation may be satisfactorily conducted. In the case of produced water, for example, analysis of these metals or ions may aid in determining whether a treatment fluid may be satisfactorily formulated from the produced water to afford decreased treatment fluid formulation costs.

Illustrative substances that can be present in any of the treatment fluids or other wellbore fluids for analysis according to the disclosure herein include, for example, acids, acid-generating compounds, bases, base-generating compounds, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be present as well and analyzed according to the disclosure herein.

In a particular example, a fracturing fluid may be analyzed using the hexasubstituted benzenes disclosed herein. A fracturing fluid may comprise any number of fracturing fluid components, particularly at least a carrier fluid and proppant particulates. Other fracturing fluid components that may be present include, for example, a surfactant, a gelling agent, a crosslinking agent, a crosslinked gelling agent, a diverting agent, a salt, a scale inhibitor, a corrosion inhibitor, a chelating agent, a polymer, an anti-sludging agent, a foaming agent, a buffer, a clay control agent, a consolidating agent, a breaker, a fluid loss control additive, a relative permeability modifier, a tracer, a probe, nanoparticles, a weighting agent, a rheology control agent, a viscosity modifier (e.g., fibers and the like), and any combination thereof. Any of these fracturing fluid components can be assayed according to the disclosure herein in order to determine suitability for conducting a fracturing operation or determining how a fracturing operation is progressing.

In another particular example, acidizing fluids and the performance of acidizing operations may be monitored according to the disclosure herein. Acidizing fluids may contain a carrier fluid and at least one acid. Most typically, the at least one acid can be selected from hydrochloric acid, hydrofluoric acid, formic acid, acetic acid, glycolic acid, lactic acid, and/or the like. Hydrochloric acid may be used for acidizing limestone and other carbonate-containing subterranean formations. Hydrofluoric acid is typically used for acidizing silicate-containing and other siliceous formations, including sandstone. The choice of an acid blend suitable for a particular subterranean formation will most often be a matter of routine design for one having ordinary skill in the art. In addition, suitable compounds that form acids downhole (i.e., acid precursors) can also be used. For example, esters, orthoesters and degradable polymers such as polylactic acid can be used to generate an acid in a wellbore. Any of these acidizing fluid components can be assayed according to the disclosure herein in order to determine suitability for conducting an acidizing operation or determining how an acidizing operation is progressing. Other acidizing fluid components that may be present and analyzed according to the disclosure herein include, for example, a chelating agent, a corrosion inhibitor, a surfactant, a gelling agent, a salt, a scale inhibitor, a polymer, an anti-sludging agent, a diverting agent, a foaming agent, a buffer, a clay control agent, a consolidating agent, a breaker, a fluid loss control additive, a relative permeability modifier, a tracer, a probe, nanoparticles, a weighting agent, a rheology control agent, a viscosity modifier, and any combination thereof.

Once an analysis has been conducted, a treatment operation or production operation at a job site may be continued as currently being performed, or the treatment or production operation may be stopped or modified depending upon the outcome of the analysis performed using the hexasubstituted benzenes disclosed herein. In particular, a treatment operation may be conducted or modified based upon the analytical response or the change thereof obtained upon interrogation of the hexasubstituted benzene. Modification of a treatment operation or production operation may occur in real-time or near real-time in particular examples of the disclosure herein. Alternately, if a treatment fluid is determined to have an off-specification analyte concentration, a treatment operation may be proactively altered to accommodate the off-specification analyte concentration prior to introduction to the wellbore, or the treatment fluid may be replaced with a different batch that is on-specification. In any event, more effective treatment or production may be realized through application of the disclosure herein. Similarly, if a produced hydrocarbon resource is not on-specification, as determined through use of the disclosure herein, a treatment operation may be conducted in an attempt to remedy this situation.

A single hexasubstituted benzene containing sensing functionality suitable for assaying a single analyte may be used when assaying an oilfield fluid, provided that a sensor output deconvoluted from interfering signals may be obtained. When multiple analytes in an oilfield fluid are to be analyzed, multiple hexasubstituted benzenes containing sensing functionality suitable for each analyte may be used in the disclosure herein. A single hexasubstituted benzene may disposed in a sensor construct, including flow-through sensors, for analyzing an analyte in an oilfield fluid as the oilfield fluid is introduced to a wellbore, or as the oilfield fluid is produced from the wellbore. In addition, the wellbore fluid may be assayed while downhole as well. Multiple hexasubstituted benzenes may similarly be disposed in individual sensors, including flow-through sensors, or in arrays, which may be disposed along a flow path conveying an oilfield fluid to or from the wellbore. Thus, the hexasubstituted benzene(s) used in analyzing oilfield fluids according to the disclosure herein may be configured in any arrangement suitable for receiving a signal separately from each hexasubstituted benzene, wherein the intensity of the signal received is indicative of the amount of each analyte present. In non-limiting examples, the multiple hexasubstituted benzenes may be arranged in a row-and-column plate arrangement or a similar gridded array, such that each hexasubstituted benzene may be interrogated separately (e.g., spectroscopically) in the presence of an analyte of the oilfield fluid. Multiple flow-through sensors, each configured for assaying a different analyte, may be arranged along or within a flow path, or separate fluid streams may be monitored with a flow-through sensor arranged within each flow path. The hexasubstituted benzene(s) may be spectroscopically interrogated separately over a period of time (e.g., in a time-multiplexed fashion), or the signals may be received simultaneously using an array detector in a non-limiting example, while the hexasubstituted benzene is being contacted with the oilfield fluid. The manner in which the hexasubstituted benzenes are contacted with the oilfield fluid is not considered to be particularly limited. Contact between the hexasubstituted benzenes may be static (stationary) or dynamic (flowing). Flow-through sensor configurations may be particularly desired to facilitate continuous production operations.

In non-limiting examples, each hexasubstituted benzene may be capable of producing a signal that is unique for each analyte of interest within an oilfield fluid. Should a particular hexasubstituted benzene provide a signal containing a contribution from two or more analytes or an analyte of interest and a non-analyte substance (e.g., as a result of chemical or spectroscopic interference) from the oilfield fluid, the signal contribution from each analyte of interest may be resolved/deconvoluted if another hexasubstituted benzene is capable of detecting one of the analytes or a similar interfering substance specifically. For example, if a first hexasubstituted benzene provides a specific output proportional to the amount of a first analyte present and a second hexasubstituted benzene produces an output proportional to the combined amount of the first analyte and a second analyte or interfering substance, the amount of the second analyte may be determined by subtracting the output obtained from the first hexasubstituted benzene from that obtained from the second hexasubstituted benzene.

Functionalities capable of undergoing molecular association with a specific analyte of interest in an oilfield fluid are not considered to be particularly limited. Suitable functionalities may include entities such as chelating ligands, crown ethers, analyte-sensitive dyes, pH sensitive compounds, antibodies, enzymes, proteins, biological receptors, or similar entities capable of undergoing a specific molecular interaction with an analyte of interest or a class of related analytes. Choice of a specific entity may be based upon the analyte of interest to be detected. The specific entity chosen may be appended to a suitable nucleophile or other reactive moiety to promote functionalization a hexasubstituted benzene in the manner described hereinabove.

Biological fluids and analytes therein that may be monitored using the hexasubstituted benzenes of the present disclosure are also not considered to be particularly limited. In non-limiting embodiments, biological fluids that may be monitored according to the disclosure herein include blood, plasma, saliva, urine, cerebrospinal fluid, gastric fluid, and the like. Analytes that may be monitored in these biological fluids and others may include, for example, salts, metal ions, microorganisms, viruses, sugars, ketones, drugs, metabolites, proteins, hormones, the like, or any combination thereof. Other analytes of biological interest may be envisioned by one having ordinary skill in the art. Depending on particular application needs, a single analyte within such biological fluids may be monitored by applying the disclosure herein, or multiple analytes may be monitored simultaneously or in sequence with one another.

As a non-limiting example, functionality specific for analyzing a metal or ion of interest (e.g., a crown ether or ligand) may be appended to the hexasubstituted benzenes to allow specific analyses to be made. Non-limiting examples of metals or ions of interest that may be present in biological fluids include, for example, iron (particularly $Fe^{3+}$), calcium, potassium, sodium, sulfate, and chloride. Suitably functionalized hexasubstituted benzenes of the present disclosure may facilitate detection of these metals or ions to determine if any of these analytes are dysregulated and in need of further medical attention. Suitable reporter moieties that may be incorporated within the hexasubstituted benzenes include chromophores that are responsive to the presence of the analyte of interest, such as dyes, and the like.

Physiological conditions such as, but not limited to, diabetes, ketosis, sepsis, and other conditions producing a distinct physiological marker may be evaluated using the hexasubstituted benzenes disclosed herein. External analytes, such as ethanol and pharmaceuticals, may also be assayed through use of the disclosure herein. Once an amount of the at least one analyte in the biological fluid has been determined, methods of the present disclosure may comprise making a diagnosis, determining a course of treatment, the like or any combination thereof based upon the analytical response or the change thereof associated with the hexasubstituted benzene. In some instances, machine learning algorithms may evaluate collected analyte panel data to determine a preferred course of treatment.

Functionalities capable of undergoing a molecular association or bonding interaction with a specific analyte of interest in a biological fluid are not considered to be particularly limited. Suitable functionalities may include entities such as chelating ligands, crown ethers, analyte-sensitive dyes, pH sensitive compounds, antibodies, enzymes, proteins, or similar entities capable of undergoing a specific molecular interaction with an analyte of interest or a class of related analytes. Choice of a specific entity may be based upon the analyte of interest to be detected. The specific entity chosen may be appended to a suitable nucleophile or other reactive moiety or already contain a reactive moiety to promote functionalization of a hexasubstituted benzene in the manner described hereinabove.

Specific biological analytes of interest, such as proteins, sugars, metabolites, microorganisms, and the like may be detected using a specific biological receptor that has been synthetically manipulated to become covalently bonded to the hexasubstituted benzenes. The biological receptors may be obtained from any biological or commercial source and then undergo further reaction in any of the manners disclosed above to promote covalent bonding to the phenyl ring of the hexasubstituted benzene. As a non-limiting example, free amines or carboxylic acid groups in a biological receptor may be used to promote epoxide opening to attach the biological receptor to the hexasubstituted benzene.

In non-limiting examples, multiple hexasubstituted benzenes may be utilized to determine the amount of each analyte of interest within a biological fluid. Should a particular hexasubstituted benzene provide a signal containing a contribution from two or more analytes or an analyte of interest and a non-analyte substance (e.g., as a result of chemical or spectroscopic interference) from the biological fluid, the signal contribution from each analyte of interest may be resolved/deconvoluted if another hexasubstituted benzene is capable of detecting one of the analytes or a similar interfering substance specifically. For example, if a first hexasubstituted benzene provides a specific output proportional to the amount of a first analyte present and a second hexasubstituted benzene produces an output proportional to the combined amount of the first analyte and a second analyte or interfering substance, the amount of the second analyte may be determined by subtracting the output obtained from the first hexasubstituted benzene from that obtained from the second hexasubstituted benzene.

The hexasubstituted benzene compounds disclosed herein may be used to analyze and/or collect an analyte or other substance of interest from a fluid or from a surface, as discussed in more detail above. In alternative examples, the hexasubstituted benzene compounds of the present disclosure, including surface-bound variants thereof, may be preloaded with a substance and then released into a desired location, such as into a process stream. That is, the hexasubstituted benzene compound may function as a vehicle for conveying the substance to a desired location, wherein the substance may be removed by a stronger binding entity or through encountering less favorable binding conditions. The substance carried by the hexasubstituted benzene compound may be employed to treat or convey a change of various types at the location where the substance is released. Successful delivery of the preloaded substance may be verified by a spectroscopic or electrochemical change in the hexasubstituted benzene once the substance has been released therefrom. Accordingly, the present disclosure also provides hexasubstituted benzene compounds with a substance bound thereto, wherein the substance may be released under suitable conditions. Methods for using the hexasubstituted benzene compounds as a delivery vehicle may comprise: providing a hexasubstituted benzene compound with a substance bound thereto, exposing the hexasubstituted benzene compound to conditions that promote release of the substance, and optionally, assaying release of the substance by spectroscopically or electrochemically interrogating the hexasubstituted benzene compound. Any of the hexasubstituted benzene compounds disclosed herein may be employed for this purpose, including those covalently bonded to a surface.

The type of surface attachment of the hexasubstituted benzenes in sensors and sensing applications is not considered to be particularly limited. In accordance with the disclosure above, particular types of surface attachment may include a cycloaddition product of a benzylic azide, or a secondary or tertiary benzylic amine reaction product or a secondary or tertiary benzylic amide reaction product of a primary benzylic amine.

Accordingly, methods for forming modified surfaces and sensor constructs comprising a surface modified with a hexasubstituted benzene may comprise: providing a surface having a plurality of functionalities reactive with an amine or an azide; contacting the surface with a hexasubstituted benzene having a structure represented by Compound 26

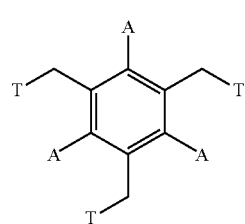

Compound 26 wherein each A is a vinyl group, a reaction product formed from a vinyl group, an epoxide, or a reaction product formed from opening of an epoxide with a nucleophile, and each T is independently, $N_3$ or $NH_2$; and reacting at least a portion of the plurality of functionalities with T to form a modified surface comprising a reaction product covalently bonded to the surface an having a structure represented by Compound 14

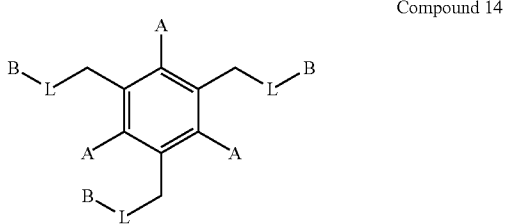

Compound 14 wherein B is the surface, and each L is a linking group connecting a benzylic carbon of the hexasubstituted benzene to the surface, each L being formed from a reaction between a functionality and T. In particular examples, the hexasubstituted benzene may have a structure represented by Compound 27

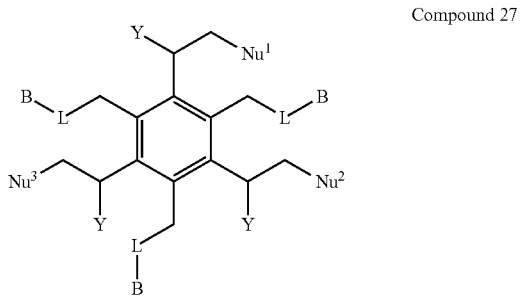

Compound 27 wherein $Nu^1$, $Nu^2$, and $Nu^3$ are nucleophiles, and each Y is independently H or OH, and L and B are specified as above. $Nu^1$, $Nu^2$, and $Nu^3$ may be the same or different and are specified in more detail above.

In summary, hexasubstituted benzenes and associated sensor constructs described herein may facilitate analyses of a wide range of fluids, both complex and non-complex in nature. The hexasubstituted benzenes may be robustly attached to the surface of a sensor construct in a highly orientationally controlled manner to accomplish the foregoing. Robust, orientationally controlled covalent bonding of a hexasubstituted benzene to a surface to promote analyte detection may overcome non-covalent detection approaches in which solutions of testing reagents are applied to a testing well or plate just prior to use. Such reagent loading appropriates are not feasible for flow-through sensing approaches with the testing agent remaining unbound. Covalent attachment of a hexasubstituted benzene to a surface may particularly facilitate development of flow-through sensors for high-throughput, in-line analyses of various types of process streams, particularly those involving complex fluids.

Moreover, the present disclosure provides a versatile chemical system engineered to function as a sensor when analyzing both simple and complex fluids. In a simple example, the present disclosure may allow one to detect the chemical identity of the constituents in common drinking water. More broadly, any number of liquids used in commercial, industrial, or medical applications may be analyzed using this technology. In specific examples, a fluid may be a liquid that may contain solids, other liquids or gases in water, or any combination thereof. Other types of complex fluids may also be compatible with the sensing technology described herein. The present disclosure may be applied in a wide range of ways to promote reaction-based detection of a desired chemical in a fluid and produce a measurable result. Beneficially, the chemical system described herein may generate measurement data for a specific target even when a fluid contains many other elements that would confuse or block other common sensor systems. As nonlimiting examples, measurements can be made using the present disclosure in complex fluids that include naturally occurring or industrial process fluids such as oilfield water, radioactive water, or geothermal brines; biological fluids such as blood; food items and the like. The chemical system of the present disclosure may also probe a surface without a "traditional" fluid being present, thereby providing measurement data to detect and quantify if an environmental surface has been exposed to specific toxins, bacteria, drugs, explosives, chemical weapons, poisons, or other elements of concern. As discussed herein, the chemical system has been engineered to feature a common scaffold with a design that includes a two-sided, or bifacial, features. The opposing faces of the hexasubstituted benzene compounds disclosed herein have different reaction profiles that are used in different combinations to provide various types of sensing functionalities. The different reaction profiles have simplified the ability to permanently attach the scaffold to a range of surfaces, such as glass, metal, or plastic, while at the same time allowing the opposite side of the hexasubstituted benzene compound to specifically target and sequester particular chemical and biological targets of interest. In some cases, the hexasubstituted benzene compound can act as a chemical sensor that generates a measurable physical quantity from changes to optical or electrical signals when a chemical or biological target is acquired, thereby providing a measurement value of the target. In another non-liming example, the hexasubstituted benzene compound can be preloaded with a captured element prior to use, such that the scaffold can deploy the preloaded element when in the presence of a specified chemical target. That is, the hexasubstituted benzene compounds may be employed as a delivery system as well. The hexasubstituted benzene compounds disclosed herein may be particularly useful for creating reactive surfaces during 3D printing, chemical coatings, material additives, quantitative chemical measurements, selective capture and removal of targets from a fluid, such as water remediation, and use as real-time, flow-through measurement sensors. Thus, the present disclosure thus provides the basis of a system applicable to a variety of pressing problems in many industries including, for example, food processing, medical devices, medical testing, oilfield fluid remediation, oilfield fluid analytical testing, 3D printing, microbiological screening, chemical coatings, industrial process optimizations, additives, and environmental remediation efforts.

Embodiments disclosed herein include:

A. Sensing methods. The methods comprise: exposing a fluid containing at least one analyte to a sensor construct comprising a hexasubstituted benzene having at least one sensing functionality capable of undergoing molecular association with the at least one analyte; determining an analytical response of the hexasubstituted benzene in the presence of the at least one analyte; and correlating the analytical response or a change thereof to an amount of the at least one analyte present in the fluid.

B. Sensor constructs. The sensor constructs comprise: a hexasubstituted benzene covalently bonded to a surface; wherein the hexasubstituted benzene comprises functionality capable of undergoing molecular association with at least one analyte, and functionality that is spectroscopically or electrochemically active to promote detection of the at least one analyte.

Each of embodiments A and B may have one or more of the following additional elements in any combination: 1 and 2; 1-3; 1 and 4; 1, 2 and 4; 1-4; 1 and 5; 1, 5 and 6; 1 and 5-7; 1, 5 and 7; 1 and 8; 1, 2 and 8; 1, 5 and 8; 1 and 9; 1, 9 and 10; 1, 9 and 11; 1 and 9-11; 1, 11 and 12; 1, 11 and 13; 1 and 11-13; 1 and 14; 1, 10, 12 and 14; 1, 14 and 15; 1, 15 and 16; 1 and 17; 1 and 18; 2 and 3; 2 and 4; 2-4; 5 and 6; 5 and 7; 5-7; 2 or 4, and 9; 2 or 4, 9 and 10; 2 or 4, and 9-11; 2 or 4, 11 and 12; 2 or 4, and 9-12; 2 or 4, 11 and 13; 2 or 4, and 11-13; 2 or 4, and 14; 2 or 4, 10 and 14; 2 or 4, 10, 12 and 14; 2 or 4, 14 and 15; 2 or 4, 15 and 16; 2 or 4, 10 and 17; 2 or 4, 9 and 17; 2 or 4, 11 and 17; 2 or 4, 11, 12 and 17; 2 or 4, 11, 12, 13 and 17; 2 or 4, and 17; 2 or 4, and 18; 2 or 4, 9, 10 and 18; 2 or 4, 17 and 18; 8 and 9; 8, 9 and 10; 8 and 9-11; 8, 11 and 12; 8 and 9-12; 8, 11 and 13; 8 and 11-13; 8 and 14; 8, 10 and 14; 8, 10, 12 and 14; 8, 14 and 15; 8, 15 and 16; 8, 10 and 17; 8, 9 and 17; 8, 11 and 17; 8, 11, 12 and 17; 8, 11, 12, 13 and 17; 8 and 17; 8 and 18; 8, 9, 10 and 18; 8, 17 and 18; 9 and 10; 9-11; 11 and 12; 9-12; 11 and 13; 11-13; 14 and 17; 14 and 18; 10 and 14; 10, 12 and 14; 14 and 15; 15 and 16; 10 and 17; 9 and 17; 11 and 17; 11, 12 and 17; 11, 12, 13 and 17; 9, 10 and 18; and 17 and 18.

Element 1: wherein the fluid comprises a single-phase or multi-phase complex fluid.

Element 2: wherein the fluid comprises an oilfield fluid.

Element 3: wherein the oilfield fluid comprises oil, gas, a treatment fluid, produced water, or any combination thereof.

Element 4: wherein the method further comprises conducting or modifying a treatment operation based upon the analytical response or the change thereof.

Element 5: wherein the fluid comprises a biological fluid.

Element 6: wherein the biological fluid comprises blood, plasma, saliva, urine, cerebrospinal fluid, gastric fluid, or any combination thereof.

Element 7: wherein the method further comprises making a diagnosis, determining a course of treatment, or any combination thereof based upon the analytical response or the change thereof.

Element 8: wherein the fluid comprises a multi-phase complex fluid selected from a liquid-liquid, solid-liquid, gas-liquid, solid-gas, or gas-liquid-solid complex fluid.

Element 9: wherein the hexasubstituted benzene is covalently bonded to a surface.

Element 10: wherein the surface is selected from the group consisting of a polymer surface, a metal surface, a ceramic surface, a glass surface, a cement surface, a wood surface, a geological surface, and any combination thereof.

Element 11: wherein the hexasubstituted benzene has a structure of

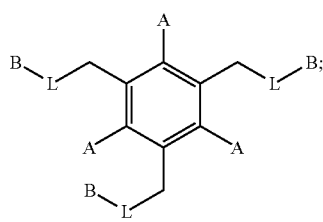

when covalently bonded to the surface; wherein B is the surface; wherein each A is a reaction product formed from opening of an epoxide with a nucleophile; and wherein each L is a linking group connecting a benzylic carbon of the hexasubstituted benzene to the surface, each L being formed as a reaction product of an azide or a primary amine located upon the benzylic carbon.

Element 12: wherein each L comprises a cycloaddition reaction product of the azide, a secondary or tertiary amine reaction product of the primary amine, or a secondary or tertiary amide reaction product of the primary amine.

Element 13: wherein each A has a structure of —CH(Y)CH$_2$(Nu); wherein Y is H or OH, and Nu is the nucleophile.

Element 14: wherein the hexasubstituted benzene has a structure of

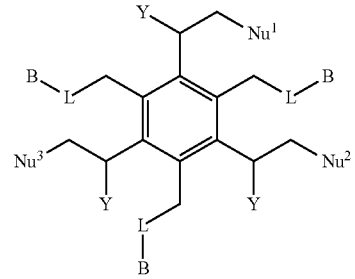

wherein Nu$^1$, Nu$^2$ and Nu$^3$ are each nucleophiles, and each Y is independently H or OH.

Element 15: wherein Nu$^1$, Nu$^2$ and Nu$^3$ are each different.

Element 16: wherein at least one of Nu$^1$, Nu$^2$ and Nu$^3$ includes functionality that is spectroscopically or electrochemically active to promote detection of the at least one analyte.

Element 17: wherein the molecular association of the at least one analyte is coordinative with a ligand present upon the hexasubstituted benzene.

Element 18: wherein the sensor construct comprises a plate-based sensor or a flow-through sensor.

By way of non-limiting example, exemplary combinations applicable to A and B include, but are not limited to:

Additional embodiments disclosed herein include:

A'. Hexasubstituted benzenes having a structure of

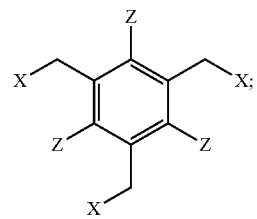

wherein each X is independently Cl, Br or N$_3$, and each Z is independently —CH(Br)CH$_3$, —CH(N$_3$)CH$_3$, —CH=CH$_2$, —CH$_2$CH$_3$,

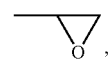

or, —CH$_2$CH$_2$SiR'$_3$;

wherein R' is a hydrocarbyl group.

B'. Hexasubstituted benzenes having a structure of

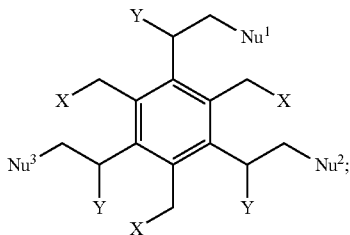

wherein $Nu^1$, $Nu^2$ and $Nu^3$ are each nucleophiles, each X is independently Cl, Br, $N_3$ or $NH_2$, and each Y is independently H or OH.

C'. Surfaces modified with a hexasubstituted benzene. The modified surfaces comprise: a base surface having a plurality of functionalities reactive with an amine or an azide; and a reaction product of the base surface and a hexasubstituted benzene bearing an amine or an azide, the reaction product being covalently bonded to the base surface and having a structure of

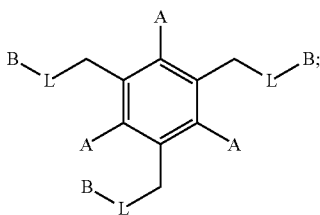

wherein B is the base surface; wherein each A is a vinyl group, a reaction product of a vinyl group, an epoxide, or a reaction product formed from opening of an epoxide with a nucleophile; and wherein each L is a linking group connecting a benzylic carbon of the hexasubstituted benzene to the base surface, each L being formed from a reaction between a functionality and an azide or an amine located upon the benzylic carbon.

D'. Sensors comprising a surface modified with the hexasubstituted benzene of C, wherein at least one of $Nu^1$, $Nu^2$ and $Nu^3$ includes functionality that associates with an analyte of interest; wherein association between the analyte of interest and the functionality of at least one of $Nu^1$, $Nu^2$ and $Nu^3$ is analytically detectable and an extent of the association is correlatable to an amount of the analyte of interest that is present in a sample.

E'. Methods for functionalizing a surface with a hexasubstituted benzene. The methods comprise: providing a base surface having a plurality of functionalities reactive with an amine or an azide; contacting the base surface with a hexasubstituted benzene having a structure of

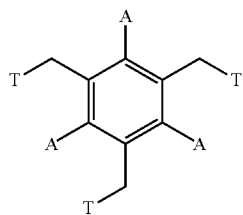

wherein each A is a vinyl group, a reaction product formed from a vinyl group, an epoxide, or a reaction product formed from opening of an epoxide with a nucleophile; and wherein each T is independently $N_3$ or $NH_2$; and reacting at least a portion of the plurality of functionalities with T to form a modified surface comprising a reaction product covalently bonded to the base surface and having a structure of

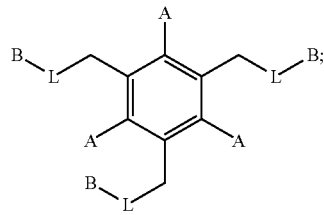

wherein B is the base surface; and wherein each L is a linking group connecting a benzylic carbon of the hexasubstituted benzene to the base surface, each L being formed from a reaction between a functionality and T.

Each of embodiments A'-E' may have one or more of the following additional elements in any combination:

Element 1': wherein each Z is independently —CH(Br)CH$_3$, —CH=CH$_2$, or

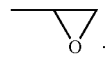

Element 2': wherein each Z is —CH(Br)CH$_3$ and each X is Br or each X is Cl.

Element 3': wherein each Z is —CH=CH$_2$ and each X is Br or each X is Cl.

Element 4': wherein each Z is —CH=CH$_2$ and each X is $N_3$.

Element 5': wherein each Z is

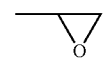

and each X is Br or each X is Cl.

Element 6': wherein each Z is

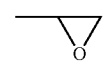

and each X is $N_3$.

Element 7': wherein each X is Br or each X is Cl.
Element 8': wherein each X is $N_3$.
Element 9': wherein each X is $NH_2$.
Element 10': wherein $Nu^1$, $Nu^2$ and $Nu^3$ are each different.
Element 11': wherein $Nu^1$, $Nu^2$ and $Nu^3$ are orthogonally protected amines.
Element 12': wherein each Y is OH.
Element 13': wherein L comprises a cycloaddition reaction product of a benzylic azide.
Element 14': wherein the cycloaddition reaction product is a 1,2,3-triazole.
Element 15': wherein L comprises a secondary or tertiary benzylic amine reaction product or a secondary or tertiary benzylic amide reaction product of a primary benzylic amine.

Element 16': wherein each A is an epoxide or a reaction product formed from opening of an epoxide with a nucleophile.

Element 17': wherein each A has a structure of —CH(Y)CH$_2$(Nu); wherein Y is H or OH, and Nu is the nucleophile.

Element 18': wherein a first nucleophile Nu$^1$ reacts with a first epoxide, a second nucleophile Nu$^2$ reacts with a second epoxide, and a third nucleophile Nu$^3$ reacts with a third epoxide.

Element 19': wherein the reaction product has a structure of

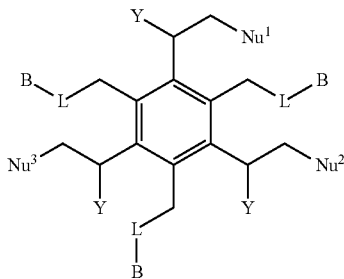

wherein Nu$^1$, Nu$^2$ and Nu$^3$ are each nucleophiles, and each Y is independently H or OH.

Element 20': wherein the base surface is selected from the group consisting of a polymer surface, a metal surface, a ceramic surface, a glass surface, a cement surface, a wood surface, a geological surface, and any combination thereof.

Element 21': wherein the association is coordinative with a ligand present upon the hexasubstituted benzene.

Element 22': wherein at least one of Nu$^1$, Nu$^2$ and Nu$^3$ includes functionality that is spectroscopically or electrochemically active to promote detection of the analyte of interest.

Element 23': wherein each A is an epoxide or a reaction product formed from opening of an epoxide with a nucleophile.

Element 24': wherein each A has a structure of —CH(Y)CH$_2$(Nu); wherein Y is H or OH, and Nu is the nucleophile.

Element 25': wherein the hexasubstituted benzene has a structure of

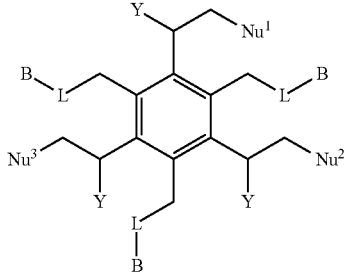

wherein Nu$^1$, Nu' and Nu$^3$ are each nucleophiles, and each Y is independently H or OH.

By way of non-limiting example, exemplary combinations applicable to B' include, but are not limited to: 7', 8' or 9', and 10'; 7', 8' or 9', and 11'; 7', 8' or 9', and 12'; 10' and 11'; and 10' and 12'. Exemplary combinations applicable to C' include, but are not limited to: 13' and 14'; 13', 14' and 16'; 15' and 16'; 15' and 17'; 13' and 18'; 13', 18' and 19'; 13', 18', 19' and 12'; 15', 18', and 19'; 15', 18', 19' and 12'; 13' and 20'; 15' and 20'; 10' and 13'; and 10' and 15'. Exemplary combinations applicable to D' include, but are not limited to: 21' and 22'; 22' and 24'; 22' and 13'; 22' and 15'; 24' and 13'; and 24' and 15'. Exemplary combinations applicable to E' include, but are not limited to: 20' and 23'; 20' and 24'; 20' and 25'; 25' and 10'; 25' and 11'; 20' and 13'; 20' and 15'; 23' and 13'; 24' and 13'; 23' and 15' and 24' and 15.

To facilitate a better understanding of the disclosure herein, the following examples of various representative embodiments are given. In no way should the following examples be read to limit, or to define, the scope of the invention.

EXAMPLES

Compound A: 1,3,5-Tris(chloromethyl)-2,4,6-triethylbenzene. The title compound was synthesized as described in K. J. Wallace, et al., "Preparation of 1,3,5-Tris(aminomethyl)-2,4,6-triethylbenzene from Two Versatile 1,3,5-Tri (halosubstituted) 2,4,6-Triethylbenzene Derivatives," Synthesis, 2005, pp. 2080-2083. In particular, 1,3,5-triethylbenzene was reacted with chloromethyl methyl ether in CS$_2$ in the presence of SnCl$_4$ to afford the title compound. CAUTION: chloromethyl methyl ether is a potent carcinogen.

Compound B: 1,3,5-Tris(bromomethyl)-2,4,6-triethylbenzene. The title compound was synthesized as described in K. J. Wallace, et al., "Preparation of 1,3,5-Tris(aminomethyl)-2,4,6-triethylbenzene from Two Versatile 1,3,5-Tri (halosubstituted) 2,4,6-Triethylbenzene Derivatives," Synthesis, 2005, pp. 2080-2083. In particular, 1,3,5-triethylbenzene was reacted with HBr, acetic acid and Zn powder to afford the title compound.

Figure 2:
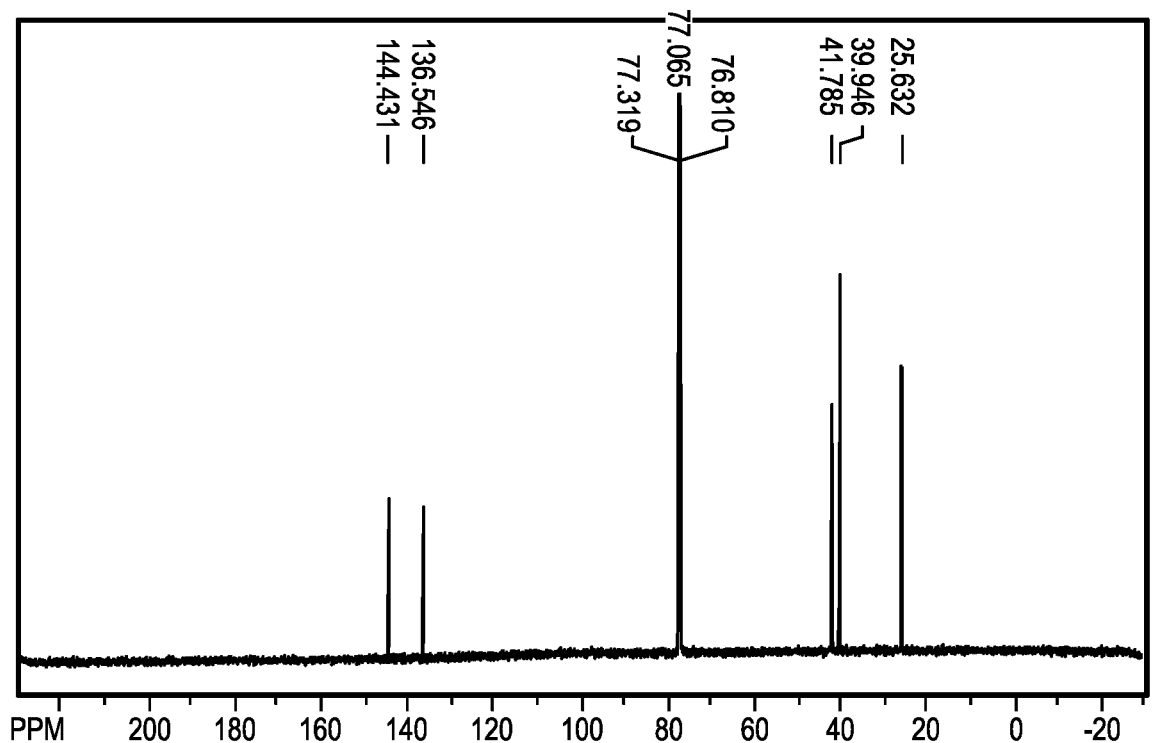
Figure 3:
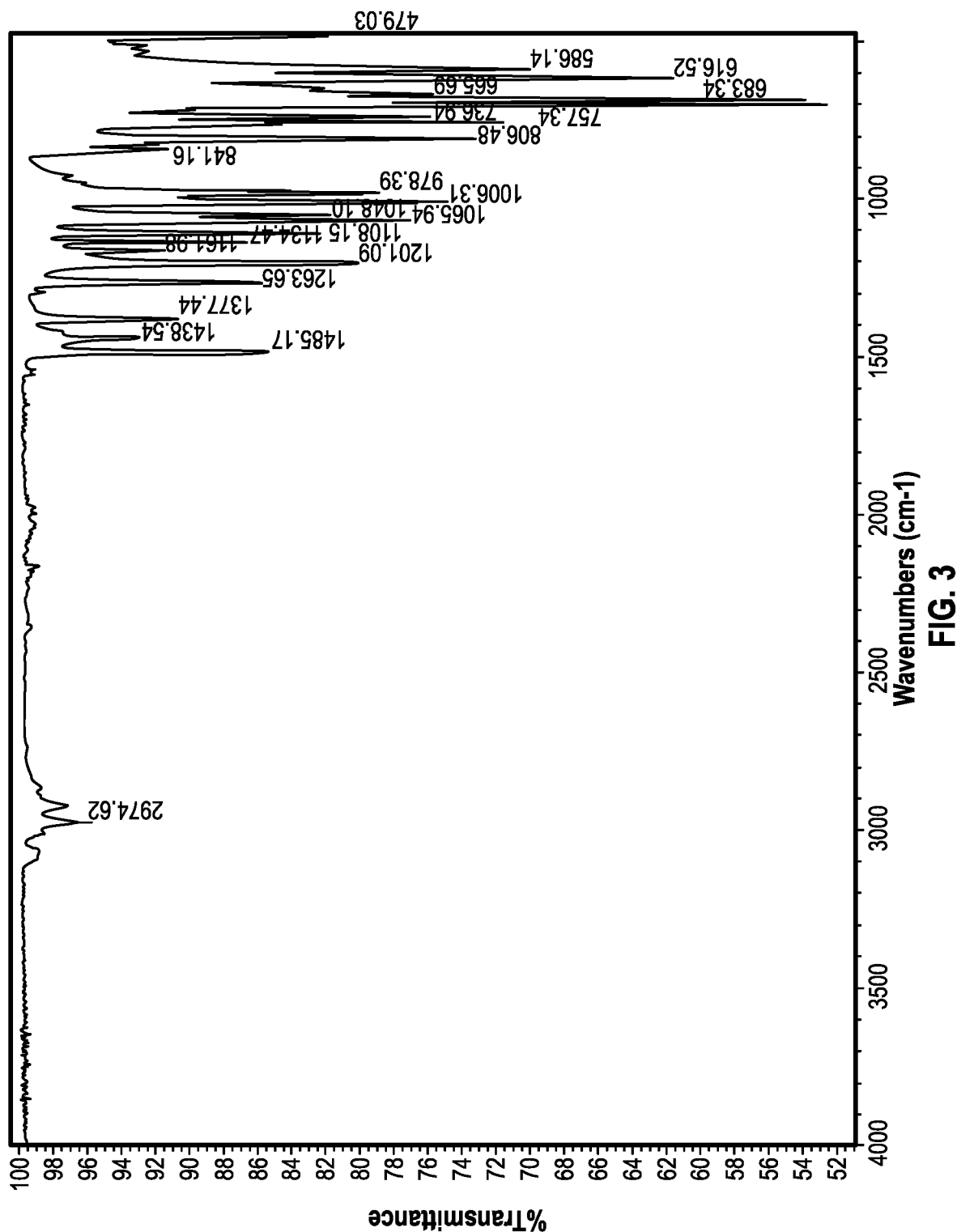
FIG. 3 is an infrared spectrum of 1,3,5-tris(halomethyl)-2,4,6-tris(α-bromoethyl)benzene.
Figure 4:
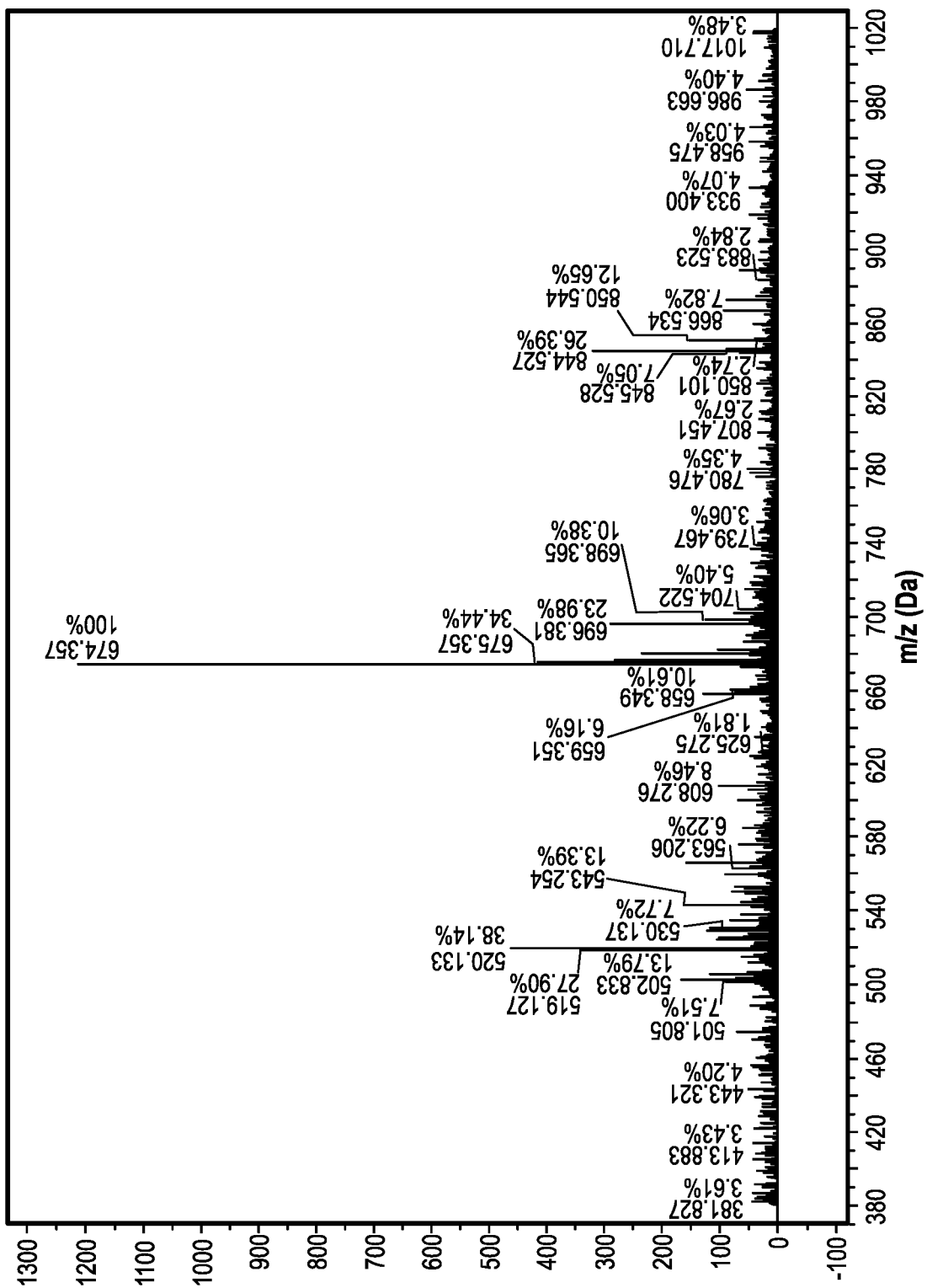
FIG. 4 is MALDI-TOF mass spectrometry data of 1,3,5-tris(halomethyl)-2,4,6-tris(α-bromoethyl)benzene.
Figure 5:
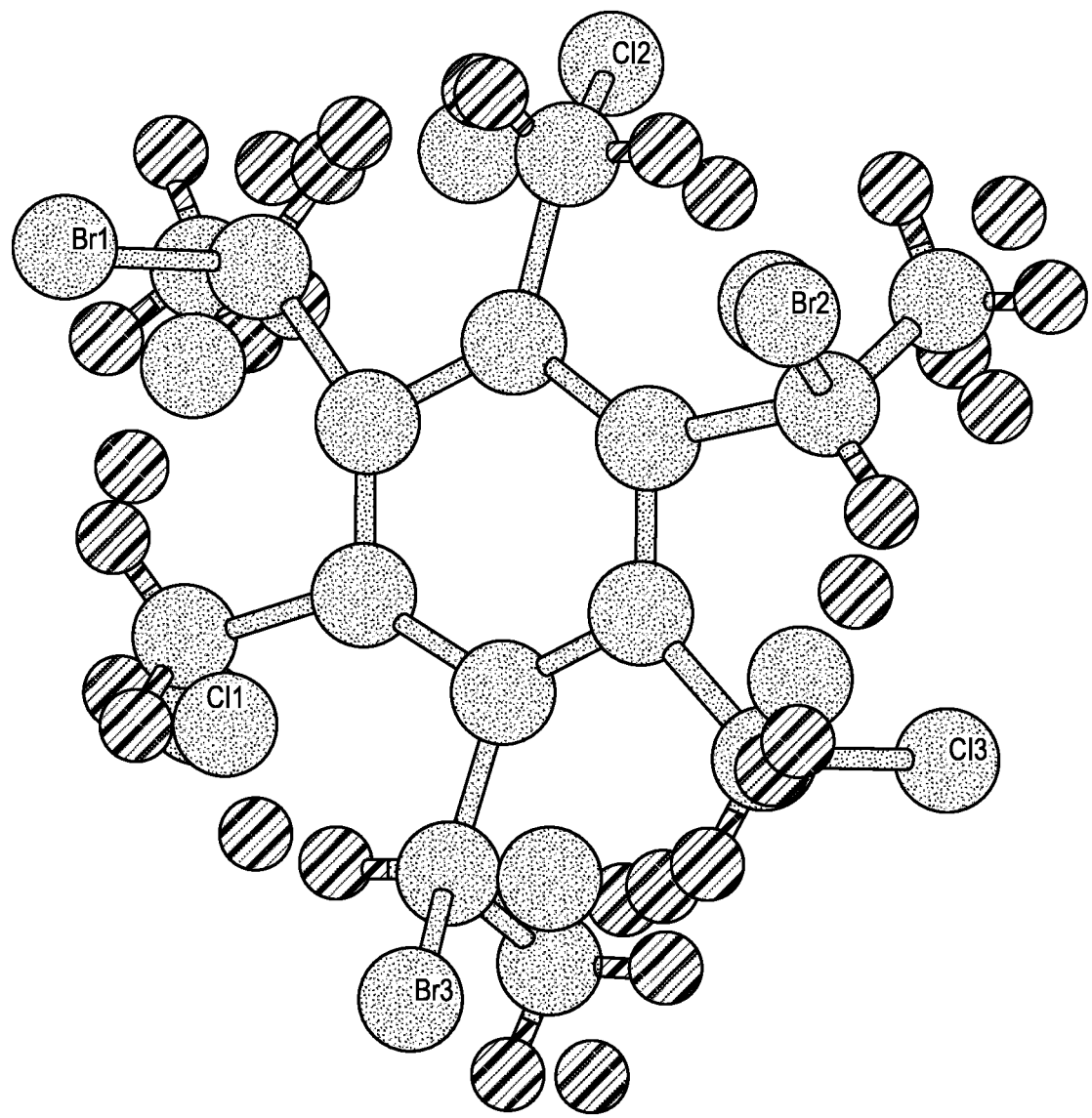
FIG. 5 is a depiction of the crystal structure of 1,3,5-tris (halomethyl)-2,4,6-tris(α-bromoethyl)benzene.

Compound C: 1,3,5-Tris(bromomethyl)-2,4,6-tris(α-chloroethyl)benzene. The title compound was synthesized by reacting Compound A or Compound B with excess N-bromosuccinimide (NBS) in CCl$_4$. In one example, Compound A was dissolved in CCl$_4$, and 3 molar equivalents of NBS were added. The reaction was heated to reflux, and 0.1 molar equivalents of AIBN were added. The title compound was isolated by aqueous workup and column chromatography. When the reaction was conducted with >6 molar equivalents of NBS, halide exchange of the benzylic chloride for bromides took place. FIGS. 1 and 2 are $^1$H and $^{13}$C NMR spectra of the title compound in CDCl$_3$, respectively. FIG. 3 is an infrared spectrum of the title compound. FIG. 4 shows Maldi-TOF mass spectrometry data of the title compound. FIG. 5 shows a depiction of the crystal structure of the title compound.

Compound D: 1,3,5-Tris(bromomethyl)-2,4,6-trivinylbenzene. The title compound was synthesized by reacting Compound C with excess potassium t-butoxide in t-butanol. Compound C was combined with 3 molar equivalents of potassium t-butoxide in t-butanol and reacted at 70° C. The product was isolated essentially quantitatively after aqueous workup. FTIR (not shown) showed the appearance of a new C=C stretch and a new C—H stretch centered at 1660 cm$^{-1}$ and 3084 cm$^{-1}$, respectively.

Compound E: 1,3,5-Tris(bromomethyl)-2,4,6-triepoxybenzene. The title compound was synthesized by reacting Compound D with dimethyldioxirane in acetone. Compound D was first dissolved in methylene chloride and a solution of dimethyldioxirane in acetone was added. The dimethyldioxirane was prepared in situ by reacting potassium peroxymonosulfate (OXONE) with acetone. The reaction was continued until the C=C stretch was absent by FTIR. The title compound was obtained essentially quantitatively.

Figure 6:
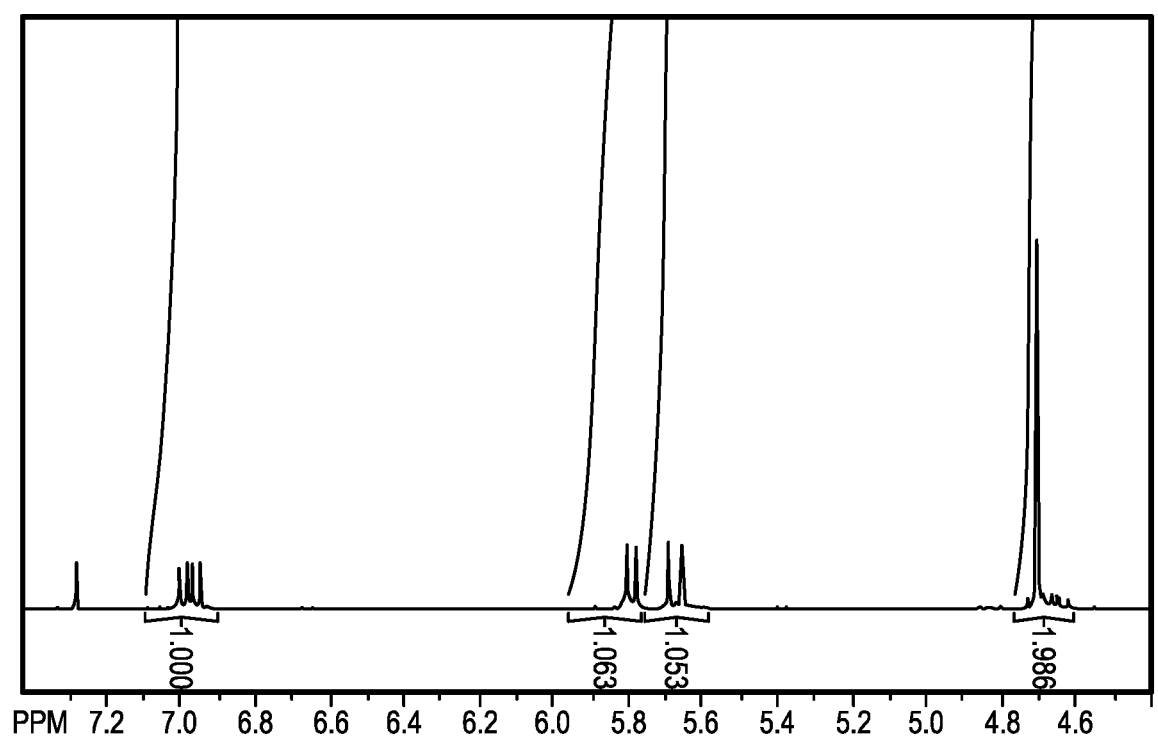
FIG. 6 is a $^1$H NMR spectrum of 1,3,5-tris(bromomethyl)-2,4,6-triepoxybenzene in $CDCl_3$.

Alternately, the title compound may be prepared by reacting Compound D with m-chloroperoxybenzoic acid (mCPBA). FIG. 6 is a $^1$H NMR spectrum of the title compound in CDCl$_3$.

Figure 7:
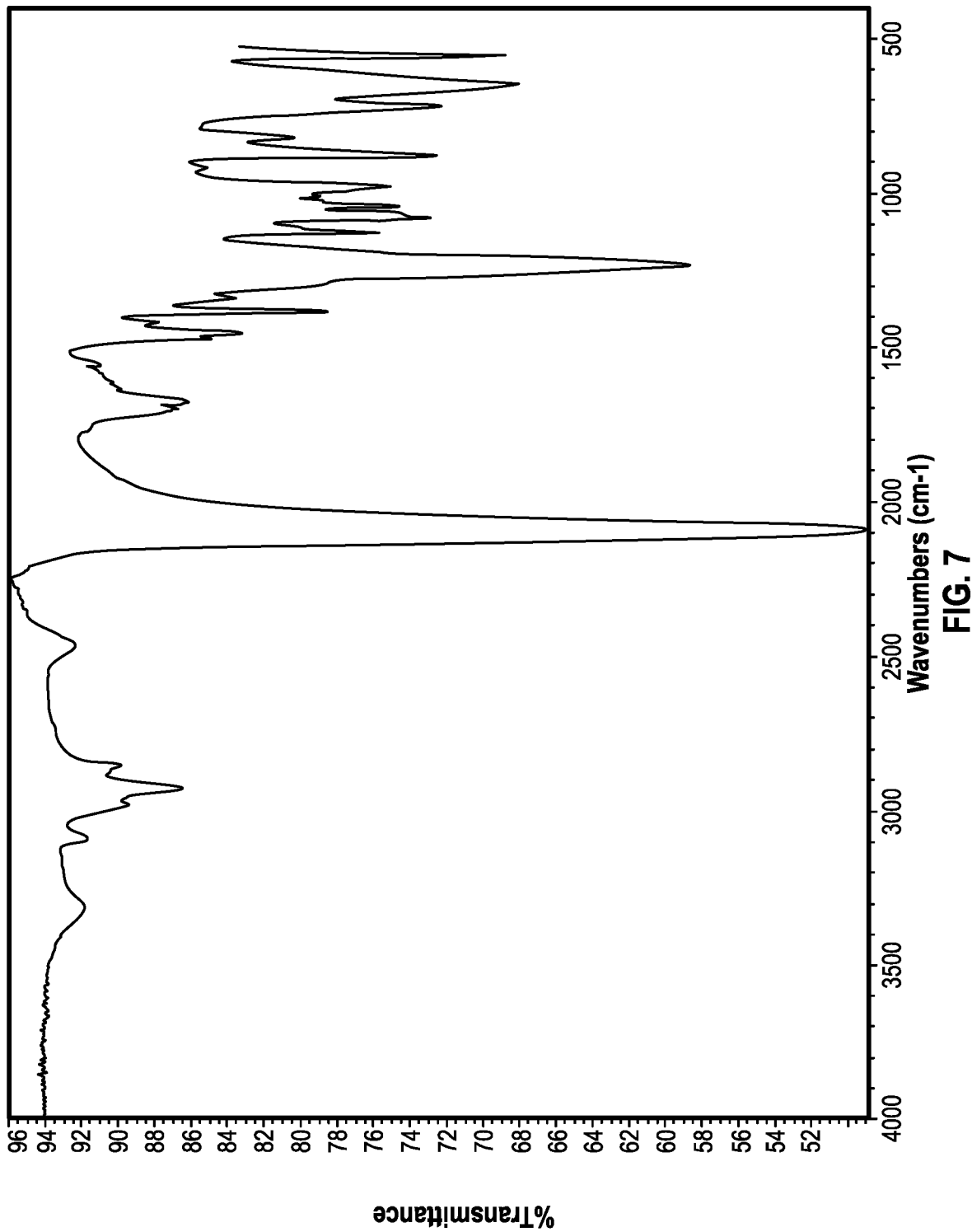
FIG. 7 is an infrared spectrum of 1,3,5-tris(azidomethyl)-2,4,6-triepoxybenzene.

Compound F: 1,3,5-Tris(azidomethyl)-2,4,6-triepoxybenzene. The title compound was synthesized by reacting Compound E with sodium azide in DMF at room temperature. CAUTION: NaN$_3$ may be explosive under some conditions and is highly toxic. No epoxide opening was observed. FIG. 7 is an infrared spectrum of the title compound.

Iron Binding. Hexasubstituted benzenes capable of binding iron (Fe$^{2+}$ and/or Fe$^{3+}$) were synthesized in accordance with Scheme 10 below.

Methacrylic acid was dissolved in acetonitrile and deprotonated with cesium carbonate. Compound E was heated with the cesium carboxylate in acetonitrile at reflux under inert atmosphere. The product was isolated by aqueous workup and column chromatography, and characterization by NMR, FTIR and mass spectrometry was performed.

Thereafter, the benzylic halides were displaced with sodium azide in a polar aprotic solvent, such as DMF. Reduction of the covalently bound azides with triphenylphosphine was then conducted in a THF/water mixture. The resulting amines were then acylated with 2,3-diacetoxybenzoyl chloride (2-5% molar excess) in the presence of a hindered amine base (5-10% molar excess), such as trieth-

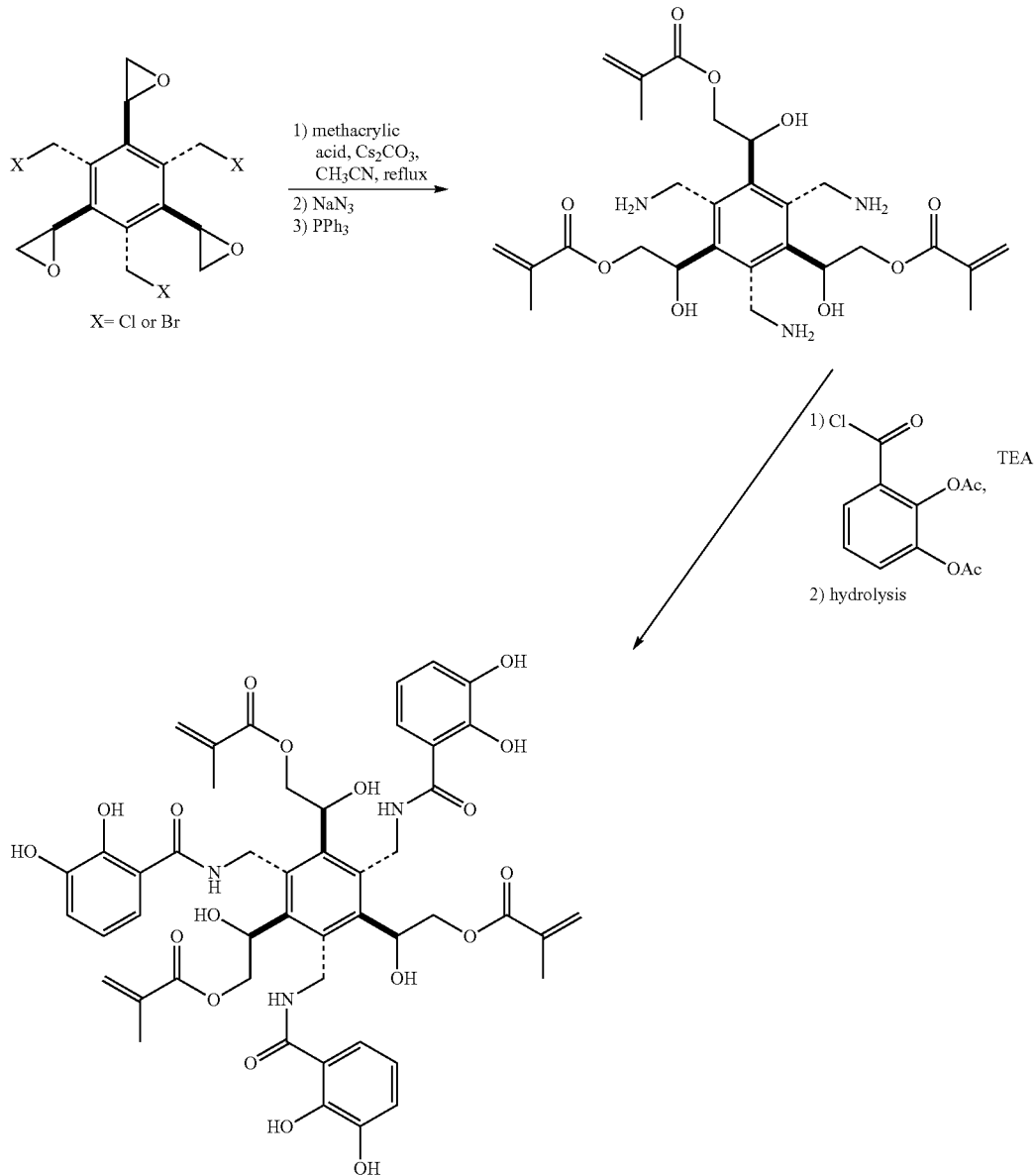

Scheme 10

In brief, the epoxides of Compound E were nucleophilically opened by methacrylate in the presence of cesium carbonate and a polar aprotic solvent such as acetonitrile.

ylamine. The acylated product was isolated by aqueous workup and column chromatography, and characterization by NMR, FTIR and mass spectrometry were performed. The acetate protecting groups may be removed by mild basic hydrolysis or in situ removal may occur when contacting a solution containing iron ions.

The acylated hexasubstituted benzene exhibited a linear response to increasing concentrations of iron ions in an aqueous solution, sometimes containing methanol or acetonitrile as a co-solvent to aid in solubility. The maximum absorbance intensity changed at various pH values. A buffer was used during the pH-dependence measurements (acetate, TRIS, MES and MOPS buffers were used). A 1:1 binding ratio of metal to catechol functional groups was determined by a Job plot.

Lithium Binding. Hexasubstituted benzenes capable of binding lithium ($Li^+$, particularly in hydrated form) were synthesized in accordance with Scheme 11 below.

intensity was proportional to the amount of added lithium. The change from purple to blue is believed to be indicative of competitive displacement of the dye from the hexasubstituted benzene by the lithium ions. Again, a linear increase in absorbance intensity was observed with increasing amounts of added lithium ions.

The same compound was also covalently bonded to a polymer macroparticulate. The macroparticulate-bound lithium-binding compound was then exposed to a lithium ion solution containing celestine blue dye at a pH of 4.5 maintained with an acetate buffer. Prior to adding of the macroparticulates to the lithium ion solution, the dye color was purple. Following addition of the macroparticulates, the color change was reversed to afford a blue color.

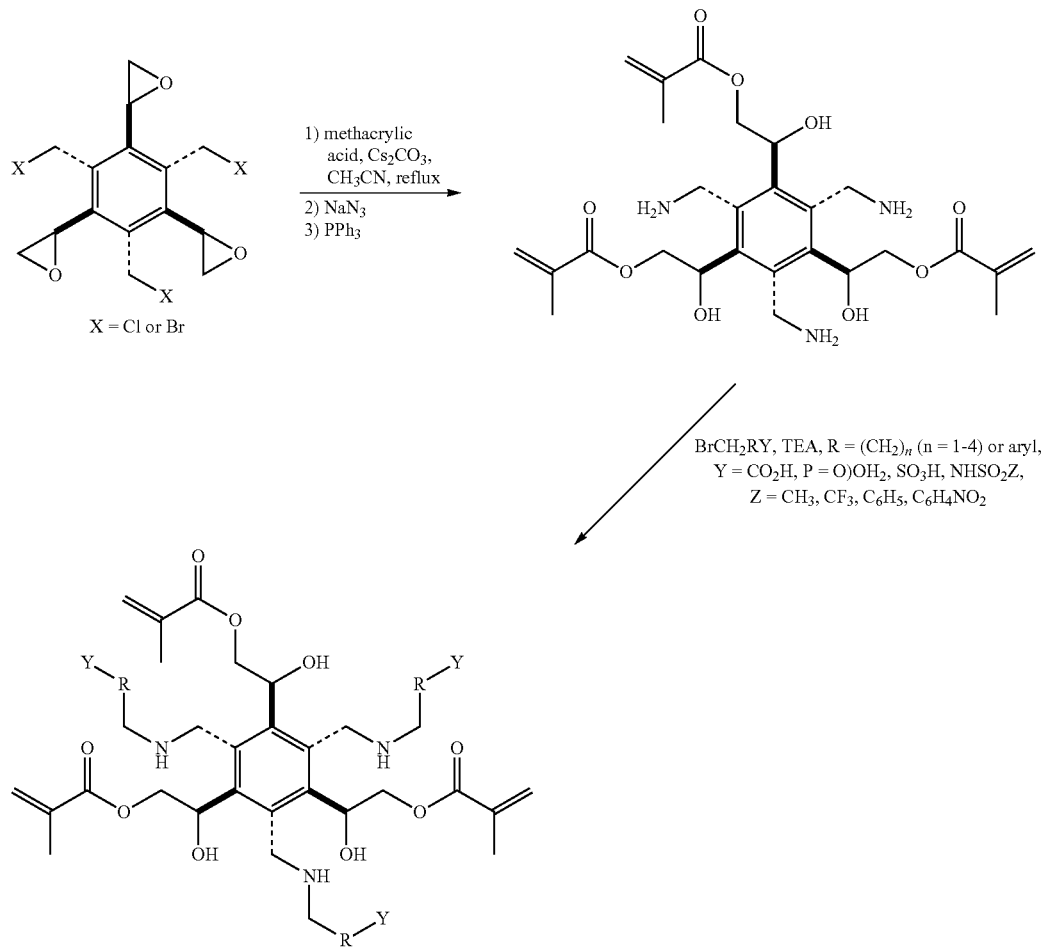

Scheme 11

The synthesis was carried out in a similar manner to that described above for preparing an iron-binding compound, except a halocarboxylic acid, halosulfonic acid, halophosphonic acid, or halosulfonamide was employed to alkylate the amine groups.

Lithium sequestration was measured for the analogue with $R=(CH_2)_3$ and $Y=CO_2H$ in a methanol-water solution having a pH of 4.5 maintained with an acetate buffer. Addition of celestine blue dye afforded a color change from blue to purple. When back titration with lithium chloride was performed, the blue color returned, and the color Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A sensing method comprising:
  exposing a fluid containing at least one analyte to a sensor construct comprising a hexasubstituted benzene having at least one sensing functionality capable of undergoing molecular association with the at least one analyte, wherein the fluid comprises an oilfield fluid comprising oil, gas, a treatment fluid, produced water, or any combination thereof;
  determining an analytical response of the hexasubstituted benzene in the presence of the at least one analyte; and
  correlating the analytical response or a change thereof to an amount of the at least one analyte present in the fluid.

2. The method of claim 1, wherein the fluid comprises a single-phase or multi-phase complex fluid.

3. The method of claim 1, further comprising:
  Conducting or modifying a treatment operation based upon the analytical response or the change thereof.

4. The method of claim 1, wherein the fluid comprises a multi-phase complex fluid selected from the group consisting of a liquid-liquid, solid-liquid, gas-liquid, solid-gas, or gas-liquid-solid complex fluid.

5. The method of claim 1, wherein the hexasubstituted benzene is covalently bonded to a surface.

6. The method of claim 5, wherein the surface is selected from the group consisting of a polymer surface, a metal surface, a ceramic surface, a glass surface, a cement surface, a wood surface, a geological surface, and any combination thereof.

7. The method of claim 5, wherein the hexasubstituted benzene has a structure of

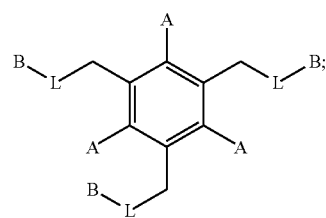

when covalently bonded to the surface;
  wherein B is the surface;
  wherein each A is a reaction product formed from opening of an epoxide with a nucleophile; and
  wherein each L is a linking group connecting a benzylic carbon of the hexasubstituted benzene to the surface, each L being formed as a reaction product of an azide or a primary amine located upon the benzylic carbon.

8. The method of claim 7, wherein each L comprises a cycloaddition reaction product of the azide, a secondary or tertiary amine reaction product of the primary amine, or a secondary or tertiary amide reaction product of the primary amine.

9. The method of claim 7, wherein the hexasubstituted benzene has a structure of

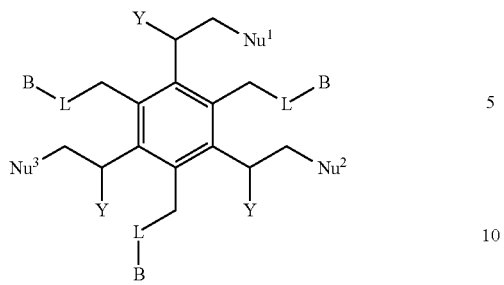

wherein $Nu^1$, $Nu^2$ and $Nu^3$ are each nucleophiles, and each Y is independently H or OH.

10. The method of claim 9, wherein $Nu^1$, $Nu^2$ and $Nu^3$ are each different.

11. The method of claim 9, wherein at least one of $Nu^1$, $Nu^2$ and $Nu^3$ includes functionality that is spectroscopically or electrochemically active to promote detection of the at least one analyte.

12. The method of claim 1, wherein the sensor construct comprises a plate-based sensor or a flow-through sensor.

* * * * *